US012214031B2

(12) United States Patent
Briggs et al.

(10) Patent No.: US 12,214,031 B2
(45) Date of Patent: *Feb. 4, 2025

(54) MANNHEIMIA HAEMOLYTICA VECTOR

(71) Applicant: The United States of America, as represented by The Secretary of Agriculture, Washington, DC (US)

(72) Inventors: Robert E. Briggs, Boone, IA (US); Fred M. Tatum, Nevada, IA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/310,821

(22) Filed: May 2, 2023

(65) Prior Publication Data

US 2023/0330204 A1 Oct. 19, 2023

Related U.S. Application Data

(62) Division of application No. 17/190,182, filed on Mar. 2, 2021, now Pat. No. 11,679,150.

(60) Provisional application No. 62/984,700, filed on Mar. 3, 2020.

(51) Int. Cl.
| | |
|---|---|
| *A61K 39/102* | (2006.01) |
| *A61K 39/04* | (2006.01) |
| *A61P 31/04* | (2006.01) |
| *A61K 39/00* | (2006.01) |

(52) U.S. Cl.
CPC ............ *A61K 39/102* (2013.01); *A61K 39/04* (2013.01); *A61P 31/04* (2018.01); *A61K 2039/5256* (2013.01)

(58) Field of Classification Search
CPC .................................................. A61K 39/102
See application file for complete search history.

(56) References Cited

U.S. PATENT DOCUMENTS

| | | | |
|---|---|---|---|
| 6,331,303 B1 | 12/2001 | Briggs et al. | |
| 11,690,901 B2 * | 7/2023 | Perez De Leon | ............................ C07K 14/43527 424/190.1 |
| 2017/0022510 A1 | 1/2017 | Briggs et al. | |

FOREIGN PATENT DOCUMENTS

WO  00-44392 A2  8/2000

OTHER PUBLICATIONS

Beltrán, P.K. et al., 2011, Identification of immunodominant antigens of Mycobacterium bovis by expression library immunization, Vet. J. 190:181-183.
Chen, S. et al., 2018, Differential immunoreactivity to bovine convalescent serum between Mycoplasma bovis biofilms and planktonic cells revealed by comparative immunoproteomic analysis, Front. Microbiol. vol. 9, article No. 379, pp. 1-12.
Jiang, F. et al., 2016, Elongation factor Tu and heat shock protein 70 are membrane-associated proteins from Mycoplasma ovipneumoniae capable of inducing strong immune response in mice, PloS one, vol. 11, No. 8, article No. e0161170, pp. 1-17.

* cited by examiner

*Primary Examiner* — Albert M Navarro
(74) *Attorney, Agent, or Firm* — John D. Fado; Maria Restrepo-Hartwig

(57) ABSTRACT

The present invention relates to modified *Mannheimia haemolytica* (*M. haemolytica*) lktCA gene cluster cassettes, compositions comprising such cassettes, methods of using such cassettes and compositions, and kits comprising such cassettes and compositions. Also described herein are *Mycoplasma bovis* (*M. bovis*) protective antigens, compositions comprising such antigens, methods of using such antigens and compositions, and kits comprising such antigens and compositions. Also described herein are modified *M. haemolytica* lktCA gene cluster cassettes engineered to express *M. bovis* protective antigens, compositions comprising such cassettes, methods of using such cassettes and compositions, and kits comprising such cassettes and compositions.

10 Claims, 9 Drawing Sheets

Specification includes a Sequence Listing.

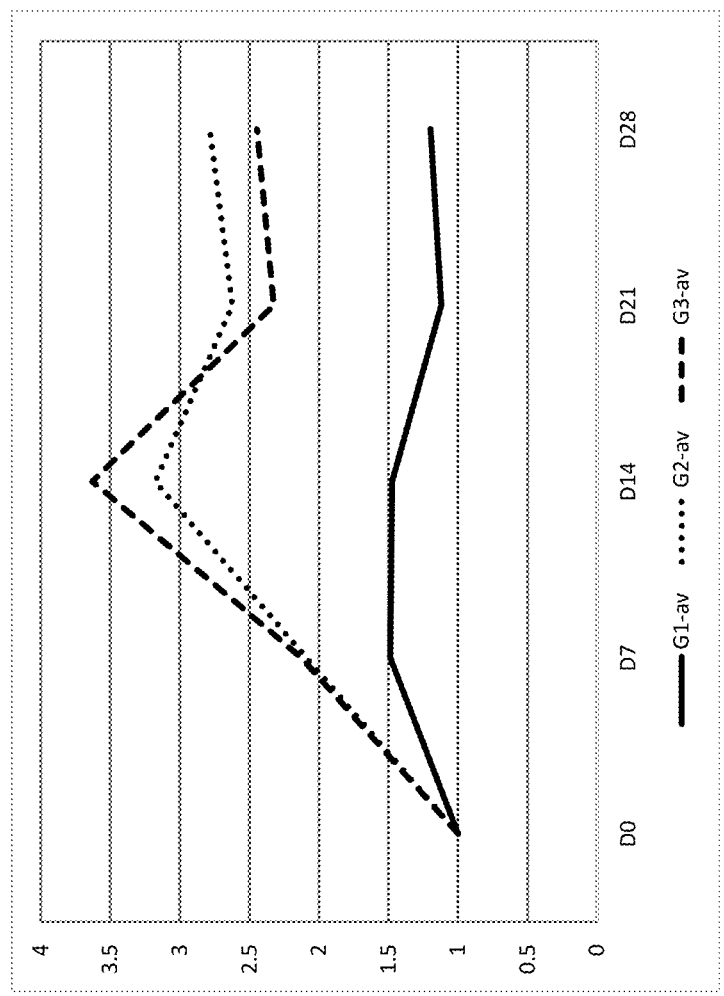

SEQUENCE LISTING

```
Sequence total quantity: 29
SEQ ID NO: 1              moltype = DNA   length = 4364
FEATURE                   Location/Qualifiers
source                    1..4364
                          mol_type = genomic DNA
                          organism = Mannheimia haemolytica
SEQUENCE: 1
ttctcttttg ctaaatagtg ttggtaagta gtcccatttt gcacaccaat cgttttcacc   60
ttagcaaaat ctgtatcttt tttcgcaatg aaggcagcag agcttggaaa gtaaggctcg  120
ctaaataata cttgtttctt acgtggttcc gtaaatccca tacctgaaat tgcagcatca  180
aattgttttt gttttaggct ttggattaag ctatcaaaag gttggctatg gaatgtacaa  240
tttgcattca tctctttaca gatagcattt gcaatatcca catcaaaacc gataatttct  300
cccttctctt cggtcatttc aaatggagga tagcttggct ccatcacaaa tttgatatct  360
tgtgcctgcg cagtaaccac acacccgaat aaaagggtca aaagtgtttt tttcataaaa  420
agtccctgtg ttttcattat aaggattacc acttcaacgc agttacttct taaaaaaaag  480
tcttcttttc ataaagtttg ttttatgtca tacaaacaca tcaaattgag atgtagtttc  540
tcaatcctct tgattcctct atctcaaaaa aacaacccaa aagaaaaaag aaaagtatat  600
gttacattaa tattacaatg taattatttt gtttaatttc cctacatttt gtataacttt  660
aaaacactcc tttttctctt ctgattatat aaaagcaaaa aaatacaatt taagctacaa  720
aaaacaacaa aaaacaacaa aaaacacgac aataagatcg agtaatgatt atattatgtt  780
ataattttg acctaattta gaataattat cgagtgcaaa ttatgaatca atcttatttt  840
aacttactag gaaacattac ttggctatgg atgaactcct ccctccacaa agaatggagc  900
tgtgaactac tagcacgcaa tgtgattcct gcaattgaaa atgaacaata tatgctactt  960
atagataacg gtattccgat cgcttattgt agttgggcag atttaaacct tgagactgag 1020
gtgaaatata ttaaggatat taattcgtta acaccagaag aatggcagtc tggtgacaga 1080
cgctggatta ttgattgggt agcaccattc ggacattctc aattactttta taaaaaaatg 1140
tgtcagaaat accctgatat gatcgtcaga tctatacgct ttatccaaa gcagaaagaa 1200
ttaggcaaaa ttgcctactt taaaggaggt aaattagata aaaaaacagc aaaaaaacgt 1260
tttgatacat atcaagaaga gctggcaaca gcacttaaaa atgaatttaa ttttattaaa 1320
aaatagaagg agacatccct tatgggaact agacttacaa ccctatcaaa tgggctaaaa 1380
aacactttaa cggcaaccaa aagtggctta cataaagccg gtcaatcatt aacccaagcc 1440
ggcagttctt taaaaactgg ggcaaaaaaa attatcctct atattcccca aaattaccaa 1500
tatgatactg aacaaggtaa tggtttacag gatttagtca aagcggccga agagttgggg 1560
attgaggtac aaagagaaga acgcaataat attgcaacag ctcaaaccag tttaggcacg 1620
attcaaaccg ctattggctt aactgagcgt ggcattgtgt tatccgctcc acaaattgat 1680
aaattgctac agaaaactaa agcaggccaa gcattaggtt ctgccgaaag cattgtacaa 1740
aatgcaaata aagccaaaac tgtattatct ggcattcaat ctatttttagg ctcagttattg 1800
gctggaatgg atttagatga ggcctttcag aataacagca accaacatgc tcttgctaaa 1860
gctggcttga agctaacaaa ttcattaatt gaaaatattg ctaattcagt aaaaaacactt 1920
gacgaatttg gtgagcaaat tagtcaattt ggttcaaaac tacaaaaatat caaaggctta 1980
gggactttag gagacaaact caaaaatatc ggtggacttg ataaagctgg ccttggttta 2040
gatgttatct cagggctatt atcgggcgca acagctgcac ttgtacttgc agataaaaat 2100
gcttcaacag ctaaaaaagt gggtgcgggt tttgaattgg caaaccaagt tgttggtaat 2160
attaccaaag ccgtttcttc ttacatttta gcccaacgtg ttgcagcagg tttatcttca 2220
actgggcctg tggctgcttt aattgcttct actgtttctc ttgcgattag cccattagca 2280
tttgccggta ttgccgataa atttaatcat gcaaaaagtt tagagagtta tgccgaacgc 2340
tttaaaaaat taggctatga cggagataat ttattagcag aatatcagcg gggaacaggg 2400
actattgatg catcggttac tgcaattaat accgcattgg ccgctattgc tggtggtgtg 2460
tctgctgctg cagccggctc ggttattgct tcaccgattg ccttattagt atctgggatt 2520
accggtgtaa tttctacgat tctgcaatat tctaaacaag caatgtttga gcacgttgca 2580
aataaaattc ataacaaaat tgtagaatgg gaaaaaaata tcacggtaa gaactacttt 2640
gaaaatggtt acgatgcccg ttatcttgcg aatttacaag ataatatgaa attcttactg 2700
aacttaaaca aagagttaca ggcagaacgt gtcatcgcta ttactcagca gcaatgggat 2760
aacaacattg tgatttagc tggtattagc cgtttaggtg aaaaagtcct tagtggtaaa 2820
gcctatgtgg atgcgtttga agaaggcaaa cacattaaag ccgataaatt agtacagttg 2880
gattcggcaa acgtattat tgatgtgagt aattcggta aagcgaaaac tcagcatatc 2940
ttattcagaa cgccattatt gacgccggga acagagcagt gtgaacgcgt acaaacaggt 3000
aaatatgaat atattaccaa gctcaatatt aaccgtgtag atagctggaa attacagat 3060
ggtgcagcaa gttctacctt tgatttaact aacgttgttc agcgtattgg tattgaatta 3120
gacaatgctg gaaatgtaac taaaaccaaa gaaacaaaaa ttattgccaa acttggtgaa 3180
ggtgatgaca acgtatttgt tggttctggt acgacgaaa ttgatggcgg tgaaggttac 3240
gaccgagttc actatagccg tggaaactat ggtgctttaa ctattgatgc aaccaaagag 3300
accgagcaag gtagttatac cgtaaatcgt ttcgtagaaa ccggtaaagc actacacgaa 3360
gtgacttcaa cccataccgc attagtgggc aaccgtgaag aaaaaatagaa atatcgtcat 3420
agcaataacc agcaccatgc cggttattac accaaagata ccttgaaagc tgttgaagaa 3480
attatcggta catcacataa cgatatcttt aaaggtagta agttcaatga tgcctttaac 3540
ggtggtgatg gtgtcgatac tattgacggt aacgacggca atgaccgctt atttggtggt 3600
aaaggcgatg atattctcga tggtggaaat ggtgatgatt ttatcgatgg cggtaaaggc 3660
aacgacctat tacacggtgg caagggcgat gatattttcg ttcaccgtaa aggcgatggt 3720
aatgatatta ttaccgattc tgacggcaat gataaattat cattctctga ttcgaactta 3780
aaagatttaa catttgaaaa agttaaacat aatcttgtca tcacgaatag caaaaaagag 3840
aaagtgacca ttcaaaactg gttccgagag ctgattttg ctaagaagt gcctaattat 3900
aaagcaacta aagatgagaa aatgaagaa atcatcggtc aaatggcga gcggatcacc 3960
tcaaagcaag ttgatgatct tatcgcaaaa ggtaacggca aaattaccca agatgagcca 4020
tcaaaagttg ttgataacta tgaattgctc aaacatagca aaaatgtgac aaacagctta 4080
gataagttaa tctcatctgt aagtgcattt acctcgtcta atgattcgag aaatgtatta 4140
gtggctccaa cttcaatgtt ggatcaaagt ttatcttctc ttcaatttgc tagagcagct 4200
taatttttaa tgattggcaa ctctatattg tttcacacat tatagagttg ccgtttttatt 4260
```

```
ttataaaagg agacaatatg gaagctaacc atcaaaggaa tgatcttggt ttagttgccc    4320
tcactatgtt ggcacaatac cataatattt cgcttaatcc ggaa                    4364

SEQ ID NO: 2           moltype = DNA   length = 839
FEATURE                Location/Qualifiers
source                 1..839
                       mol_type = other DNA
                       organism = synthetic construct
SEQUENCE: 2
ggatccttta acggtggtga tggtgtcgat actattgacg gtaacgacgg caatgaccgc     60
ttatttggtg gtaaaggcga tgatattctc gatggtggaa atggtgatga ttttatcgat    120
ggcggtaaag gcaacgacct attacacggt ggcaagggcg atgatatttt cgttcaccgt    180
aaaggcgatg gtaatgatat tattaccgat tctgacggca atgataaatt atcattctct    240
gattcgaact taaaagattt aacatttgaa aaagttaaac ataatcttgc catcacgaat    300
agcaaaaaag agaaagtgac cattcaaaac tggttccgag aggctgattt tgctaaagaa    360
gtgcctaatt ataaagcaac taagatgagc aaaatcgaaa aatcatcgg tcaaaatggc    420
gagcggatca cctcaaagca agttgatgat cttatcgcaa aaggtaacgg caaaattacc    480
caagatgagc tatcaaagt tgttgataac atgaattgc tcaaacatag caaaaatgtg    540
acaaacagct tagataagtt aatctcatct gtaagtgcat ttacctcgtc taatgattcg    600
agaaatgtat tagtggctcc aacttcaatg ttggatcaaa gtttatcttc tcttcaattt    660
gctagagcag cttaattttt aatgattggc aactctatat tgtttcacac attatagagt    720
tgccgttta ttttataaaa ggagacaata tggaagctaa ccatcaaagg aatgatcttg    780
gtttagttgc cctcactatg ttggcacaat accataatat ttcgcttaat ccggaattc    839

SEQ ID NO: 3           moltype = DNA   length = 24
FEATURE                Location/Qualifiers
source                 1..24
                       mol_type = other DNA
                       organism = synthetic construct
SEQUENCE: 3
aaaggatcct ttaacggtgg tgat                                            24

SEQ ID NO: 4           moltype = DNA   length = 37
FEATURE                Location/Qualifiers
source                 1..37
                       mol_type = other DNA
                       organism = synthetic construct
SEQUENCE: 4
aaagaattcc ggattaagcg aaatattatg gtattgt                              37

SEQ ID NO: 5           moltype = DNA   length = 1076
FEATURE                Location/Qualifiers
source                 1..1076
                       mol_type = other DNA
                       organism = synthetic construct
SEQUENCE: 5
ggatccgaat tctcttttgc taaatagtgt tggtaagtag tcccattttg cacaccaatc     60
gttttcacct tagcaaaatc tgtatctttt ttcgcaatga aggcagcaga gcttggaaag    120
taaggctcgc taaataatac ttgtttctta cgtggttccg taatacccat acctgaaatt    180
gcagcatcaa attgttttg ttttaggctt tggattaagc tatcaaaagg ttggctatgg    240
aatgtacaat ttgcattcat ctctttacag atagcctttt gcaatatcca atcaaaaccg    300
ataatttctc ccttctcttc ggtcatttca aatggaggat agcttggctc catcacaaat    360
ttgatatctt gtgcctgcgc agtaaccaca caccgaata aaagggtcaa aagtgttttt    420
tcataaaaa gtccctgtgt tttcattata aggattacca ctttaacgca gttactttct    480
taaaaaagt cttcttttca taaagtttgt tttatgtcat acaaacacat caaattgaga    540
tgtagtttct caatcctctt gattcctcta tctcaaaaaa acaacccaaa agaaaaaaga    600
aaagtatatg ttacattaat attacaatgt aattattttg tttaatttcc ctacattttg    660
tataacttta aaacactcct ttttctcttc tgattatata aagacaaaaa atacaattt    720
aagctacaaa aaacaacaaa aacaacaaa aaacacgaca ataagatcga gtaattatta    780
tattatgtta taatttttga cctaatttag aataattata ggagacatcc cttatgcaat    840
tggtaattac aaatagcaaa aagaaaaag taacaattca aaattggttt cgtgaagcag    900
atttcgctaa agaagttcca aattataaag caacgaagga tgaaaaaatt gaagaaatta    960
ttggacaaaa tggagaacgt attacaagta aacaagtaga tgcttaatc gcaaaaggta   1020
acggaaaaat tactcaggat gaattatcga aggtggtaga taactatgaa ggatcc        1076

SEQ ID NO: 6           moltype = DNA   length = 810
FEATURE                Location/Qualifiers
source                 1..810
                       mol_type = other DNA
                       organism = synthetic construct
SEQUENCE: 6
ttctctttg ctaaatagtg ttggtaagta gtcccatttt gcacaccaat cgttttcacc      60
ttagcaaaat ctgtatcttt tttcgcaatg aaggcagcag agcttggaaa gtaaggctcg    120
ctaaataata cttgtttctt acgtggttcc gtaatacccat acctgaaatt gcagcatca    180
aattgttttg ttttaggctt tggattaag ctatcaaaag gttggctatg gaatgtacaa    240
tttgcattca tctctttaca gatagccttt gcaatatcca catcaaaacc gataatttct    300
cccttctctt cggtcatttc aaatggagga tagcttggct ccatcacaaa tttgatatct    360
tgtgcctgcg cagtaaccac acaccgaat aaaagggtca aagtgttttt ttcataaaa    420
agtccctgtg ttttcattat aaggattacc actttaacgc agttactttc ttaaaaaag    480
```

```
tcttcttttc ataaagtttg ttttatgtca tacaaacaca tcaaattgag atgtagtttc    540
tcaatcctct tgattcctct atctcaaaaa aacaacccaa aagaaaaaag aaaagtatat    600
gttacattaa tattacaatg taattatttt gtttaatttc cctacatttt gtataacttt    660
aaaacactcc tttttctctt ctgattatat aaaagacaaa aaatacaatt taagctacaa    720
aaaacaacaa aaaacaacaa aaaacacgac aataagatcg agtaatgatt atattatgtt    780
ataattttg  acctaattta gaataattat                                    810

SEQ ID NO: 7              moltype = DNA   length = 15
FEATURE                   Location/Qualifiers
source                    1..15
                          mol_type = other DNA
                          organism = synthetic construct
SEQUENCE: 7
aaggagacat ccctt                                                    15

SEQ ID NO: 8              moltype = DNA   length = 234
FEATURE                   Location/Qualifiers
source                    1..234
                          mol_type = other DNA
                          organism = synthetic construct
SEQUENCE: 8
caattggtaa ttacaaatag caaaaaagaa aaagtaacaa ttcaaaattg gtttcgtgaa    60
gcagatttcg ctaaagaagt tccaaattat aaagcaacga aggatgaaaa aattgaagaa    120
attattggac aaaatggaga acgtattaca agtaaacaag tagatgactt aatcgcaaaa    180
ggtaacggaa aaattactca ggatgaatta tcgaaggtgg tagataacta tgaa          234

SEQ ID NO: 9              moltype = AA    length = 80
FEATURE                   Location/Qualifiers
source                    1..80
                          mol_type = protein
                          organism = synthetic construct
SEQUENCE: 9
QLVITNSKKE KVTIQNWFRE ADFAKEVPNY KATKDEKIEE IIGQNGERIT SKQVDDLIAK    60
GNGKITQDEL SKVVDNYEGS                                               80

SEQ ID NO: 10             moltype = DNA   length = 832
FEATURE                   Location/Qualifiers
source                    1..832
                          mol_type = other DNA
                          organism = Mannheimia haemolytica
SEQUENCE: 10
cctttaacgg tggtgatggt gtcgatacta ttgacggtaa cgacggcaat gaccgcttat    60
ttggtggtaa aggcgatgat attctcgatg gtggaaatgg tgatgatttt atcgatgggc    120
gtaaaggcaa cgacctatta cacggtggca agggcgatga tatttttcgtt caccgtaaag    180
gcgatggtaa tgatattatt accgattctg acggcaatga taattatca ttctctgatt    240
cgaacttaaa agatttaaca tttgaaaaag ttaaacataa tcttgtcatc acgaatagca    300
aaaagagaa agtgaccatt caaaactggt tccgagagcc tgattttgct aaagaagtgc    360
ctaattataa agcaactaaa gatgagaaaa tcgaagaaat catcggtcaa aatggcgagc    420
ggatcacctc aaagcaagtt gatgatctta tcgcaaaagg taacggcaaa attacccaag    480
atgagctatc aaaagttgtt gataactatg aattgctcaa acatagcaaa aatgtgacaa    540
acagcttaga taagttaatc tcatctgtaa gtgcatttac ctcgtctaat gattcgagaa    600
atgtattagt ggctccaact tcaatgttgg atcaaagtttt atcttctctt caatttgcta    660
gagcagctta attttaatg attggcaact ctatattgtt tcacacatta tagagttgcc    720
gttttatttt ataaaggag acaatatgga agctaaccat caaaggaatg atcttggttt    780
agttgccctc actatgttgg cacaatacca taatatttcg cttaatccgg aa           832

SEQ ID NO: 11             moltype = AA    length = 282
FEATURE                   Location/Qualifiers
source                    1..282
                          mol_type = protein
                          organism = Mannheimia haemolytica
SEQUENCE: 11
ELVITNSKKE KVTIQNWFRE ADFAKEVPNY KATKDEKIEE IIGQNGERIT SKQVDDLIAK    60
GNGKITQDEL SKVVDNYEGS FNGGDGVDTI DGNDGNDRLF GGKGDDILDG GNGDDFIDGG    120
KGNDLLHGGK GDDIFVHRKG DVKDLTFEKV KHNLVITNSK KEKVTIQNWF READFAKEVP    180
NYKATKDEKI EEIIGQNGER ITSKQVDDLI AKGNGKITQD ELSKVVDNYE LLKHSKNVTN    240
SLDKLISSVS AFTSSNDSRN VLVAPTSMLD QSLSSLQFAR AA                      282

SEQ ID NO: 12             moltype = DNA   length = 1903
FEATURE                   Location/Qualifiers
source                    1..1903
                          mol_type = other DNA
                          organism = synthetic construct
SEQUENCE: 12
gaattctctt tgctaaaata gtgttggtaa gtagtcccat tttgcacacc aatcgttttc    60
acctagcaa atctgtatc ttttttcgca atgaaggcag cagagcttgg aaagtaaggc    120
tcgctaaata tacttgttt cttacgtggt tccgtaatac ccatacctga aattgcagca    180
tcaaattgtt tttgttttag ctttggatt aagctatcaa aaggttggct atggaatgta    240
caatttgcat tcatctctttt acagatagca tttgcaatat ccacatcaaa accgataatt    300
```

-continued

```
tctcccttct cttcggtcat ttcaaatgga ggatagcttg gctccatcac aaatttgata  360
tcttgtgcct gcgcagtaac cacacacccg aataaaaggg tcaaaagtgt ttttttcata  420
aaaagtccct gtgttttcat tataaggatt accactttaa cgcagttact ttcttaaaaa  480
aagtcttctt ttcataaagt ttgttttatg tcatacaaac acatcaaatt gagatgtagt  540
ttctcaatcc tcttgattcc tctatctcaa aaaaacaacc caaaagaaaa aagaaaagta  600
tatgttacat taatattaca atgtaattat tttgttaat ttccctacat tttgtataac  660
tttaaaacac tccttttct cttctgatta tataaaagac aaaaaatca atttaagcta  720
caaaaaacaa caaaaaacaa caaaaaacac gacaataaga tcgagtaatg attatatat  780
gttataattt ttgacctaat ttagaataat tataggagac atcccttatg caattggtaa  840
ttacaaatag caaaaaagaa aaagtaacaa ttcaaaattg gtttcgtgaa gcagatttcg  900
ctaaagaagt tccaaattat aaagcaacga aggatgaaaa aattgaagaa attattggac  960
aaaatggaga acgtattaca agtaaacaag tagatgactt aatcgcaaaa ggtaacggaa 1020
aaattactca ggatgaatta tcgaaggtgg tagataacta tgaaggatcc tttaacggtg 1080
gtgatggtgt cgatactatt gacggtaacg acggcaatga ccgcttattt ggtggtaaag 1140
gcgatgatat tctcgatggt ggaaatggtg atgatttat cgatggcggt aaaggcaacg 1200
acctattaca cggtggcaag ggcgatgata ttttcgttca ccgtaaaggc gatggtaatg 1260
atattattac cgattctgac ggcaatgata aattatcatt ctctgattcg aacttaaaag 1320
atttaacatt tgaaaaagtt aaacataatc ttgtcatcaa atagcaaa aaagagaaaa 1380
tgaccattca aaactggttc cgagaggctg attttgctaa agaagtgcct aattataaag 1440
caactaaaga tgagaaaatc gaagaaatca tcggtcaaaa tggcgagcgg atcacctcaa 1500
agcaagttga tgatcttatc gcaaaaggta acggcaaaat tacccaagat gagctatcaa 1560
aagttgttga taactatgaa ttgctcaaac atagcaaaaa tgtgacaaac agcttagata 1620
agttaatctc atctgtaagt gcatttacct cgtctaatga ttcgagaaat gtattagtgg 1680
ctccaacttc aatgttggat caagttttat cttctcttca atttgctaga gcagcttaat 1740
ttttaatgat tggcaactct atattgtttc acacattata gagttgccgt tttattttat 1800
aaaaggagac aatatggaag ctaaccatca aggaatgatg cttggtttag ttgccctcac 1860
tatgttggca caataccata atatttcgct taatccggaa ttc                   1903

SEQ ID NO: 13            moltype = AA  length = 303
FEATURE                  Location/Qualifiers
source                   1..303
                         mol_type = protein
                         organism = synthetic construct
SEQUENCE: 13
MQLVITNSKK EKVTIQNWFR EADFAKEVPN YKATKDEKIE EIIGQNGERI TSKQVDDLIA  60
KGNGKITQDE LSKVVDNYEG SFNGGDGVDT IDGNDGNDRL FGGKGDDILD GGNGDDFIDG 120
GKGNDLLHGG KGDIFVHRK GDGNDIITDS DGNDKLSFSD SNLKDLTFEK VKHNLVITNS 180
KKEKVTIQNW FREADFAKEV PNYKATKDEK IEEIIGQNGE RITSKQVDDL IAKGNGKITQ 240
DELSKVVDNY ELLKHSKNVT NSLDKLISSV SAFTSSNDSR NVLVAPTSML DQSLSSLQFA 300
RAA                                                              303

SEQ ID NO: 14            moltype = DNA  length = 606
FEATURE                  Location/Qualifiers
source                   1..606
                         mol_type = other DNA
                         organism = synthetic construct
SEQUENCE: 14
atgaacgcgg tcgatacatg gattgagaca cctgttaaag atttcgagaa accgttctta  60
atggcggtag aagacgtgtt tacaatttca ggtcgtggca ccgttgcaac aggtcgtgta 120
gaacgtggac gcttaagttt aaatgaggaa gtggagattg taggtttaaa gcccactaaa 180
aaaacagtcg ttacaggtat cgaaatgttt cgcaaaaact taaagaaagc ccaagcagga 240
gataacgcag gtttattatt acgtggagtt gaacgcagtg ccattgaacg tggtcaagta 300
ttagcaaaac cagggagtat cgttcctcat gccgaatttg aagccgccat ttatgcattg 360
acaaaagaag aaggcggacg tcatactccg tttttcgtaa actataaacc tcaatttat 420
ttccgtacaa cagatgtgac tggtggcctt gagtttgaga aaggacgtga atttgtacaa 480
ccgggagaaa atgtcaactt gaaagtaaaa ttaattgcac caatcgccgt aggaggaa 540
acaaaattca gtattcgtga aggtgggcgc acagtagggt atggtagtgt aactaaaatt 600
ttaaag                                                            606

SEQ ID NO: 15            moltype = AA  length = 202
FEATURE                  Location/Qualifiers
source                   1..202
                         mol_type = protein
                         organism = synthetic construct
SEQUENCE: 15
MNAVDTWIET PVKDFEKPFL MAVEDVFTIS GRGTVATGRV ERGRLSLNEE VEIVGLKPTK  60
KTVVTGIEMF RKNLKEAQAG DNAGLLLRGV ERSAIERGQV LAKPGSIVPH AEFEAAIYAL 120
TKEEGGRHTP FFVNYKPQFY FRTTDVTGGL EFEKGREFVQ PGENVNLKVK LIAPIAVEEG 180
TKFSIREGGR TVGYGSVTKI LK                                         202

SEQ ID NO: 16            moltype = DNA  length = 683
FEATURE                  Location/Qualifiers
source                   1..683
                         mol_type = other DNA
                         organism = synthetic construct
SEQUENCE: 16
ttagtcgatg taacccccttt aactttaggt attgaaacag caggcggcat tgcaacccct  60
ttaatcccac gtaacactcg tattcccatt acaaagtcag aagttttac aacgtttgaa 120
gataaccaaa gtgaagtaac aattcgtatc gtgcaaggtg aacgtccatt agcgtctgaa 180
```

```
aataaattat taggacaatt taacttaggt ggaatccgta tcgcaccccg tggagtacct    240
caaatcgaag tcagtttcaa aatcgatgca aacggcatta cgacagtatt agcaaaagat    300
aaagatacca acaaagaaca atctattaca attaaaaaca gctctaaatt aagtgacgca    360
gaaatcgaag aaatgatcaa agatgcagaa aaaaaccgtg aagcagatgc caaacgtgcc    420
gaagaaatta gtacaattat tcaagcagaa aacttagtaa actcattaga aaaagaaatg    480
aacgaaggta acattgtaat tccagaagaa gaaaaaacta aaatcgccga atatattaaa    540
gaagtaaaag agttaatcaa caataaagat gtagaacaat taaaaaagaa aattgatgaa    600
ttaaacgcag catataatat ggccaaatca gcagcagcct cagcaaataa agatgatagt    660
agtaattcgg atgaagaaac ttc                                             683

SEQ ID NO: 17            moltype = AA   length = 228
FEATURE                  Location/Qualifiers
source                   1..228
                         mol_type = protein
                         organism = Mycoplasma bovis
SEQUENCE: 17
LVDVTPLTLG IETAGGIATP LIPRNTRIPI TKSEVFTTFE DNQSEVTIRI VQGERPLASE     60
NKLLGQFNLG GIRIAPRGVP QIEVSFKIDA NGITTVLAKD KDTNKEQSIT IKNSSKLSDA    120
EIEEMIKDAE KNREADAKRA EEISTIIQAE NLVNSLEKEM NEGNIVIPEE EKTKIAEYIK    180
EVKELINNKD VEQLKKKIDE LNAAYNMAKS AAASANKDDS SNSDEETF                 228

SEQ ID NO: 18            moltype = DNA   length = 1302
FEATURE                  Location/Qualifiers
source                   1..1302
                         mol_type = other DNA
                         organism = synthetic construct
SEQUENCE: 18
caattgatga acgcggtcga tacatggatt gagacacctg ttaaagattt cgagaaaccg     60
ttcttaatgg cggtagaaga cgtgtttaca atttcaggtc gtggcaccgt tgcaacaggt    120
cgtgtagaac gtggacgctt aagtttaaat gaggaagtgg agattgtagg tttaaagccc    180
actaaaaaaa cagtcgttac aggtatcgaa atgtttcgca aaaacttaaa agaagcccaa    240
gcaggagata acgcaggttt attattacgt ggagttgaac gcagtgccat tgaacgtggt    300
caagtattag caaaaccagg gagtatcgtt ccctcatgccg aatttgaagc cgccattttat    360
gcattgacaa aagaagaagg cggacgtcat actccgtttt tcgtaaacta taaacctaca    420
ttttatttcc gtacaacaga tgtgactggt ggccttgagt ttgagaaagg acgtgaattt    480
gtacaaccgg gagaaaatgt caacttgaaa gtaaaattaa ttgcaccaat cgccgtagag    540
gaaggaacaa aattcagtat tcgtgaaggt gggcgcacag tagggtatgg tagtgtaact    600
aaaatttttaa agttagtcga tgtaaccccct ttaactttag gtattgaaac agcaggcggc    660
attgcaaccc ctttaatccc acgtaacact cgtattccca ttacaaagtc agaagttttt    720
acaacgtttg aagataacca aagtgaagta acaattcgta tcgtgcaagg tgaacgtcca    780
ttagcgtctg aaaataaatt attaggacaa tttaacttag gtggaatccg tatcgcaccc    840
cgtggagtac tcaaaatcga agtcagtttc aaaatcgatg caaacggcat tacgacagta    900
ttagcaaaag ataaagatac caacaaagaa caatctaaaa cgctctcaa                 960
ttaagtgacg cagaaatcga gaaaatgatc aaagatgcag aaaaaaaccg tgaagcagat    1020
gccaaacgtg ccgaagaaat tagtacaatt attcaagcag aaaacttagt aaactcatta    1080
gaaaaagaaa tgaacgaagg taacattgta attccagaag aagaaaaaac taaaatcgcc    1140
gaatatatta aagaagtaaa agagttaatc aacaataaag atgtagaaca attaaaaaag    1200
aaaattgatg aattaaacgc agcatataat atggccaaat cagcagcagc ctcagcaaat    1260
aaagatgata gtagtaattc ggatgaagaa actttcgaat tc                       1302

SEQ ID NO: 19            moltype = AA   length = 434
FEATURE                  Location/Qualifiers
source                   1..434
                         mol_type = protein
                         organism = synthetic construct
SEQUENCE: 19
QLMNAVDTWI ETPVKDFEKP FLMAVEDVFT ISGRGTVATG RVERGRLSLN EEVEIVGLKP     60
TKKTVVTGIE MFRKNLKEAQ AGDNAGLLLR GVERSAIERG QVLAKPGSIV PHAEFEAAIY    120
ALTKEEGGRH TPFFVNYKPQ FYFRTTDVTG GLEFEKGREF VQPGENVNLK VKLIAPIAVE    180
EGTKFSIREG GRTVGYGSVT KILKLVDVTP TLTLGIETAGG IATPLIPRNT RIPITKSEVF    240
TTFEDNQSEV TIRIVQGERP LASENKLLGQ FNLGGIRIAP RGVPQIEVSF KIDANGITTV    300
LAKDKDTNKE QSITIKNSSK LSDAEIEEMI KDAEKNREAD AKRAEEISTI IQAENLVNSL    360
EKEMNEGNIV IPEEEKTKIA EYIKEVKELI NNKDVEQLKK KIDELNAAYN MAKSAAASAN    420
KDDSSNSDEE TFEF                                                      434

SEQ ID NO: 20            moltype = DNA   length = 3205
FEATURE                  Location/Qualifiers
source                   1..3205
                         mol_type = other DNA
                         organism = synthetic construct
SEQUENCE: 20
ggatccgaat tctcttttgc taaatagtgt tggtaagtag tcccattttg cacaccaatc     60
gttttcacct tagcaaaatc tgtatctttt ttcgcaatga aggcagcaga gcttggaaag    120
taaggctcgc taaatataac ttgtttctta cgtggttccg taatacccat acctgaaatt    180
gcagcatcaa attgttttttg ttttaggctt tggattaagc tatcaaaagg ttggctatgg    240
aatgtacaat ttgcattcat ctctttacag atagcatttg caatatccac atcaaaaccg    300
ataatttctc cttctcttc ggtcatttca aatggaggat agcttggctc catcacaaat    360
ttgatatctt gtgcctgcgc agtaaccaca cacccgaata aaagggtcaa aagtgttttt    420
tcataaaaaa gtccctgtgt tttcattata aggattacca ctttaacgca gttactttct    480
```

```
taaaaaaagt cttcttttca taaagtttgt tttatgtcat acaaacacat caaattgaga    540
tgtagtttct caatcctctt gattcctcta tctcaaaaaa acaacccaaa agaaaaaaga    600
aaagtatatg ttacattaat attacaatgt aattattttg tttaatttcc ctacatttg     660
tataacttta aaacactcct ttttctcttc tgattatata aagacaaaaa aatacaattt    720
aagctacaaa aaacaacaaa aaacaacaaa aaacacgaca ataagatcga gtaatgatta    780
tattatgtta aattttttga cctaatttag aataattata ggagacatcc cttatgcaat    840
tgatgaacgc ggtcgataca tggattgaga cacctgttaa agatttcgag aaaccgttct    900
taatggcggt agaagacgtg tttacaattt caggtcgtgg caccgttgca acaggtcgtg    960
tagaacgtgg acgcttaagt ttaaatgagg aagtggagat tgtaggttta aagcccacta   1020
aaaaaacagt cgttacaggt atcgaaatgt ttcgcaaaaa cttaaaagaa gcccaagcag   1080
gagataacgc aggtttatta ttacgtggag ttgaacgcag tgccattgaa cgtggtcaag   1140
tattagcaaa accagggagt atcgttcctc atgccgaatt tgaagccgcc atttatgcat   1200
tgacaaaaga agaaggcgga cgtcatactc cgttttttcgt aaactataaa cctcaatttt  1260
atttccgtac aacagatgtg actggtggcc ttgagtttga gaaaggacgt gaatttgtac   1320
aaccgggaga aaatgtcaac ttgaaagtaa aattaattgc accaatcgcc gtagaggaag   1380
gaacaaaatt cagtattcgt gaaggtgggc gcacagtagg gtatggtagt gtaactaaaa   1440
ttttaaagtt agtcgatgta acccctttaa cttaggtat tgaaacagca ggcggcattg    1500
caacccctt aatcccacgt aacactcgta ttcccattac aaagtcagaa gttttacaa    1560
cgtttgaaga taaccaaagt gaagtaacaa ttcgtatcgt gcaaggtgaa cgtccattag   1620
cgtctgaaaa taaattatta ggacaattta acttaggtgg aatccgtatc gcaccccgtg   1680
gagtacctca aatcgaagtc agtttcaaaa tcgatgcaaa cggcattacg acagtattag   1740
caaaagataa agataccaac aaagaacaat ctattacaat taaaaacagc tctaaattaa   1800
gtgacgcaga atcgaagaa atgatcaaag atgcagaaaa aaaccgtgaa gcagatgcca   1860
aacgtgccga agaaattagt acaattattc aagcagaaaa cttagtaaac tcattagaaa   1920
aagaaatgaa cgaaggtaac attgtaattc cagaagaaga aaaaactaaa atcgccgaat   1980
atattaaaga agtaaaagag ttaatcaaca ataaagatgt agaacaatta aaaaagaaaa   2040
ttgatgaatt aaacgcagca tataatatgg ccaaatcagc agcagcctca gcaaataaag   2100
atgatagtag taattcggat gaagaaactt tcgaattggt aattacaaat agcaaaaaag   2160
aaaaagtaac aattcaaaat tggtttcgtg aagcagattt cgctaaagaa gttccaaatt   2220
ataaagcaac gaaggatgaa aaaattgaag aaattattgg acaaaatgga gaacgtataa   2280
caagtaaaca agtagatgac ttaatcgcaa aaggtaacgg aaaaattact caggatgaat   2340
tatcgaaggt ggtagataac tatgaaggat ccttaaacgg tggtgatggt gtcgatacta   2400
ttgacggtaa cgacggcaat gaccgcttat ttggtggtaa aggcgatgat attctcgatg   2460
gtggaaatgg tgatgatttt atcgatgcg gtaaaggcaa cgacctatta cacggtggca   2520
agggcgatga tatttttgtt caccgtaaag gcgatgtaa tgatattatt accgattctg   2580
acggcaatga taaattatca ttctctgatt cgaacttaaa agatttaaca tttgaaaaag   2640
ttaaacataa tcttgtcatc acgaatagca aaaaagagaa agtgaccatt caaaactggt   2700
tccgagaggc tgatttgct aaagaagtgc ctaattataa agcaactaaa gatgagaaaa   2760
tcgaagaaat catcggtcaa aatggcgagc ggatcacctc aaagcaagtt gatgatctca   2820
tcgcaaaagg taacggcaaa attcccaag atgagctatc aaaagttgtt gataactatg   2880
aattgctcaa acatagcaaa aatgtgacaa acagcttaga taagtaaatc tcatctgtaa   2940
gtgcatttac ctcgtctaat gattcagaaa atgtattagt ggctccaact tcaatgttgg   3000
atcaaagttt atcttctctt caatttgcta gagcagctta attttaatg attggcaatt   3060
ctatattgtt tcacacatta tagagttgcc gttttatttt ataaaaggag acaatatga    3120
agctaaccat caaaggaatg atcttggttt agttgccctc actatgttgg cacaatacca   3180
taatatttcg cttaatccgg aattc                                          3205

SEQ ID NO: 21         moltype = AA   length = 735
FEATURE               Location/Qualifiers
source                1..735
                      mol_type = protein
                      organism = synthetic construct
SEQUENCE: 21
MQLMNAVDTW IETPVKDFEK PFLMAVEDVF TISGRGTVAT GRVERGRLSL NEEVEIVGLK    60
PTKKTVVTGI EMFRKNLKEA QAGDNAGLLL RGVERSAIER VQVLAKPGSI VPHAEFEAAI   120
YALTKEEGGR HTPFFVNYKP QFYFRTTDVT GGLEFEKGRE FVQPGENVNL KVKLIAPIAV   180
EEGTKFSIRE GGRTVGYGSV TKILKLVDVT PLTLGIETAG GIATPLIPRN TRIPITKSEV   240
FTTFEDNQSE VTIRIVQGER PLASENKLLG QFNLGGIRIA PRGVPQIEVS FKIDANGITT   300
VLAKDKDTNK EQSITIKNSS KLSDAEIEEM IKDAEKNREA DAKRAEEIST IIQAENLVNS   360
LEKEMNEGNI VIPEEEKTKI AEYIKEVKEL INNKDVEQLK KKIDELNAAY NMAKSAAASA   420
NKDDSSNSDE ETFELVITNS KKEKVTIQNW FREADFAKEV PNYKATKDEK IEEIIGQNGE   480
RITSKQVDDL IAKGNGKITQ DELSKVVDNY EGSFNGGDGV DTIDGNDGND RLFGGKGDDI   540
LDGGNGDDFI DGGKGNDLLH GGKGDDIFVH RKGDGNDIIT DSDGNDKLSF SDSNLKDLTF   600
EKVKHNLVIT NSKKEKVTIQ NWFREADFAK EVPNYKATKD EKIEEIIGQN GERITSKQVD   660
DLIAKGNGKI TQDELSKVVD NYELLKHSKN VTNSLDKLIS SVSAFTSSND SRNVLVAPTS   720
MLDQSLSSLQ FARAA                                                    735

SEQ ID NO: 22         moltype = DNA   length = 23
FEATURE               Location/Qualifiers
source                1..23
                      mol_type = other DNA
                      organism = synthetic construct
SEQUENCE: 22
gttctcaatc ctcttgattc ctc                                            23

SEQ ID NO: 23         moltype = DNA   length = 24
FEATURE               Location/Qualifiers
source                1..24
                      mol_type = other DNA
```

```
                    organism = synthetic construct
SEQUENCE: 23
gttaccgtca atagtatcga cacc                                          24

SEQ ID NO: 24       moltype = DNA  length = 24
FEATURE             Location/Qualifiers
source              1..24
                    mol_type = other DNA
                    organism = synthetic construct
SEQUENCE: 24
ggagaaaatg tcaacttgaa agta                                          24

SEQ ID NO: 25       moltype = DNA  length = 23
FEATURE             Location/Qualifiers
source              1..23
                    mol_type = other DNA
                    organism = synthetic construct
SEQUENCE: 25
ggattccacc taagttaaat tgt                                           23

SEQ ID NO: 26       moltype = DNA  length = 20
FEATURE             Location/Qualifiers
source              1..20
                    mol_type = other DNA
                    organism = synthetic construct
SEQUENCE: 26
acaccaaagc aacagactgc                                               20

SEQ ID NO: 27       moltype = DNA  length = 20
FEATURE             Location/Qualifiers
source              1..20
                    mol_type = other DNA
                    organism = synthetic construct
SEQUENCE: 27
cctgtaaagg catctgccca                                               20

SEQ ID NO: 28       moltype = DNA  length = 20
FEATURE             Location/Qualifiers
source              1..20
                    mol_type = other DNA
                    organism = synthetic construct
SEQUENCE: 28
ttggtgcttg ggagtatgcc                                               20

SEQ ID NO: 29       moltype = DNA  length = 20
FEATURE             Location/Qualifiers
source              1..20
                    mol_type = other DNA
                    organism = synthetic construct
SEQUENCE: 29
atcggaaacg gtttgctgga                                               20
```

MANNHEIMIA HAEMOLYTICA VECTOR

CROSS-REFERENCE TO RELATED APPLICATIONS

This application is a divisional of U.S. application Ser. No. 17/190,182, filed Mar. 2, 2021, now allowed, which claims priority to U.S. Provisional Patent Application No. 62/984,700, filed Mar. 3, 2020. The contents of these patent applications is hereby expressly incorporated by reference in their entirety.

FIELD OF THE INVENTION

The invention relates to modified *Mannheimia haemolytica* (*M. haemolytica*) lktCA gene cluster cassettes comprising an insertion of a polynucleotide encoding an additional *M. haemolytica* leukotoxin neutralizing epitope. Encompassed by the invention are also modified *M. haemolytica* lktCA gene cluster cassettes expressing a *Mycoplasma bovis* (*M. bovis*) antigen. The invention also concerns Compositions, vectors, and bacterial or fungal strains comprising such modified *M. haemolytica* lktCA gene cluster cassettes. Included in the invention are kits comprising such cassettes, compositions, vectors, and bacterial or fungal strains; and methods of vaccination using such cassettes, compositions, vectors, and bacterial or fungal strains.

SEQUENCE LISTING

The instant application contains a Sequence Listing XML required by 37 C.F.R. § 1.831(a) which has been submitted in XML file format via the USPTO patent electronic filing system, and is hereby incorporated by reference in its entirety. The XML file was created on May 1, 2023, is named Sequence Listing-005323.xml, and has 43.2 KB.

BACKGROUND OF THE INVENTION

*Mycoplasma bovis* (*M. bovis*) is an important pathogen associated with a relatively broad range of disease manifestations. Prominently due to *M. bovis*, pneumonia, otitis media, polyarthritis, and mastitis result in considerable economic losses to dairy, beef, and bison producers in the United States and abroad. *M. bovis* disease treatment with antimicrobials is often unrewarding, requiring early diagnosis and early drug delivery for efficacy. Yet symptoms of disease are often mild and slowly-progressing, resulting in considerable difficulty in diagnosis, and in treatment delays.

Management practices, including biosecurity, sanitation, and husbandry practices to reduce stress, appear to result in reduced disease losses. Vaccination with experimental or commercial vaccines to prevent *M. bovis*-associated disease has yielded mixed results. Some published trials have shown disease reduction among vaccinated animals, while others have shown no statistical protection. Anecdotally, vaccination with commercial products may result in meaningful reductions of polyarthritis and otitis media. Two *M. bovis* vaccine products, both bacterins (inactivated bacteria), are commercially available in the United States. No commercial *M. bovis* vaccine product appears to be currently available in the European Union.

Use of bacterial vectors as vehicles to deliver recombinant antigens emerged in the late 1990s. Bacteria-based antigen delivery vectors exhibit multiple advantages, such as the possibility to control its intrinsic infectious power, its non-integrative properties, ability to regulate the amount and in vivo localization of the antigen, a potential for multiple vaccine delivery routes, potent stimulation of the innate and adaptive immune systems, and relatively low manufacturing costs. Bacterial vectors most frequently used as vaccine vectors are *Listeria* and *Salmonella*.

U.S. Pat. No. 9,370,561, issued Jun. 21, 2016, discloses the modification of the *M. haemolytica* strain A1 lktCA gene cluster by an in-frame deletion of the nucleotides encoding amino acid 4 of lktC to the nucleotides encoding amino acid 707 of lktA, and replacement of the lktC ribosome binding site (rbs) with an *E. coli* consensus rbs. Electrocompetent *M. haemolytica* cells were transformed with the modified lktCA gene cluster resulting in attenuated bacterium. U.S. Pat. No. 9,370,561 claims a vaccine comprising live, attenuated *M. haemolytica* A1 and A6 strains containing nucleic acid deletions in their respective lktA genes, that provide protective immune response against disease caused by *M. haemolytica* strains A1 and A6.

U.S. Pat. No. 6,331,303, issued Dec. 18, 2001, discloses *P. haemolytica* bacterium which expresses no biologically active leukotoxin, expresses a leukotoxin molecule lacking amino acids 34 to 378, and contains no foreign DNA. In 1999, *P. haemolytica* was renamed as *Mannheimia haemolytica*.

Thus, new methods of controlling *M. bovis* disease are needed. Use of a modified *M. haemolytica* lktCA gene cluster cassette may expedite preparation of *M. bovis* vaccines for such control.

SUMMARY OF THE INVENTION

Provided herein is a modified *M. haemolytica* lktCA gene cluster cassette comprising a polynucleotide fragment encoding an additional leukotoxin neutralizing epitope. This modified *M. haemolytica* lktCA gene cluster cassette encodes two leukotoxin neutralizing epitopes, and is useful for the expression of bacterial or viral antigens. Provided herein is also an *M. bovis* antigen and a modified *M. haemolytica* lktCA gene cluster cassette comprising a polynucleotide fragment encoding an additional leukotoxin neutralizing epitope expressing an *M. bovis* antigen.

In an embodiment, the invention relates to a modified *M. haemolytica* lktCA gene cluster cassette comprising a polynucleotide encoding an additional leukotoxin neutralizing epitope inserted downstream of the native leukotoxin A start codon. In some embodiments of the invention, the modified *M. haemolytica* lktCA gene cluster cassette lacks the leukotoxin C ribosome binding site and coding region. In some embodiments of the invention, the modified *M. haemolytica* lktCA gene cluster cassette lacks leukotoxin A nucleotides encoding amino acids 2 to at least 710.

In some embodiments of the invention, the modified *M. haemolytica* lktCA gene cluster cassette comprises a native leukotoxin promotor polynucleotide fragment; a native leukotoxin A ribosome binding site and start codon polynucleotide fragment; the polynucleotide encoding the added leukotoxin neutralizing epitope; and a polynucleotide encoding at least leukotoxin A amino acids 732 to 953. In some embodiments of the invention, the modified *M. haemolytica* lktCA gene cluster cassette comprises a leukotoxin promotor polynucleotide; a leukotoxin A ribosome binding site and start codon polynucleotide; a polynucleotide encoding at least leukotoxin A amino acids 732 to 953; and a polynucleotide encoding the added leukotoxin neutralizing epitope. In some embodiments of the invention, the leukotoxin promotor polynucleotide; the leukotoxin A ribosome binding site and start codon polynucleotide; the polynucleotide encoding at least leukotoxin A amino acids 732 to 953; and the polynucleotide encoding the added leukotoxin neutralizing epitope are from *M. haemolytica* strain A1 or *M. haemolytica* strain A6 bacteria.

In some embodiments of the invention, in the modified *M. haemolytica* lktCA gene cluster cassette of the invention, the leukotoxin promotor has the nucleotide sequence set forth in SEQ ID NO: 6; the leukotoxin A ribosome binding site and start codon have the nucleotide sequence set forth in SEQ ID NO: 7; the added leukotoxin neutralizing epitope has the amino acid sequence set forth in SEQ ID NO: 9; the leukotoxin A amino acids 732 to 953 have the amino acid sequence set forth in SEQ ID NO: 11. In some embodiments of the invention, the polynucleotide encoding lktA amino acids 732 to 953 in the modified *M. haemolytica* lktCA gene cluster cassette has the nucleotide sequence set forth in SEQ ID NO: 10. In some embodiments of the invention, the modified *M. haemolytica* lktCA gene cluster cassette encodes an amino acid sequence as set forth in SEQ ID NO: 13.

In an embodiment, the invention relates to a composition comprising a modified *M. haemolytica* lktCA gene cluster cassette comprising a polynucleotide encoding an additional leukotoxin neutralizing epitope inserted downstream of the native leukotoxin A start codon, where the composition is a polynucleotide, a plasmid, an expression vector, a host cell, a vaccine, or an immunogenic composition. In some embodiments of the invention, the composition comprising the modified *M. haemolytica* lktCA gene cluster cassette is a replacement plasmid, an attenuated *M. haemolytica* strain A1 bacterium, or an attenuated *M. haemolytica* strain A6 bacterium. In some embodiments, the invention relates to a vaccine or immunogenic composition comprising the modified *M. haemolytica* lktCA gene cluster cassette as disclosed herein, and optionally an adjuvant.

In an embodiment, the invention relates to a modified *M. haemolytica* lktCA gene cluster cassette as disclosed herein further comprising a polynucleotide encoding at least one heterologous antigen. In some embodiments of the invention, the polynucleotide encoding at least one heterologous antigen is inserted upstream of the polynucleotide encoding the added leukotoxin neutralizing epitope. In some embodiments, the invention relates to a composition comprising the modified *M. haemolytica* lktCA gene cluster cassette as disclosed herein and further comprising a polynucleotide encoding at least one heterologous antigen. In some embodiments of the invention, the composition is a polynucleotide, a plasmid, an expression vector, a host cell, a vaccine, or an immunogenic composition. In some embodiments of the invention, the composition comprising the modified *M. haemolytica* lktCA gene cluster cassette as disclosed herein and encoding at least one heterologous antigen is a replacement plasmid, an attenuated *M. haemolytica* strain A1 bacterium, or an attenuated *M. haemolytica* strain A6 bacterium. In some embodiments, the invention relates to a vaccine or immunogenic composition comprising a composition comprising a modified *M. haemolytica* lktCA gene cluster cassette encoding at least one heterologous antigen, and optionally an adjuvant.

In an embodiment, the invention relates to an *M. bovis* antigen. In some embodiments of the invention, the *M. bovis* antigen is elongation factor thermo unstable protein (EF-Tu) or heat shock protein DnaK. In some embodiments of the invention, the *M. bovis* antigen comprises EF-Tu and DnaK. In some embodiments of the invention, the *M. bovis* antigen is a chimeric *M. bovis* antigen. In some embodiments of the invention, the chimeric *M. bovis* antigen comprises EF-Tu and DnaK. In some embodiments of the invention, the chimeric *M. bovis* antigen has the amino acid sequence set forth in SEQ ID NO: 19. In some embodiments, the invention relates to a composition comprising at least one *M. bovis* antigen. In some embodiments of the invention, the composition comprising at least one *M. bovis* antigen is a polynucleotide, a plasmid, an expression vector, a host cell, a vaccine, or an immunogenic composition. In some embodiments of the invention, the composition comprising at least one *M. bovis* antigen is a replacement plasmid, an attenuated *M. haemolytica* strain A1 bacterium, or an attenuated *M. haemolytica* strain A6 bacterium. In some embodiments of the invention, the composition comprising at least one *M. bovis* antigen further comprises an adjuvant. In some embodiments, the invention relates to a vaccine or immunogenic composition comprising at least one *M. bovis* antigen, and optionally an adjuvant.

In an embodiment, the invention relates to a modified *M. haemolytica* lktCA gene cluster cassette as disclosed herein, and further comprising a polynucleotide encoding at least one *M. bovis* antigen. In some embodiments of the invention, the polynucleotide encoding at least one *M. bovis* antigen inserted in the modified *M. haemolytica* lktCA gene cluster cassette encodes EF-Tu or DnaK. In some embodiments of the invention, the polynucleotide encoding at least one *M. bovis* antigen inserted in the modified *M. haemolytica* lktCA gene cluster cassette encodes EF-Tu and DnaK. In some embodiments of the invention, the polynucleotide encoding at least one *M. bovis* antigen inserted in the modified *M. haemolytica* lktCA gene cluster cassette is a polynucleotide encoding a chimeric *M. bovis* antigen. In some embodiments of the invention, the polynucleotide encoding a chimeric *M. bovis* antigen inserted in the modified *M. haemolytica* lktCA gene cluster cassette comprises polynucleotide segments encoding EF-Tu and DnaK. In some embodiments of the invention, the chimeric *M. bovis* antigen has the amino acid sequence set forth in SEQ ID NO: 19. In some embodiments, the invention relates to a composition comprising a modified *M. haemolytica* lktCA gene cluster cassette as disclosed herein, and encoding at least one an *M. bovis* antigen. In some embodiments of the invention, the composition comprising a modified *M. haemolytica* lktCA gene cluster cassette as disclosed herein, and encoding at least one an *M. bovis* antigen is a polynucleotide, a plasmid, an expression vector, a host cell, a vaccine, or an immunogenic composition. In some embodiments of the invention, the composition comprising a modified *M. haemolytica* lktCA gene cluster cassette as disclosed herein and encoding at least one an *M. bovis* antigen is a replacement plasmid, an attenuated *M. haemolytica* strain A1 bacterium, or an attenuated *M. haemolytica* strain A6 bacterium. In some embodiments, the invention relates to a vaccine or immunogenic composition comprising a modified *M. haemolytica* lktCA gene cluster cassette as disclosed herein, and encoding at least one an *M. bovis* antigen, and optionally an adjuvant.

In an embodiment, the invention relates to a method for provoking an immune response in an animal, the method comprising administering to the animal at least one effective dose of a composition comprising a modified *M. haemolytica* lktCA gene cluster cassette comprising a polynucleotide encoding an additional leukotoxin neutralizing epitope. In an embodiment, the invention relates to a method for provoking an immune response in an animal, the method comprising administering to the animal at least one effective dose of a composition comprising a modified *M. haemolytica* lktCA gene cluster cassette comprising a polynucleotide encoding an additional leukotoxin neutralizing epitope, and further comprising at least one polynucleotide encoding a heterologous antigen. In an embodiment, the invention relates to a method for provoking an immune response in an animal, the method comprising administering to the animal at least one effective dose of a composition comprising a modified *M. haemolytica* lktCA gene cluster cassette comprising a polynucleotide encoding an additional leukotoxin neutralizing epitope, and further comprising at least one polynucleotide encoding a heterologous antigen, where the heterologous antigen is an *M. bovis* antigen. In an embodiment, the invention relates to a method for provoking an immune response in an animal, the method comprising administering to the animal at least one effective dose of a composition comprising an *M. bovis* antigen.

In some embodiments of the invention, the animal in the method for provoking an immune response in an animal is a mammal. In some embodiments of the invention, the mammal in the method for provoking an immune response in an animal is a cow, a bull, a steer, a heifer, a sheep, a goat, a pig, a bison, an elk, a camel, a dog, or a deer. In some embodiments of the invention, the composition to provoke an immune response in an animal is administered orally, nasally, enterally, parenterally, intramuscularly, intravenously, subcutaneously, intradermally, rectally, vaginally, topically, ocularly, pulmonarily, or by contact application.

In an embodiment, the invention relates to a kit comprising a modified *M. haemolytica* lktCA gene cluster cassette comprising a polynucleotide encoding an additional leukotoxin neutralizing epitope. In an embodiment, the invention relates to a kit comprising a modified *M. haemolytica* lktCA gene cluster cassette comprising a polynucleotide encoding an additional leukotoxin neutralizing epitope, and further comprising a polynucleotide encoding a heterologous antigen. In an embodiment, the invention relates to a kit comprising a modified *M. haemolytica* lktCA gene cluster cassette comprising a polynucleotide encoding an additional leukotoxin neutralizing epitope, and further comprising a polynucleotide encoding at least one *M. bovis* antigen. In an embodiment, the invention relates to a kit comprising an *M. bovis* antigen.

BRIEF DESCRIPTION OF THE DRAWINGS

FIG. 9 depicts a graph of the IgA *Mannheimia* titers in tear secretions of calves challenged with *Mannheimia*. Y axis presents the IgG titers; X axis presents the days after treatment. Solid line, averages of Group 1 calves (G1-av; unvaccinated calves); dotted line, averages of Group 2 calves (G2-av; calves vaccinated with ΔlktCAV4); dashed line, averages of Group 3 calves (G3-av; calves vaccinated with ΔlktCAV4Mbovis).

BRIEF DESCRIPTION OF THE SEQUENCE LISTING

Figure 1:
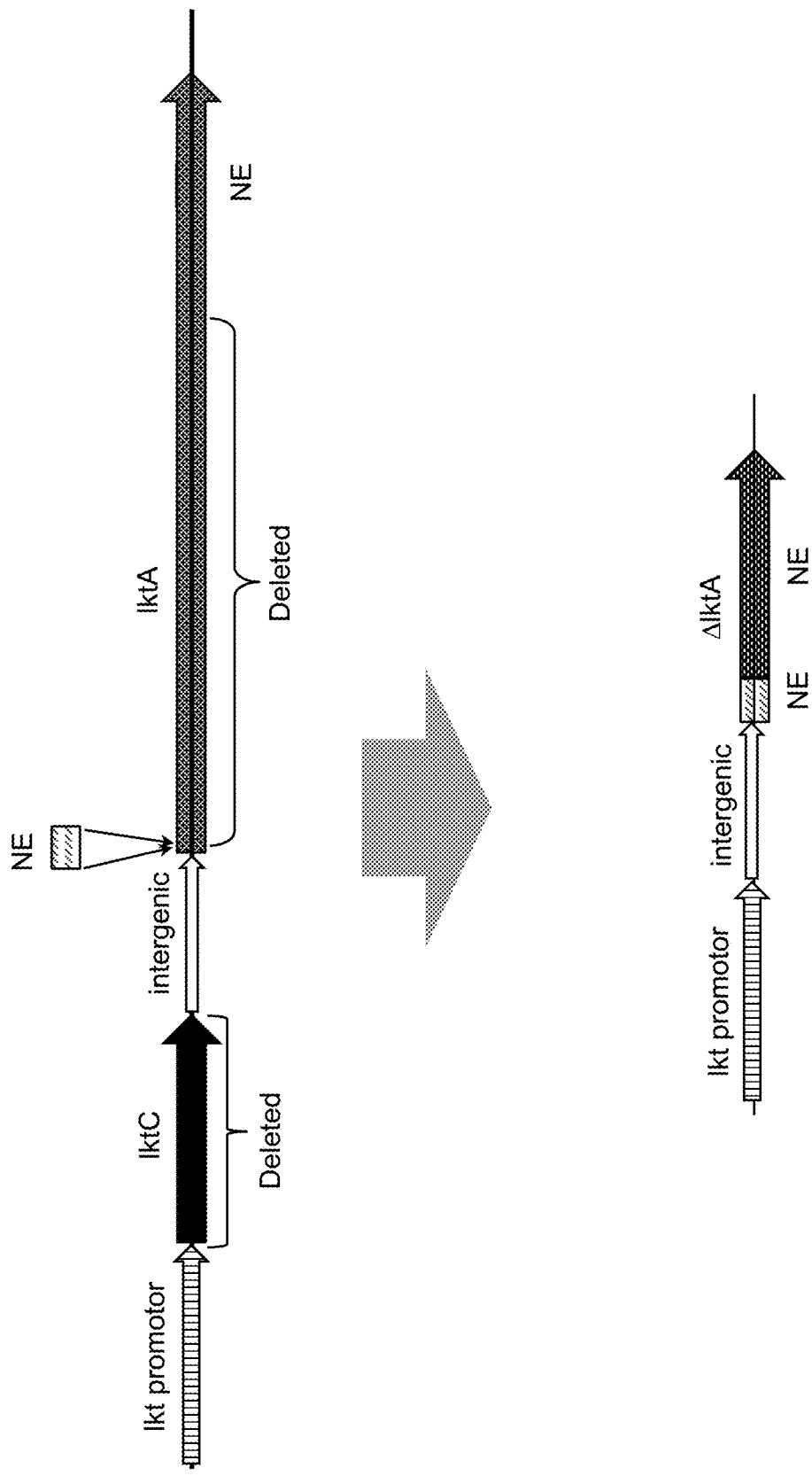
FIG. 1 depicts a schematic of the generation of *M. haemolytica* ΔlktCAV4 cassette. The leukotoxin lktCA gene cluster and the polynucleotide encoding the leukotoxin neutralizing epitope added after the lktA start site are depicted on the upper portion of the figure. Portions of the lktCA gene cluster to be deleted to generate the ΔlktCAV4 cassette are shown bracketed. The *M. haemolytica* ΔlktCAV4 cassette is depicted on the lower portion of the figure. The leukotoxin promotor is shown by a light gray arrow; the leukotoxin C gene is shown by a black arrow; the lktC-lktA intergenic region (leukotoxin A ribosome binding site and start codon) is shown by a white arrow; the leukotoxin A gene is shown by a dotted arrow with the polynucleotide encoding the leukotoxin neutralizing epitope (NE) shown by alternating dashes; and the polynucleotide encoding the added NE is shown by stripes of back dashes.

The nucleotide and amino acid sequences disclosed in the specification are listed in Table 1, below.

| Identifier | Type | Description |
|---|---|---|
| SEQ ID NO: 1 | nucleotide | *M. haemolytica* lktCA gene cluster |
| SEQ ID NO: 2 | nucleotide | ΔlktCAV4 down replacement arm |
| SEQ ID NO: 3 | nucleotide | Down arm forward primer TM56 |
| SEQ ID NO: 4 | nucleotide | Down arm reverse primer TM57 |
| SEQ ID NO: 5 | nucleotide | ΔlktCAV4 up replacement arm |
| SEQ ID NO: 6 | nucleotide | native leukotoxin promotor |
| SEQ ID NO: 7 | nucleotide | lktC-lktA intergenic region |
| SEQ ID NO: 8 | nucleotide | Codon-optimized sequence encoding SEQ ID NO: 9 |
| SEQ ID NO: 9 | amino acid | Added leukotoxin neutralizing epitope |
| SEQ ID NO: 10 | nucleotide | leukotoxin A nucleotides 2192 to 3022 |
| SEQ ID NO: 11 | amino acid | translation of SEQ ID NO: 10 |
| SEQ ID NO: 12 | nucleotide | ΔlktCAV4 cassette |
| SEQ ID NO: 13 | amino acid | ΔlktCAV4 cassette (translation of SEQ ID NO: 12) |
| SEQ ID NO: 14 | nucleotide | Codon-optimized sequence encoding *M. bovis* EF-Tu |
| SEQ ID NO: 15 | amino acid | *M. bovis* EF-Tu (translation of SEQ ID NO: 14) |
| SEQ ID NO: 16 | nucleotide | Codon-optimized sequence encoding *M. bovis* DnaK |
| SEQ ID NO: 17 | amino acid | *M. bovis* DnaK (translation of SEQ ID NO: 16) |
| SEQ ID NO: 18 | nucleotide | Codon-optimized sequence encoding SEQ ID NO: 19 |
| SEQ ID NO: 19 | amino acid | *M. bovis* EF-Tu/DnaK chimera (translation of SEQ ID NO: 18) |
| SEQ ID NO: 20 | nucleotide | ΔlktCAV4Mbovis cassette |
| SEQ ID NO: 21 | amino acid | ΔlktCAV4Mbovis cassette |
| SEQ ID NO: 22 | nucleotide | Primer ΔlktCAV4diagF |
| SEQ ID NO: 23 | nucleotide | Primer ΔlktCAV4diagR |
| SEQ ID NO: 24 | nucleotide | Primer MbovispolyF |
| SEQ ID NO: 25 | nucleotide | Primer MbovispolyR |
| SEQ ID NO: 26 | nucleotide | Primer MhSt1F |
| SEQ ID NO: 27 | nucleotide | Primer MhSt1R |
| SEQ ID NO: 28 | nucleotide | Primer MhSt6F |
| SEQ ID NO: 29 | nucleotide | Primer MhSt6R |

DETAILED DESCRIPTION

The inventors have created a modified *M. haemolytica* lktCA gene cluster cassette comprising a polynucleotide encoding an added leukotoxin neutralizing epitope that may be used as a vector, or as a vaccine. This modified *M. haemolytica* lktCA gene cluster cassette was effective in protecting calves against virulent *M. haemolytica* challenge. The inventors have assembled a chimeric *M. bovis* antigen effective in protecting calves against virulent *M. bovis*. The inventors have inserted a polynucleotide encoding the chimeric *M. bovis* antigen into the modified *M. haemolytica* lktCA gene cluster cassette. This modified *M. haemolytica* lktCA gene cluster cassette expressing the chimeric *M. bovis* antigen was effective in protecting calves against virulent *M. bovis* challenge.

*M. haemolytica* is a gram-negative bacterium which is part of the normal nasal-pharyngeal flora of cattle, sheep, and goats. Under stress and/or concurrent respiratory infection, *M. haemolytica* can gain access to the lungs and cause fibrinous pneumonia. When compared to the wild-type parent, *M. haemolytica* possessing inactive leukotoxin are attenuated and elicit greatly reduced lung damage following experimental pulmonary challenge. Yet such modified strains retain the capacity to colonize the upper respiratory tract of cattle (Tatum F M et al., 1998, "*Construction of an isogenic leukotoxin deletion modified of Pasteurella haemolytica serotype 1: characterization and virulence,*" Microb. Pathog. 24: 37-46). Moreover, cattle vaccinated mucosally with such defined *M. haemolytica* modified strains expressing and secreting inactive, yet immunogenic, leukotoxin (leuko-toxoid) are capable of generating neutralizing antibodies to leukotoxin that afford them resistant to virulent challenge (Briggs R E et al., 2012, "*Mucosal and parenteral vaccination against pneumonic pasteurellosis in cattle with a modified-live in-frame lktA deletion modified of Mannheimia haemolytica,*" Microb. Pathog. 52: 302-309).

The leukotoxin (lkt) operon of *M. haemolytica* codes for four proteins: an internal acyltransferase encoded by lktC; the structural toxin encoded by lktA; an inner membrane protein encoded by lktB; and a membrane fusion protein encoded by lktD. The genes for these four proteins are physically adjacent on the chromosome and are transcribed as lktCA or lktCABD messages.

U.S. Pat. No. 6,331,303, issued Dec. 18, 2001, discloses *P. haemolytica* bacterium which expresses no biologically active leukotoxin, expresses a leukotoxin molecule lacking amino acids 34 to 378, and contains no foreign DNA. In 1999, *P. haemolytica* was renamed as *Mannheimia haemolytica*.

US Patent Publication No. 2014/0170190 discloses a modified *M. haemolytica* strain A1 lktCA gene cluster with a deletion of a polynucleotide fragment consisting of the nucleotides encoding amino acid 4 of leukotoxin C to amino acid 707 of leukotoxin A, and replacement of the native leukotoxin C ribosome binding site (rbs) with an *E. coli* consensus rbs to generate D153ΔlktCA4-707rbs. The mutated lktCA gene cluster was introduced into wild-type *M. haemolytica* strains A1 and A6, resulting in attenuated bacteria. The attenuated *M. haemolytica* A1 and A6 strains were lyophilized, resuspended, and administered intranasally to calves aged 5 to 6 weeks. When administered intranasally, the mixture of attenuated *M. haemolytica* A1 and A6 strains containing D153ΔlktCA4-707rbs afforded protection to *M. haemolytica* challenge. When challenged with *M. haemolytica* A1 strain, nasal administration of *M. haemolytica* A1 and A6 strains containing D153ΔlktCA4-707rbs afforded an average reduction in lung lesion of 62.0% and 76.7% when compared to sham-inoculated cattle. When challenged with *M. haemolytica* A6 strain, nasal administration of *M. haemolytica* A1 and A6 strains containing D153ΔlktCA4-707rbs afforded an average reduction in lung lesion of 85.04% and 14.7% when compared to sham-inoculated cattle. U.S. Pat. No. 9,370,561, issued Jun. 21, 2016 from US Patent Publication No. 2014/0170190, and claims a vaccine comprising live, attenuated *M. haemolytica* A1 and A6 strains containing nucleic acid deletions in their respective leukotoxin A genes, that provide protective immune response against disease caused by *M. haemolytica* strains A1 and A6.

US Patent Application Publication 2019/0381161 discloses an oral vaccine against ruminant respiratory disease, comprising live attenuated *M. haemolytica* bacteria, sucrose, and a Polyvinylpyrrolidone (PVP). The disclosed method allowed reduced dosage of the modified-live vaccine product with retained efficacy when the vaccine was delivered by an oral route via drink.

In an embodiment, in a 5' to 3' orientation, the modified *M. haemolytica* lktCA gene cluster cassette of the invention comprises a leukotoxin promotor, a leukotoxin A ribosome binding site and start codon, a polynucleotide encoding an added leukotoxin neutralizing epitope; and a polynucleotide encoding at least leukotoxin A amino acids 732 to 953. A schematic of the preparation of the modified *M. haemolytica* lktCA gene cluster cassette of the invention is depicted on FIG. 1. The modified *M. haemolytica* lktCA gene cluster cassette of the invention lacks the lktC ribosome binding site, all the nucleotides encoding leukotoxin C, and nucleotides encoding leukotoxin A amino acids 2 to at least 710. In some embodiments of the invention, the modified *M. haemolytica* lktCA gene cluster cassette of the invention lacks nucleotides encoding leukotoxin A amino acids 2 to 731.

Use of bacterial vectors as vehicles to deliver recombinant antigens emerged in the late 1990s. Bacteria-based antigen delivery vectors exhibit multiple advantages, such as the possibility to control its intrinsic infectious power, its non-integrative properties, ability to regulate the amount and in vivo localization of the antigen, a potential for multiple vaccine delivery routes, potent stimulation of the innate and adaptive immune systems, and relatively low manufacturing costs. Bacterial vectors most frequently used as vaccine vectors are *Listeria* and *Salmonella*. Other attenuated bacteria used to express heterologous antigens, are *Pseudomonas aeruginosa, Mycobacterium bovis* (*Bacillus* Calmette-Guerin), *Vibrio anguillarum*, and *Vibrio V*. cholera (see review by Ding, C. al., "*Live Bacterial Vaccine Vector and Delivery Strategies of Heterologous Antigen: A Review*," 2018, Immunology Letters 197: 70-77).

The instant disclosure relates to a modified *M. haemolytica* lktCA gene cluster cassette comprising a polynucleotide encoding an added leukotoxin neutralizing epitope. The polynucleotide encoding the added leukotoxin neutralizing epitope may be inserted downstream of the leukotoxin A ribosome binding site and start codon. Prior to the present disclosure, the effect of the insertion of nucleotides encoding an additional leukotoxin neutralizing epitope to the *M. haemolytica* lktCA gene cluster was not known. Prior to the instant application, it was not known if a modified *M. haemolytica* lktCA gene cluster cassette with an polynucleotide encoding an additional leukotoxin neutralizing epitope would be useful for the expression of heterologous antigens, and/or for the preparation of compositions, vaccines, or immunogenic compositions for administration to animals. In the instant disclosure, a gene replacement plasmid comprising the modified *M. haemolytica* lktCA gene cluster cassette was designed which recombined with wild-type *M. haemolytica* A1 and A6 serotypes to generate attenuated *M. haemolytica* strain A1 and strain A6 bacteria. Prior to the instant disclosure, it was not known whether administration of a vaccine comprising a modified *M. haemolytica* lktCA gene cluster cassette comprising a polynucleotide encoding an added neutralizing would elicit an immune response in an animal.

Disclosed herein are modified lktCA gene cluster cassettes derived from D153 ltkCA gene cluster. The wild type lktCA gene cluster has the nucleotide sequence set forth in SEQ ID NO: 1.

The inventors prepared an *M. haemolytica* replacement plasmid comprising the modified *M. haemolytica* lktCA gene cluster cassette. The modified *M. haemolytica* lktCA gene cluster cassette contains an inserted polynucleotide encoding an added leukotoxin neutralizing epitope. The polynucleotide encoding the added leukotoxin neutralizing epitope may be inserted downstream of the lktA ribosome binding site and start codon. The modified *M. haemolytica* lktCA gene cluster cassette contains a deletion of lktC gene nucleotides −12 to 504, and an in-frame deletion of the lktA gene nucleotides 4 to 2191, and an insertion of nucleotides encoding an additional leukotoxin neutralizing epitope downstream of the lktA ribosome binding site and start codon, and upstream of the lktA nucleotide 2192. The inventors utilized the replacement plasmid, designated herein pΔlktCAV4, to modify *M. haemolytica* strains D153 and D174, virulent lung isolates of *M. haemolytica* serotypes 1 and 6 respectively. The resultant *M. haemolytica* modified products retain the native lkt promotor, and the native lktC/lktA intervening region (including the lktA ribosome binding site, rbs). In the instant application modified *M. haemolytica* strains comprising the ΔlktCAV4 cassette are designated as D153ΔlktCAV4 and D174ΔlktCAV4. Prior to the present disclosure, the effect of the deletion of lktC nucleotides −12 to 504, the in-frame deletion of lktA gene nucleotides 4 to 2191, and the addition of a polynucleotide encoding an additional leukotoxin neutralizing epitope in modified *M. haemolytica* strains D153 and D174M was not known. Prior to the instant application, it was not known if a modified lktCA gene cluster cassette comprising a deletion of lktC nucleotides −12 to 504, and replacement of the lktA nucleotides 4 to 2191 for a polynucleotide encoding an additional leukotoxin neutralizing epitope would generate a cassette useful for the expression of heterologous antigens and/or the preparation of vaccines or immunogenic compositions for administration to animals. Prior to the instant disclosure, it was not known whether administration of a vaccine comprising attenuated *M. haemolytica* bacteria comprising D153ΔlktCAV4 and/or D174ΔlktCAV4 would elicit an immune response in mammals.

The engineered insertions and deletions into the lktCA gene cluster cassette result in novel polynucleotides which are useful for the expression of heterologous antigens. The heterologous antigen may be added directly to the ΔlktCAV4 cassette, to a plasmid containing the ΔlktCAV4 cassette, or to a bacteria comprising the ΔlktCAV4 cassette. For example, polynucleotides encoding heterologous antigens may be expressed in a ΔlktCAV4 cassette, a plasmid containing such cassette, or *M. haemolytica* containing such cassette (such as D153ΔlktCAV4 and D174ΔlktCAV4). In an embodiment, the invention is directed to at least one modified *M. haemolytica* lktCA gene cluster cassette comprising a polynucleotide encoding an additional leukotoxin neutralizing epitope and encoding a heterologous antigen. In some embodiments of the invention, the modified *M. haemolytica* lktCA gene cluster cassette comprises the native leukotoxin promotor, the native lktC-lktA intergenic region, added nucleotides encoding an additional leukotoxin neutralizing epitope, and native nucleotides encoding lktA amino acids 732 to 953 (set forth in SEQ ID NO: 11). In some embodiments of the invention, the modified *M. haemolytica* lktCA gene cluster cassette comprises lktA nucleotides 2192 to 3022 of SEQ ID NO: 1 (ΔlktCAV4 cassette).

In an embodiment, the invention relates to a modified *M. haemolytica* lktCA gene cluster cassette comprising a leukotoxin promotor, a leukotoxin A ribosome binding site and start codon, a polynucleotide encoding an added leukotoxin neutralizing epitope, and a polynucleotide encoding leukotoxin A amino acids 732 to 953. In some embodiments of the invention, the leukotoxin promotor, the lktA ribosome binding site and start codon, the polynucleotide encoding an added leukotoxin neutralizing epitope, and the polynucleotide encoding at least leukotoxin A amino acids 732 to 953 are from *M. haemolytica* strain A1 or *M. haemolytica* strain A6. In some embodiments of the invention, the modified *M. haemolytica* lktCA gene cluster cassette comprises a leukotoxin promotor polynucleotide fragment with the nucleotide sequence set forth in SEQ ID NO: 6; an lktA ribosome binding site and start codon with the nucleotide sequence set forth in SEQ ID NO: 7; an added leukotoxin neutralizing epitope with the amino acid sequence QLVITNSKKEKV-TIQNWFREADFAKEVPNYKATKDEKIEEIIGQNGER-ITS KQVDDLIAKGNGKITQDELSKVVDNYEGS, set forth in SEQ ID NO: 9. In some embodiments of the invention, leukotoxin A amino acids 732 to 953 have the amino acid sequence set forth in SEQ ID NO: 11. In some embodiments of the invention, the polynucleotide fragment encoding the added leukotoxin neutralizing epitope has the nucleotide sequence set forth in SEQ ID NO: 8. In some embodiments of the invention, the modified *M. haemolytica* lktCA gene cluster cassette encodes an amino acid sequence set forth in SEQ ID NO: 13.

In an embodiment, the invention relates to a composition comprising a modified *M. haemolytica* lktCA gene cluster cassette comprising a polynucleotide encoding an added leukotoxin neutralizing epitope. In some embodiments of the invention, the composition is a polynucleotide, a plasmid, an expression vector, a host cell, a vaccine, or an immunogenic composition. In some embodiments of the invention, the composition comprising a modified *M. haemolytica* lktCA gene cluster cassette comprising a polynucleotide encoding an added leukotoxin neutralizing epitope is a replacement plasmid, an attenuated *M. haemolytica* strain A1 bacteria, or an attenuated *M. haemolytica* strain A6 bacteria. In some embodiments of the invention, the composition comprising a modified *M. haemolytica* lktCA gene cluster cassette comprising a polynucleotide encoding an added leukotoxin neutralizing epitope is a vaccine or immunogenic composition, and optionally an adjuvant. In some embodiments, the invention relates to at least one plasmid comprising the ΔlktCAV4 cassette. In some embodiments of the invention, the at least one plasmid is a replacement plasmid. In some embodiments, the invention relates to at least one bacteria comprising the ΔlktCAV4 cassette.

Deletion of lktC gene nucleotides −12 to 504 deletes the lktC ribosome binding site and the entire lktC coding region. Deletion of lktA gene nucleotides 4 through 2191 retains the lktC-lktA intergenic region including the lktA ribosome binding site and start codon, as well as lktA gene nucleotides 2192 to 2862, which include the polynucleotides encoding the leukotoxin glycine rich region and the leukotoxin neutralizing epitope. In some embodiments of the invention the modified lktCA gene cluster cassette contains added nucleotides corresponding to restriction endonuclease recognition sites. In some embodiments of the invention, the modified *M. haemolytica* lktCA gene cluster cassette of the invention contains added nucleotides corresponding to at least one EcoRI restriction endonuclease recognition site (nucleotides 1 to 6 of SEQ ID NO: 5). In some embodiments of the invention, the modified *M. haemolytica* lktCA gene cluster cassette contains nucleotides corresponding to at least one MfeI restriction endonuclease recognition site (nucleotides 1 to 6 of SEQ ID NO: 18). In some embodiments of the invention, the modified *M. haemolytica* lktCA gene cluster cassette contains nucleotides corresponding to at least one BamHI restriction endonuclease recognition site (nucleotides 234 to 240 of SEQ ID NO: 8). At least one EcoRI, BamHI, or MfeI restriction endonuclease recognition site may be used to facilitate preparation of the modified *M. haemolytica* lktCA gene cluster cassette, its insertion into plasmids or vectors, or insertion of polynucleotides encoding heterologous antigens into the modified *M. haemolytica* lktCA gene cluster cassette.

In some embodiments of the invention, the lkt promotor in the modified *M. haemolytica* lktCA gene cluster cassette has the nucleotide sequence set forth in SEQ ID NO: 6. In some embodiments of the invention, the leukotoxin neutralizing epitope encoded by the added polynucleotide inserted downstream of the lktC-lktA intergenic region in the modified *M. haemolytica* lktCA gene cluster cassette has the amino acid sequence set forth in SEQ ID NO: 9. In some embodiments of the invention, the codon-optimized nucleotide sequence encoding the added leukotoxin neutralizing epitope in the modified *M. haemolytica* lktCA gene cluster cassette is set forth in SEQ ID NO: 8. In some embodiments of the invention, the lktC-lktA intergenic region in the modified *M. haemolytica* lktCA gene cluster cassette has the nucleotide sequence set forth in SEQ ID NO: 7. In some embodiments of the invention, the LktA amino acids 732 to 953 in the modified *M. haemolytica* lktCA gene cluster cassette have the amino acid sequence set forth in SEQ ID NO: 11. In some embodiments of the invention, the LktA amino acids 732 to 953 in the modified *M. haemolytica* lktCA gene cluster cassette are encoded by the nucleotide sequence set forth in SEQ ID NO: 10. In some embodiments of the invention, the modified *M. haemolytica* lktCA gene cluster cassette ΔlktCAV4 encodes a polypeptide with the amino acid sequence set forth in SEQ ID NO: 13. In some embodiments of the invention, the modified *M. haemolytica* lktCA gene cluster cassette comprises the nucleotide sequence set forth in SEQ ID NO: 12.

In an embodiment, the invention relates to a modified *M. haemolytica* lktCA gene cluster cassette comprising a polynucleotide encoding an additional leukotoxin neutralizing epitope, further comprising a polynucleotide encoding at least one heterologous antigen. In some embodiments of the invention, the polynucleotide encoding the at least one heterologous antigen is inserted upstream of the polynucleotide encoding the added leukotoxin neutralizing epitope. In some embodiments of the invention, the polynucleotide encoding the at least one heterologous antigen inserted in the modified *M. haemolytica* lktCA gene cluster cassette may be from *Achromobacter anitratum; Actinobacillus lignieresi; Actinomyces bovis; Alcaligenes faecalis; Bacillus anthracis; Brucella abortus; Clostridium chauvoei; Clostridium hemolyticum; Clostridium novyi; Clostridium perfringens; Clostridium perfringens* Type C*; Clostridium septicum; Corynebacterium pyogenes; Corynebacterium renale; Diplococcus pneumoniae; Enterobacter aerogenes; Erysipelothrix insidiosa; Escherichia coli; Hemophilus bovis; Klebsiella pneumoniae; Leptospira canicola; Leptospira hyos; Leptospira icterohaemorrhagica; Leptospira Pomona; Leptospira sejroc phosa; Listeria monocytogenes;*

*Moraxella bovis; Mycobacterium tuberculosis; Mycoplasma bovis; Mycoplasma mycoides; Nocardia asteroids; Pasteurella haemolytica; Pasteurella multocida; Proteus mirabilis; Pseudomonas aeruginosa; Salmonella anatum; Salmonella arizona; Salmonella dublin; Salmonella newport; Salmonella typhimurium, Sphaerophorus necrophorus; Staphylococcus aureus; Streptococcus agalactiae; Streptococcus dysgalactiae; Streptococcus pyogenes; Streptococcus uberus; Vibrio fetus*; and *Yersinia pseudotuberculosis*.

*Mycoplasma bovis* (*M. bovis*) is a member of the class Mollicutes, a wall-less group of bacteria that comprise a diverse group of organisms possessing the smallest genomes of self-replicating organisms. *M. bovis* was first recognized in 1961 when the bacterium was isolated from a cow with severe mastitis. *M. bovis* can cause a variety of other disorders including of pneumonia, arthritis, keratoconjunctivitis, mastitis, and otitis media. *M. bovis* is able to colonize and persist on mucosal surfaces, and form biofilms. *M. bovis* adhesin molecules, such as variable surface proteins (VSP), can undergo rapid size change which presents an ever changing target and contributes to immune evasion (Lysnyansky I, et al., "*Phenotypic Switching of Variable Surface Lipoproteins in Mycoplasma bovis Involves High-Frequency Chromosomal Rearrangements,*" 1996, J. Bacteriol. 178: 5395 to 5401; Beier T, et al., "*Intraspecies Polymorphism of vsp Genes and Expression Profiles of Variable Surface Protein Antigens (Vsps) in Field Isolates of Mycoplasma bovis,*" 1998 Vet. Microbiol. 63:189 to 203). Both, in vitro and in vivo, evidence suggests *M. bovis* can survive intracellularly and cause apoptosis. The economic cost attributed to *M. bovis* in the United States alone is estimated at one billion U.S. dollars annually.

The role of *M. bovis* in the multi-factorial bovine respiratory disease (BRD) is complex. In naturally-infected cattle, *M. bovis* is often detected in association with other microorganisms leading to the hypothesis that synergism of pathogens contributes to the severe lung lesions observed in cattle afflicted with pneumonia (Maunsell F. P., et al., 2011, "*Mycoplasma bovis Infections in Cattle,*" J. Vet. Intern. Med. 25(4): 722-783; Caswell J. L. and Archambult M., 2008, "*Mycoplasma bovis pneumonia in cattle,*" Anim. Health Res. Rev. 8(2): 161-186; and Nicholas R. A. J. and Ayling R. D., 2003, "*Mycoplasma bovis: disease, diagnosis, and control,*" Res. Vet. Sci. 74: 105-112). The most common identified microorganisms co-isolated with *M. bovis* are *Pasteurella multocida, Mannheimia haemolytica, Histophilus somni*, bovine respiratory syncytial virus (BRSV), bovine herpes virus 1 (BHV-1), bovine viral diarrhea virus (BVDV), and parainfluenza virus type 3. A recent study investigating a large number of mortalities in North America bovine feedlots showed *Mannheimia haemolytica* to be most frequently isolated (91%), followed by *Mycoplasma bovis* (63%), *Histophilus somnus* (57%), and *Pasteurella multocida* (13%) (Klima C. L., et al., "*Pathogens of Bovine Respiratory Disease in North American Feedlots Conferring Multidrug Resistance Via Integrative Conjugative Elements,*" 2014, J. Clin. Microbiol. 52: 438-448).

Improved vaccines against *M. bovis* which are safe and effective against all of its disease manifestations are urgently needed. Research on the development of protective vaccines against *M. bovis* has been active for many years. Although there has been some bacterin-based vaccines, the wide antigenic variation shown by *M. bovis* suggests that such a vaccine produced from a single isolate may not confer broad protection against this phenotypically adaptive bacterium. Because of *M. bovis*' extreme variability, selecting conserved *M. bovis* proteins as the underpinning for a *M. bovis* vaccine is an alternative approach towards creating a widely effective vaccine.

Heat shock proteins are a family of proteins that are produced by cells in response to exposure to stressful conditions. They were first described in relation to heat shock, but are now known to also be expressed during other stresses including exposure to cold, UV light, and during wound healing or tissue remodeling. Mycobacterial heat shock proteins serve as molecular chaperones for other proteins during stress conditions and help to recycle damaged proteins. Heat shock proteins DnaK and GroEL are molecular chaperones that assist in correct folding and assembly of proteins. DnaK and GroEL are conserved in both prokaryotes and eukaryotes. Polynucleotides encoding DnaK have been used with mixed results to protect mice against *Chlamydophila abortus* infection (Héchard C. et al., "Protection evaluation against *Chlamydophila abortus* challenge by DNA vaccination with a dnaK-encoding plasmid in pregnant and non-pregnant mice," 2002, Vet. Res. 33(3): 313-326; Héchard C. et al., "*Proteic boost enhances humoral response induced by DNA vaccination with the dnaK gene of Chlamydophila abortus but fails to protect pregnant mice against a virulence challenge,*" Vet. Res. 34(1): 119-125). A subunit vaccine comprising *Francisella tularensis* (FT) DnaK and surface lipoprotein Tul4 protected mice against lethal respiratory infection with FT (Ashtekar A. R. et al., "*A Mucosal Subunit Vaccine Protects against Lethal Respiratory Infection with Francisella tularensis LVS,*" 2012, PLoS ONE 7(11): e50460). A mutated human papillomavirus (HPV) E6 fused to polynucleotides encoding HSP70 was used as a DNA vaccine in a Phase I clinical trial, and found to generate HPV-specific T-cell responses in patients (Trimble C. et al., "A Phase I Trial of a Human Papillomavirus DNA Vaccine for HPV16+ Cervical Intraepithelial Neoplasia 2/3," 2009, Clin. Cancer Res. 15(1):), and mycobacterial HSP70 has been shown to induce protective immunity by DNA vaccination in mice (Sachdeva R., et al., "*Immunogenicity and Efficacy of Single Antigen Gp63, Polytope and PolytopeHSP70 DNA Vaccines against Visceral Leishmaniasis in Experimental Mouse Model,*" 2009, PLoS ONE e7880).

The elongation factor thermo unstable protein (EF-Tu) is a prokaryotic elongation factor responsible for catalyzing the binding of an aminoacyl-tRNA (aa-tRNA) to the ribosome. The EF-Tu protein facilitates the selection and binding of an aa-tRNA to the A-site of the ribosome. EF-Tu is one of the most abundant and highly conserved proteins in prokaryotes. EF-Tu has been found on the surface of a wide range of prokaryotes, and in membrane vesicles in several bacteria. In *M. bovis*, EF-Tu stimulates a humoral immune response and interacts with host immune regulators, as well as binding to innate immune effectors (Harvey K. L. et al., 2019, "*The Diverse Functional Roles of Elongation Factor Tu (EF-Tu) in Microbial*" Front. Microbiol. 24 Oct. 2019).

In an embodiment, the invention relates to an *M. bovis* antigen comprising EF-Tu or DnaK. In some embodiments of the invention, the *M. bovis* antigen comprises EF-Tu and DnaK. In some embodiments of the invention, the *M. bovis* antigen comprises a chimera. In some embodiments of the invention, the *M. bovis* antigen comprises an EF-Tu and DnaK chimera. In some embodiments, the invention relates to a composition comprising the *M. bovis* antigen of the invention. In some embodiments of the invention, the composition comprising an *M. bovis* antigen is a polynucleotide, a plasmid, an expression vector, a host cell, a vaccine, or an immunogenic composition. In some embodiments of the invention, the composition comprising the *M. bovis* antigen is a replacement plasmid, an attenuated *M. haemolytica* strain A1 bacterium, or an attenuated *M. haemolytica* strain A6 bacterium. In some embodiments, the invention relates to a vaccine or immunogenic composition comprising the *M. bovis* antigen as disclosed herein, and optionally an adjuvant.

Figure 2:
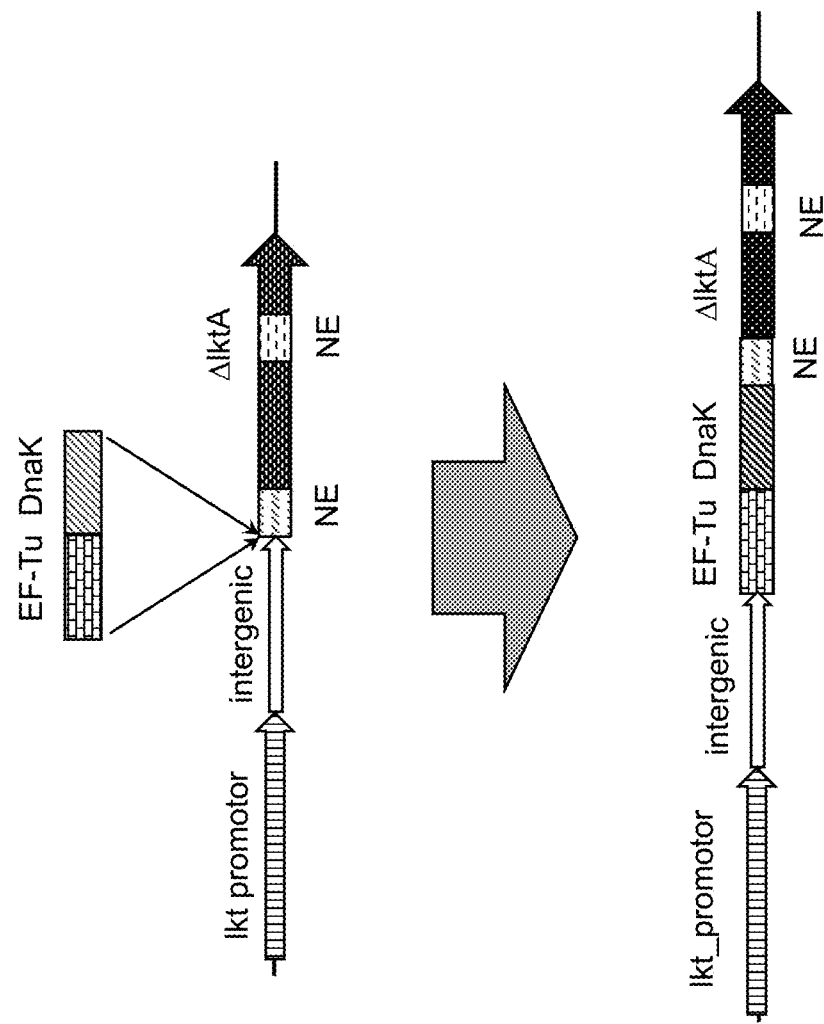
FIG. 2 depicts a schematic of the generation of the *M. haemolytica* ΔlktCAV4Mbovis cassette from the *M. haemolytica* ΔlktCAV4 cassette. The *M. haemolytica* ΔlktCAV4 cassette and the polynucleotide encoding the added *M. bovis* EF-Tu/DnaK chimera are depicted on the upper portion of the figure. The *M. haemolytica* ΔlktCAV4Mbovis cassette is depicted on the lower portion of the figure. The leukotoxin promotor is shown by a light gray arrow; the lktC-lktA intergenic region is shown by a white arrow; the polynucleotide encoding the added NE is shown by stripes of back dashes; the leukotoxin A gene portions present are shown by a dotted arrow; the polynucleotide encoding leukotoxin A NE is shown by alternating dashes; the polynucleotide encoding *M. bovis* EF-Tu is shown by horizontal bricks; and the polynucleotide encoding *M. Bovis* DnaK is shown by diagonal stripes.

Live *M. haemolytica* leuko-toxoid modified strains have been proven safe and effective cattle vaccines when administered mucosally. The co-expression of potentially protective *M. bovis* antigens coupled to leuko-toxoid could serve as platform affording two-way protection against these two important pathogens causing BRD. To realize such a product, a polynucleotide encoding antigenic portions of the conserved *M. bovis* proteins Elongation factor Tu (EF-Tu) and Hsp70 (DnaK) was custom synthesized and inserted in-frame into a temperature-sensitive replacement plasmid containing the ΔlktCAV4 leuko-toxoid sequence ("Construction of In-Frame aroA Deletion Modifieds of *Mannheimia haemolytica*, *Pasteurella multocida*, and *Haemophilus somnus* by Using a New Temperature-Sensitive Plasmid," 2005, Appl. Environ. Microbiol. 71(11): 7196-7202). The resulting chimeric sequence was called ΔlktCAV4Mbovis. FIG. 2 depicts a schematic of the construction of the ΔlktCAV4Mbovis cassette from the ΔlktCAV4 cassette. The same replacement plasmid was used to generate chromosomal modified strains of *M. haemolytica* serotype 1 and serotype 6 that expressed and secreted *M. bovis* EF-Tu-Hsp70 antigenic peptides coupled to leuko-toxoid.

Vaccine strains comprising the ΔlktCAV4Mbovis cassette were produced for *M. haemolytica* serotypes A1 and A6 because cattle develop resistance to further mucosal colonization, in serotype-specific manner (Frank G. H., 1985, "Serotype-specific resistance to nasal colonization by *Pasteurella haemolytica* in cattle," Am. J. Vet. Res. 46(11): 2245-2248). Thus, to increase the probability that colonization would occur, *M. haemolytica* serotypes 1 and 6 comprising the ΔlktCAV4Mbovis cassette were administered as vaccine in this study. The modified *M. haemolytica* comprising the ΔlktCAV4Mbovis cassette can colonize the nasal-pharyngeal mucosa of cattle upon either nasal or oral delivery. When established in the upper respiratory tract these modified *M. haemolytica* will secrete recombinant immunogenic fusion peptide consisting of leuko-toxoid and *M. bovis* EF-Tu-Hsp70 antigens directly onto the mucosal surface of the host to stimulate targeted immune responses at the site where both *M. bovis* and *M. haemolytica* initiate colonization. The two *M. haemolytica* vaccine strains described here significantly decreased middle ear infection (P<0.05) and greatly reduced the *M. bovis* lung burden of (P<3.4E-07) after experimental challenge.

Figure 3:
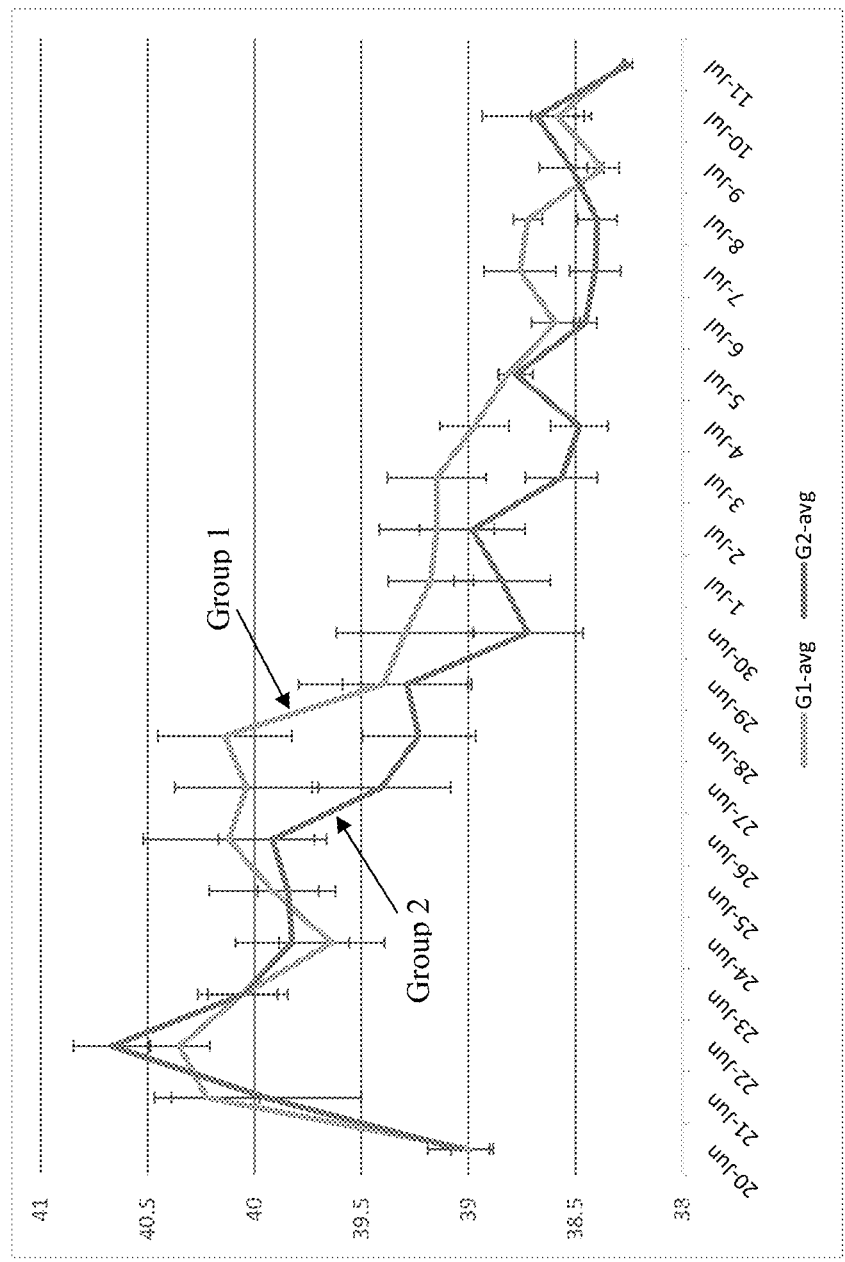
FIG. 3 depicts a graph of the mean rectal temperature of calves challenged with BHV-1, and four days later challenged with *M. bovis*. Group 1, calves were vaccinated with *M. haemolytica* ΔlktCAV4 vaccine product; Group 2, calves vaccinated with ΔlktCAV4Mbovis vaccine product. Error bars represent the standard error of the mean (SEM). The Y axis presents the temperature in degrees Celsius; the X axis presents dates of treatment.
Figure 4:
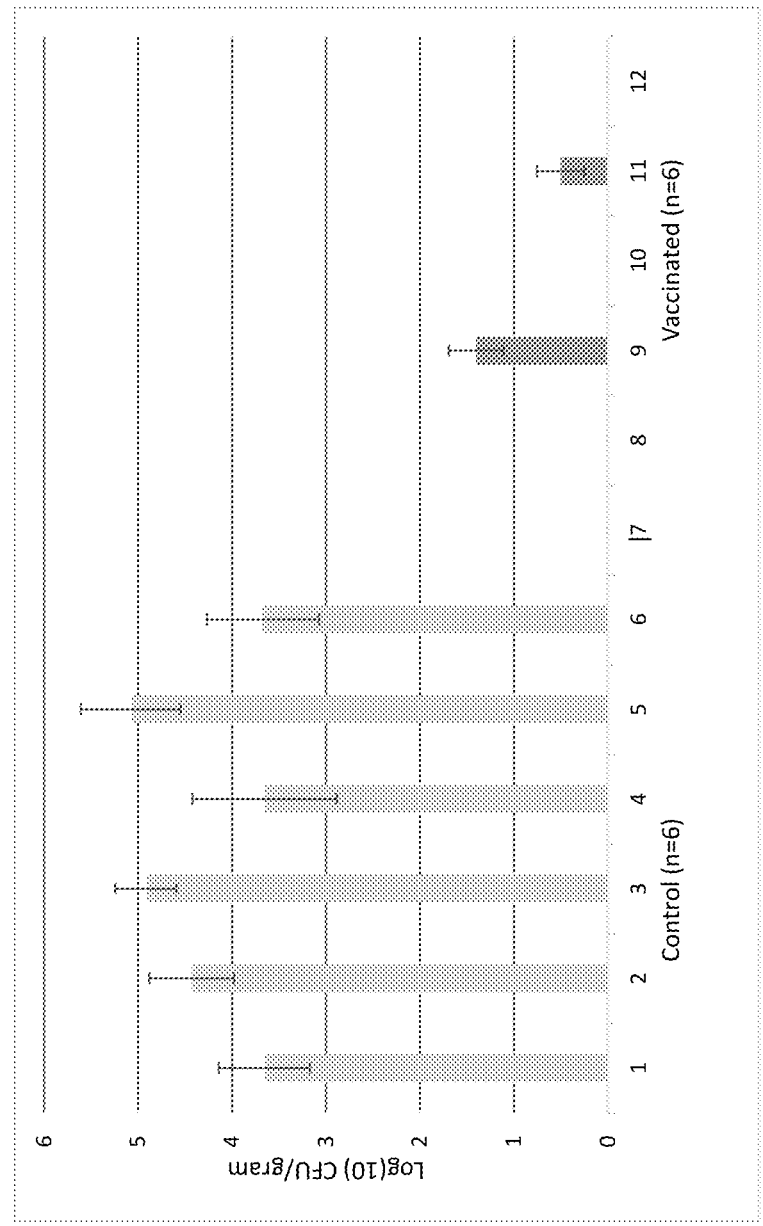
FIG. 4 depicts a graph of the geometric mean quantitative recovery of *M. bovis* from lung specimens. Error bars represent SEM. The Y axis presents the Log(10) cell forming units per gram (Log (10) CFU/gram); the X axis presents the different calves, bars 1 to 6, data from calves vaccinated with *M. haemolytica* ΔlktCAV4; bars 7 to 12, calves vaccinated with ΔlktCAV4Mbovis vaccine product.

In the instant application, a novel delivery system was used where a polynucleotide encoding *M. bovis* antigens was inserted in a modified *M. haemolytica* lktCA gene cluster cassette. A polynucleotide encoding an *M. bovis* chimeric antigen was introduced into the ΔlktCAV4 modified *M. haemolytica* lktCA gene cluster cassette in a replacement plasmid to generate pΔlktCAV4Mbovis replacement plasmid. Attenuated *M. haemolytica* serotype A1 and serotype A6 were obtained following transformation of the wild type *M. haemolytica* serotypes with the pΔlktCAV4Mbovis replacement plasmid. The attenuated bacterial products were named D153ΔlktCAV4Mbovis and D174ΔlktCAV4Mbovis. The attenuated bacterial products were used as vaccine product. A graph of the mean rectal temperature of calves vaccinated with ΔlktCAV4MBovis vaccine product or ΔlktCAV4 vaccine product, challenged with BHV-1, and four days later challenged with *M. bovis* is depicted on FIG. 3. As seen in this graph, the temperatures of the calves in the group vaccinated with ΔlktCAV4 vaccine product (Group 1), and the calves vaccinated with ΔlktCAV4Mbovis vaccine product (Group 2) decreased after a short spike. FIG. 4 shows that *M. bovis* was recovered from the lungs of all the control calves, while only two of the vaccinated calves had low levels of *M. bovis*, and the remaining had no detectable levels of *M. bovis*.

Figure 5:
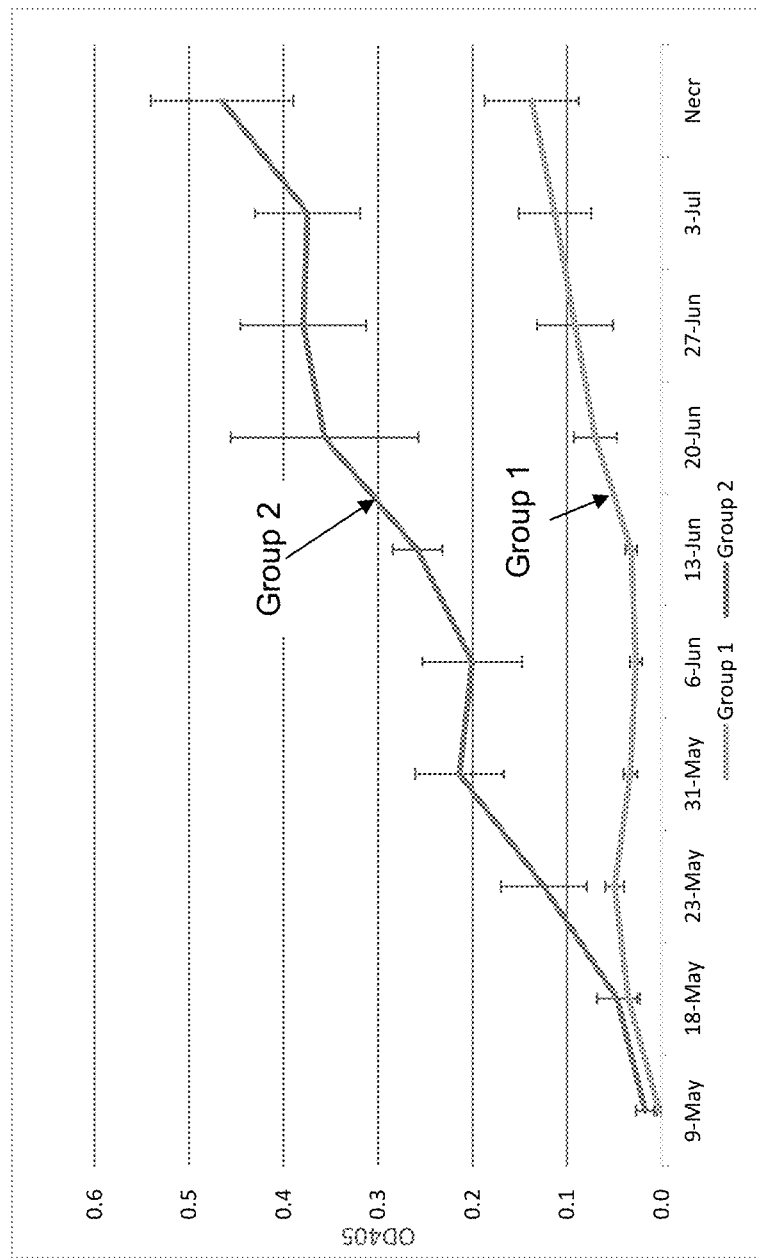
FIG. 5 depicts a graph of the anti-DnaK antibody levels in serum post-vaccination and challenge. Y axis presents the optical density measurements at 405 nm (OD405); X axis presents dates of measurement. Group 1 (ΔlktCAV4 vaccine, no *M. bovis* payload); Group 2 (ΔlktCAV4Mbovis vaccine, with *M. bovis* payload).

As shown in FIG. 5, the DNA K antibody titers of calves vaccinated with ΔlktCAV4 vaccine product and challenged with *M. bovis* were lower than the DNA K antibody titers in calves vaccinated with ΔlktCAV4Mbovis vaccine product and challenged with *M. bovis*. The DNA K antibody titers of these calves trended upwards throughout the trial.

In an embodiment, the invention provides vaccines and immunogenic compositions that, when administered to a subject, elicit an immune response to *M. haemolytica* and/or *M. bovis* in the subject, e.g., a protective immune response. Methods of using the immunogenic compositions/vaccines to prevent or attenuate the spread of *M. haemolytica* and/or *M. bovis* infection in susceptible individuals and/or groups of susceptible individuals are also provided.

Figure 6:
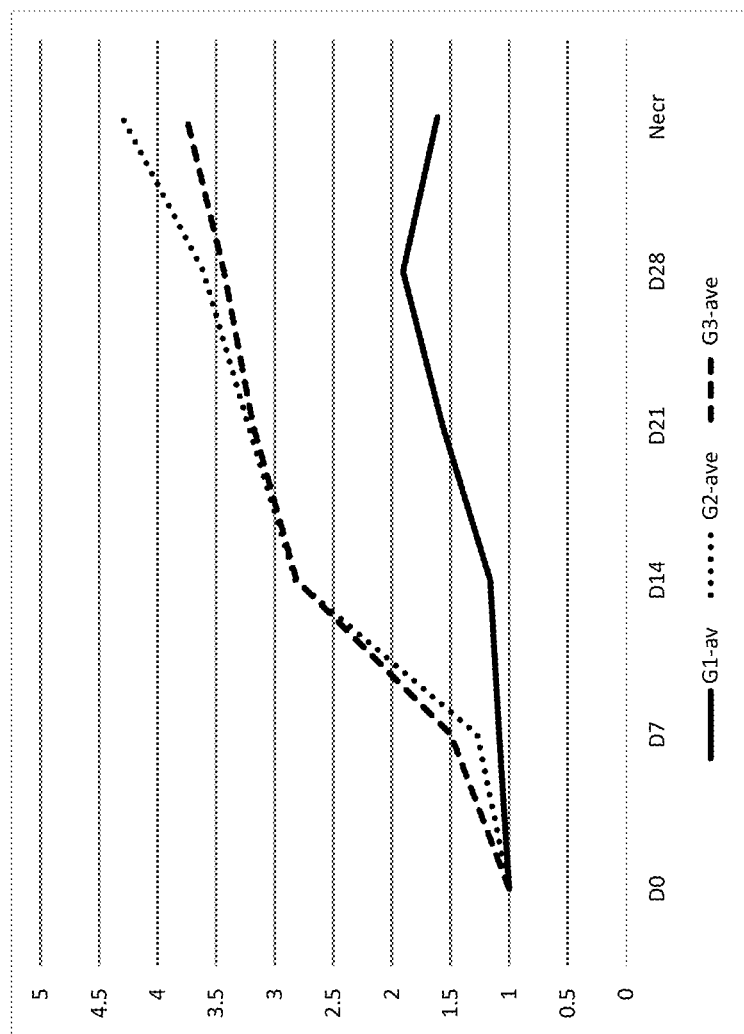
FIG. 6 depicts a graph of the serum IgG1 *Mannheimia* titers in calves challenged with *Mannheimia*. Y axis presents the IgG1 titers; X axis presents the days after treatment. Solid line, averages of Group 1 calves (G1-ave; unvaccinated calves); dotted line, averages of Group 2 calves (G2-ave; calves vaccinated with ΔlktCAV4); dashed line, averages of Group 3 calves (G3-ave; calves vaccinated with ΔlktCAV4Mbovis).
Figure 7:
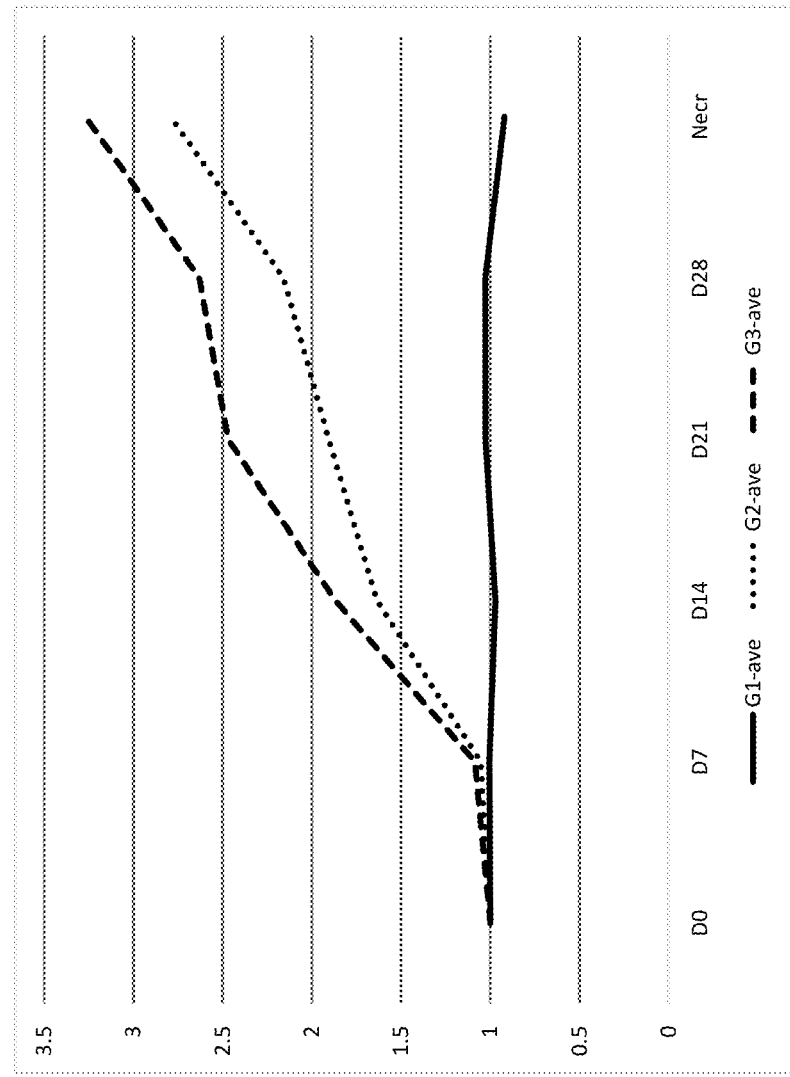
FIG. 7 depicts a graph of the serum IgG2 *Mannheimia* titers in calves challenged with *Mannheimia*. Y axis presents the IgG2 titers; X axis presents the days after treatment. Solid line, averages of Group 1 calves (G1-ave; unvaccinated calves); dotted line, averages of Group 2 calves (G2-ave; calves vaccinated with ΔlktCAV4); dashed line, averages of Group 3 calves (G3-ave; calves vaccinated with ΔlktCAV4Mbovis).
Figure 8:
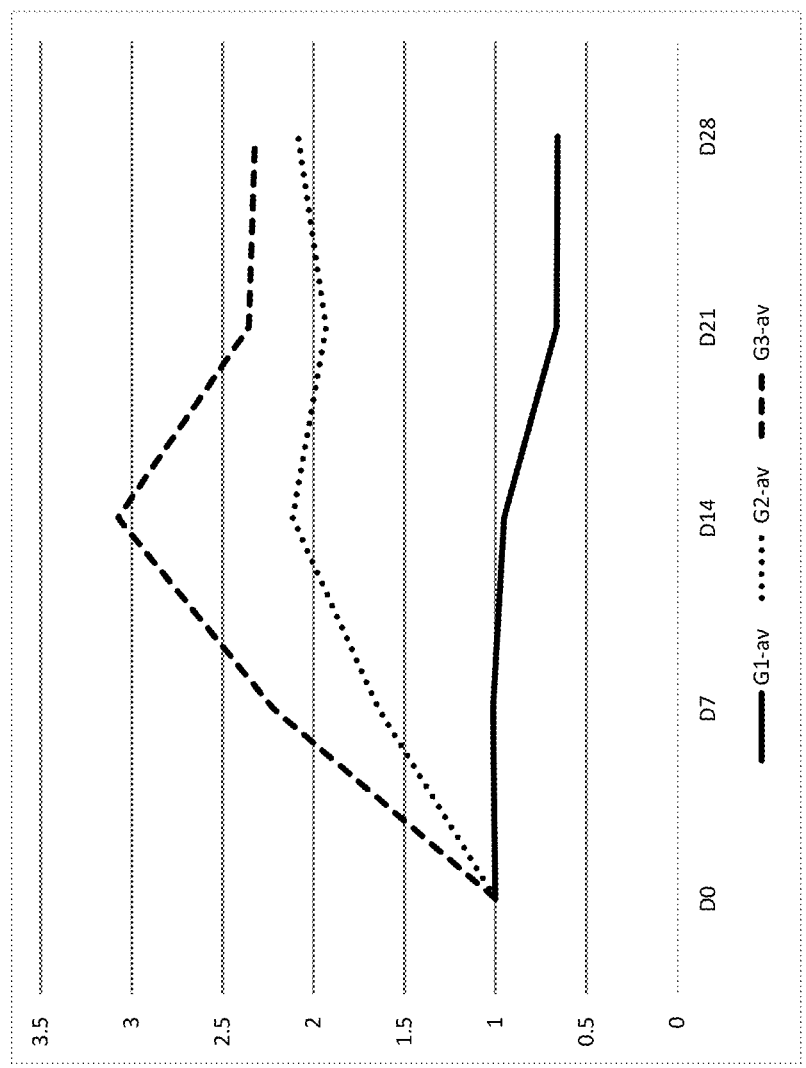
FIG. 8 depicts a graph of the IgG *Mannheimia* titers in tear secretions of calves challenged with *Mannheimia*. Y axis presents the IgG titers; X axis presents the days after treatment. Solid line, averages of Group 1 calves (G1-av; unvaccinated calves); dotted line, averages of Group 2 calves (G2-av; calves vaccinated with ΔlktCAV4); dashed line, averages of Group 3 calves (G3-av; calves vaccinated with ΔlktCAV4Mbovis).

As seen in FIG. 6 and FIG. 7, after *Mannheimia* challenge, the IgG land IgG2 *Mannheimia* titers in serum of calves vaccinated with ΔlktCAV4, or ΔlktCAV4Mbovis increased at a higher rate than in unvaccinated calves. Similarly, as seen in FIG. 8 and FIG. 9, after *Mannheimia* challenge, the levels of *Mannheimia* IgG and IgA titers in tear secretions of calves vaccinated with ΔlktCAV4, or ΔlktCAV4Mbovis increased at a higher rate than in unvaccinated calves. Thus, the ΔlktCAV4, or ΔlktCAV4Mbovis may be used to vaccinate cattle against *M. haemolytica*.

The vaccines or immunogenic compositions provided herein can be in the form of modified *M. haemolytica* lktCA gene cluster cassettes involved in evoking an immune response to *M. haemolytica*, or modified *M. haemolytica* lktCA gene cluster cassettes comprising an *M. bovis* antigen, as plasmids or vectors expressing such cassettes, or bacteria expressing such cassettes. In some embodiments of the invention, the cassettes involved in evoking an immune response to *M. bovis* encode at least a fragment of *M. bovis* EF-Tu. In some embodiments of the invention, the cassettes involved in evoking an immune response to *M. bovis* encode at least a fragment of *M. bovis* DnaK. The immunogenic compositions/vaccines provided herein can be used to immunize or treat any mammal, including, but not limited to, cattle, sheep, goats, pigs, bison, elk, camels, dogs, and deer.

In an embodiment, the invention is directed at a vaccine to control *M. bovis* disease, particularly in bison, beef, and dairy cattle. The vaccine may be used for injectable, intranasal, or oral delivery to the recipient animal, and may be combined with other vaccine components such as *Pasteurella multocida*, *Histophilus somni*, and/or viral components such as Bovine herpes virus 1 (BHV-1), parainfluenza virus type 3 (PI3V), and bovine respiratory syncytial virus (BRSV). Depending upon the selected delivery method, protection against *M. haemolytica* may be an intrinsic property of an *M. bovis* vaccine taught here.

In an embodiment, the invention relates to immunogenic compositions/vaccines that can be used to induce an immune response against *M. bovis*. In an embodiment, the invention relates to methods of administering a vaccine as described herein. The methods involve administering an effective amount of a vaccine sufficient to prevent or lessen the extent of development of symptoms of a *M. bovis* in a subject, when the subject is later exposed to the *M. bovis* bacterium, or contacts an *M. bovis* bacterial infection. In some embodiments of the invention the immunogenic composition used to induce response against *M. bovis* is a chimeric Ef-Tu DnaK antigen.

In an embodiment, the invention relates to a vaccine to control *M. bovis*, where the vaccine consists essentially of a modified *M. haemolytica* lktCA gene cluster cassette encoding *M. haemolytica* leuko-toxoid and an *M. bovis* EF-Tu and DnaK chimera. In some embodiments of the invention, the vaccine to control *M. bovis* comprises a modified *M. haemolytica* lktCA gene cluster cassette of the invention with an inserted recombinant polynucleotide encoding *M. bovis* EF-Tu and DnaK. In some embodiments of the invention, the *M. bovis* EF-Tu and DnaK antigen of the invention has the amino acid sequence set forth in SEQ ID NO: 19. In some embodiments of the invention, the *M. bovis* EF-Tu and DnaK antigen is encoded by a polynucleotide having the nucleotide sequence set forth in SEQ ID NO: 18. In some embodiments of the invention, the vaccine to control *M. bovis* encodes a polypeptide having the amino acid sequence set forth in SEQ ID NO: 21. In some embodiments of the invention, the vaccine to control *M. bovis* comprises bacteria with a modified *M. haemolytica* lktCA gene cluster cassette of the invention, comprising the recombinant polynucleotide of SEQ ID NO: 20.

In an embodiment, the invention provides methods for preparing a vaccine to control *M. bovis*. In some embodiments of the invention, such methods include using a modified *M. haemolytica* lktCA gene cluster cassette comprising a recombinant polynucleotide encoding *M. bovis* EF-Tu and *M. bovis* DnaK. In some embodiments of the invention, such methods include transforming bacteria with a nucleic acid comprising a modified *M. haemolytica* lktCA gene cluster cassette encoding *M. bovis* EF-Tu and *M. bovis* DnaK. Transformation can be achieved by any method known in the art, including, for example, electroporation or chemical transformation. A vaccine can be produced using an isolated nucleic acid to transform a bacterial culture. For example, a transformed bacterial culture can overexpress antigens to produce an immune response. In some embodiments, the vaccine to control *M. bovis* is prepared by inserting a recombinant polynucleotide encoding *M. bovis* EF-Tu and DnaK in a modified *M. haemolytica* lktCA gene cluster cassette of the invention.

In some embodiments, a vaccine provided herein can include a marker of delivery and expression. For example, a polynucleotide encoding *M. bovis* EF-Tu and DnaK may include a nucleic acid that encodes a fluorescent polypeptide (e.g., a green fluorescent protein, GFP). The fluorescent polypeptide will serve as a marker of expression and delivery of the vaccine to an animal. For example, a marker of delivery and expression can be detected e.g. as antibodies to the marker. For example, GFP antibodies may be detected in sera from immunized animals.

It is contemplated that virtually any nucleic acid sequence coding for the amino acid sequence that is or includes *M. bovis* EF-Tu and/or *M. bovis* DnaK may be used as described herein. This includes a nucleic acid sequence encoding the amino acid sequence of the full-length EF-Tu and/or DnaK proteins as well as any sequence of, for example from about 5 to about 50 (or less than 5 or more than 50) amino acids at the beginning (amino terminus) or at the end (carboxy terminus) of the amino acid sequence of the EF-TU/DnaK recombinant polypeptide. The amino acid sequences as described herein may also be shortened on either the amino or carboxy terminus (or both) by one, two, or more amino acids to produce fragments within the context of the invention wherein the fragments produce the same or a similar protective effect. Alternatively, the recombinant EF-Tu/DnaK polypeptide may be a chimera or fusion protein which comprises flanking amino acids sequences which are not adjacent to the native sequence in nature. For example, the adjacent sequences may be corresponding amino acids which are from different but related species; or amino acids which are from different species (e.g. from other bacteria or eukaryotes of interest, e.g. from infectious agents); or from a synthetic sequence, e.g. various tags such as histidine or glutathione S-transferase (GST) tags, linkers, spacers, targeting sequences, etc.).

Any effective route of administration may be utilized to deliver the vaccines of the invention, such as, for example, orally, nasally, enterally, parenterally, intramuscularly or intravenously, subcutaneously, intradermally, rectally, vaginally, topically, ocularly, pulmonarily, or by contact application. From a practical standpoint, oral, (intra)nasal, parenteral (IM, SubQ, and perhaps intradermal) and ocular may be preferred. In some embodiments, vaccine compositions of the invention may be injected (e.g., via intramuscular, intraperitoneal, intradermal and/or subcutaneous routes); or delivered via the mucosa (e.g., to the oral/alimentary, respiratory, and/or genitourinary tracts). Intranasal administration of vaccines may be particularly useful in some contexts, for example for treatment of pneumonia or otitis media (as nasopharyngeal carriage of pneumococci can be more effectively prevented, thus attenuating infection at its earliest stage). In some embodiments of the invention, it may be desirable to administer different doses of a vaccine by different routes. The vaccines provided herein can be administered using any appropriate method. Administration can be, for example, topical (e.g. transdermal, ophthalmic or intranasal); pulmonary (e.g., by inhalation or insufflation or powders or aerosols); oral, or parenteral (e.g. by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, the mode of administration is intraperitoneal. For application in livestock, the preferred mode of administration is oral.

Vaccine compositions are administered in such amounts and for such time as is necessary to achieve a desired result. As used herein, an "immunogenic" amount of the vaccine composition is an amount which is suitable to elicit an immune response. Thus, the amount effective to treat, attenuate, or prevent disease, as used herein, refers to a nontoxic but sufficient amount of the vaccine composition to treat, attenuate, or prevent disease in any subject. For example, the "therapeutically effective amount" can be an amount to treat, attenuate, or prevent infection (e.g., bacterial infection, *M. bovis* infection), etc. The exact amount required to achieve an "immunogenic amount" may vary, depending on the particular component (e.g., polysaccharide, conjugate), and from subject to subject, depending on the species, age, and general condition of the subject, the stage of the disease, the particular pharmaceutical mixture, its mode of administration, and the like.

The amount of *M. bovis* antigen or modified *M. haemolytica* lktCA gene cluster cassette carrying the *M. bovis* antigen in each vaccine dose is selected to allow the vaccine, when administered as described herein, to induce an appropriate immunoprotective response without significant, adverse side effects. An "immuno-protective" or "protective immune" response as used herein is an immune response sufficient to protect an immunized subject from productive infection by a particular pathogen or pathogens to which a vaccine is directed (e.g., *M. bovis* infection). Optimal amounts of components for a particular vaccine can be ascertained by standard studies involving observation of appropriate immune responses in subjects. Following an initial vaccination, subjects can receive one or several booster immunizations adequately spaced in time. Such amounts may vary depending upon which antigen or antigens are expressed by the modified *M. haemolytica* lktCA gene cluster cassette and/or preparations thereof, and may be formulated in a unit dosage form for ease of administration and uniformity of dosage. The expression "unit dosage form," as used herein, refers to a physically discrete unit of vaccine composition appropriate for the patient to be treated. The specific therapeutically effective dose for any particular patient or organism may depend upon a variety of factors including the severity or degree of risk of infection; the activity of the specific vaccine or vaccine composition employed; other characteristics of the specific vaccine or vaccine composition employed; the age, body weight, general health, sex of the subject, the diet of the subject, the pharmacokinetic condition of the subject, the time of administration (e.g., with regard to other activities of the subject such as eating, sleeping, receiving other medicines including other vaccine doses, etc.), the route of administration, the rate of excretion of the specific vaccine or vaccine composition employed; vaccines used in combination or coincidental with the vaccine composition employed; and like factors well known in the veterinary arts.

*M. bovis* vaccines for use in accordance with the present invention may be formulated according to known techniques. An immunogenic amount of a vaccine product can be formulated together with one or more pharmaceutically acceptable carrier materials (organic, inorganic, liquid, or solid). In general, pharmaceutically acceptable carriers include solvents, dispersion media, and the like, which are compatible with pharmaceutical administration. For example, materials that can serve as pharmaceutically acceptable carriers include, but are not limited to sugars such as lactose, glucose, dextrose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; polyols such as glycerol, propylene glycol, and liquid polyethylene glycol; esters such as ethyl oleate and ethyl laurate; agar; buffering agents such as magnesium hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as preservatives, and antioxidants can also be present in the composition, according to the judgment of the formulator (see also Remington's Pharmaceutical Sciences, Fifteenth Edition, E. W. martin (Mack Publishing Co., Easton Pa., 1975).

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Montana, USA), alum, mineral gels such as aluminum hydroxide gel, oil-in-water emulsions, water-in-oil emulsions such as, e.g., Freund's complete and incomplete adjuvants, Block copolymer (CytRx, Atlanta, Georgia, USA), QS-21 (Cambridge Biotech Inc., Cambridge Massachusetts, USA), SAF-M (Chiron, Emeryville California, USA), AMPHIGEN, proprietary oil in water adjuvant (Zoetis, Parsippany, New Jersey, USA), saponin, Quil A (Brenntag Biosector A/S, Ballerup, Denmark), or other saponin fraction, monophosphoryl lipid A, and Avridine lipid-amine adjuvant. Other immunomodulatory agents that can be included in the vaccine of the invention, comprise, e.g., one or more interleukins, interferons, or other known cytokines.

In some embodiments, at least one booster vaccine, is administered after the initial administration of the vaccine of the invention. The booster vaccine may be identical to the vaccine that is initially used to vaccinate the subject. The booster vaccine may be administered as early as four weeks after initial vaccination. In some embodiments, the booster vaccine may be administered at least one year after initial vaccination.

The immunogenic response from the initial or booster vaccine may protect a naive subject from subsequent full-blown *M. bovis* infection when exposed to the bacterium. Alternatively, administration of the initial or booster vaccine is used to provide treatment for an existing *M. bovis* infection. The protective response either wholly or partially prevents or arrests the development of symptoms related to *M. bovis* disease or bacterial infection, in comparison to a non-vaccinated control organism, in which disease progression is not prevented.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

An effective amount of any of the vaccines described herein can be determined by conventional means, starting with a low dose of chimeric EF-Tu/DnaK polypeptide, *M. haemolytica* replacement plasmid comprising such chimera, or *M. haemolytica* bacteria expressing such chimera, and then increasing the dosage while monitoring the effects. An effective amount may be obtained after a single administration of a vaccine or after multiple administrations of a vaccine. Known factors can be taken into consideration when determining an optimal dose per animal. These include the presence of other drugs in the animal, the species, size, age, and general condition of the animal, and the like.

One method of detecting whether an adequate immune response has been achieved is to determine seroconversion and antibody titer in the animal after vaccination. The timing of vaccination and the number of boosters, if any, will preferably be determined by a veterinarian based on analysis of all relevant factors, some of which are described above.

Suitable doses for vaccines according to the practice of the present invention range generally from about $1 \times 10^7$ to about $1.6 \times 10^{10}$ CFU per dose, as may be determined by standard methods. In dairy operations there is an interest in vaccinating cattle as early as 1 day of age. At this very young age, a mucosal delivery route may be preferred. It is also of interest to target the beef segment where 6-8 month old calves are typical recipients of the vaccine.

The effective dose amount of virus, infectious RNA molecule, plasmid, or viral vector, of the present invention can be determined using known techniques, taking into account factors that can be determined by one of ordinary skill in the art such as the weight of the animal to be vaccinated. By way of example, vaccines may be delivered orally, parenterally, intradermally, subcutaneously, intramuscularly, intranasally or intravenously. Oral delivery may encompass, for example, adding the compositions to the feed or drink of the animals.

The present invention further provides methods for preparing a vaccine or immunogenic composition comprising a polynucleotide encoding a chimeric *M. bovis* EF-Tu/DnaK polypeptide, or a chimeric *M. bovis* EF-Tu/DnaK polypeptide, or a ΔlktCAV4Mbovis cassette comprising a polynucleotide encoding a chimeric *M. bovis* EF-Tu/DnaK polypeptide, or a replacement plasmid comprising such a cassette, or bacterial strains comprising such a cassette, or vaccines or immunogenic compositions comprising such a cassette.

The method for preparing such a vaccine may comprise combining an effective amount of a chimeric *M. bovis* EF-Tu/DnaK polypeptide, an *M. haemolytica* replacement plasmid comprising a chimeric *M. bovis* EF-Tu/DnaK insert, or bacterial strains described herein, with a carrier acceptable for pharmaceutical or veterinary use.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention. It will be clear that the invention may be practiced otherwise than as particularly described in the foregoing description and examples. Numerous modifications and variations of the present invention are possible in light of the above teachings and, therefore, are within the scope of the invention.

The invention is directed at a vaccine to control *M. bovis*, particularly in beef, dairy cattle, and bison. The vaccine is intended for injectable, intra-nasal, or oral delivery to the recipient animal and may be combined with other vaccine components such as *Pasteurella multocida*, *Histophilus somni*, and/or viral components such as BHV-1, PI-3V, and BRSV. Depending upon the selected delivery method, protection against *M. haemolytica* may be an intrinsic property of a vaccine comprising the *M. haemolytica* replacement vector taught here.

The vaccine may be delivered as a modified-live vectored product via an attenuated *M. haemolytica* vaccine strain as tested here, or as a killed vaccine strain, or as a subunit vaccine product, or as a DNA vaccine. The *M. haemolytica* replacement vector utilized here consists of a gene-knockout modified which targeted the leukotoxin operon. *M. haemolytica* which does not express an active leukotoxin is dramatically attenuated in lung tissue, but remains capable of colonizing the nasopharynx where it can elicit an immune response. Because leukotoxin itself is an important immunogen, the vaccine strain is designed to express an inactive but immunogenic form of the protein—a genetic toxoid. Within the modified leukotoxin operon was placed an MfeI restriction site specifically for cloning of DNA, allowing heterologous DNA (preferably encoding protective immunogenic epitopes) to be cloned and expressed as a fusion product with the leuko-toxoid. In this case, DNA encoding fragments of *M. bovis* EF-Tu and DnaK (HsP70) were cloned in-frame into the MfeI restriction site.

Nucleotide sequences encoding *M. bovis* EF-Tu and DnaK were codon-optimized. DNA encoding the chimeric protein was synthesized by Blue Heron Biotech (Bothell, Washington, USA). The 5' end was designed with nucleotides corresponding to an MfeI restriction endonuclease recognition site, and the 3' end was designed with nucleotides corresponding to an EcoR1 restriction endonuclease recognition site to allow cloning into a replacement plasmid containing MfeI at the cloning site. After cloning, the resultant plasmid was utilized to generate modified *Mannheimia haemolytica* serotype 1 and serotype 6.

In some embodiments of the invention, a vaccine provided herein can be delivered as a prophylactic vaccine to reduce the risk of developing *M. bovis* disease, should a *Mycoplasma bovis* infection occur. In some instances, a vaccine provided herein can reduce the risk of developing infection by *M. bovis* bacteria. A vaccine provided herein can also be delivered as a prophylactic vaccine to reduce the risk of developing *M. bovis* disease should an *M. bovis* infection occur.

Although mucosal vaccination and leukotoxin deficient *M. haemolytica* are known, inventors are aware of no *M. haemolytica* vectors successfully combining the concepts disclosed herein.

EF-Tu is a prokaryotic elongation factor responsible for catalyzing the binding of an aminoacyl-tRNA to the ribosome. It is a G-protein, and facilitates the selection and binding of an aa-tRNA to the A-site of the ribosome.

All living organisms respond to environmental stresses such as high temperature by synthesizing a set of proteins which have been called heat shock proteins (Hsps). Some of them are highly conserved in the course of evolution, especially the proteins encoded by the groEL(hsp60 or cpn60) and the dnaK(hsp70) genes.

Molecular chaperones are a diverse family of proteins that function to protect proteins in the intracellular milieu from irreversible aggregation during synthesis and in times of cellular stress. The bacterial molecular chaperone DnaK is an enzyme that couples cycles of ATP binding, hydrolysis, and ADP release by an N-terminal ATP-hydrolysing domain to cycles of sequestration and release of unfolded proteins by a C-terminal substrate binding domain. In prokaryotes, the grpE protein is a co-chaperone for DnaK, and acts as a nucleotide exchange factor, stimulating the rate of ADP release 5000-fold.

The majority of *Mannheimia* strains isolated from pulmonary infection in cattle belongs to *M. haemolytica* serotype A1/A6. These strains are sub-dominant to other *M. haemolytica* serotypes in the nasopharynx of healthy cattle, but dominate when the host defenses are at least partly compromised. In the immunocompromised host, they have an increased capacity for proliferation and can achieve relatively high total numbers in the nasopharynx, where they are likely to be transmitted to the nasopharynx of new hosts or to spill over or otherwise enter the lungs. However, pulmonary infection caused by *M. haemolytica* serotype A1 is considered to be non-communicable (i.e. no direct transmission between the lungs) and the continuous circulation of these bacteria in bovine populations seems to depend on their capacity for asymptomatic transmission to the nasopharynx, and not the lungs, of new hosts.

As used herein, "modified *M. haemolytica* lktCA gene cluster vector" and "replacement *M. haemolytica* plasmid" are used interchangeably and refer to a mutated *M. haemolytica* lktCA gene cluster comprising a polynucleotide encoding an added neutralizing epitope inserted downstream of the lktC-lktA intergenic region, and upstream of lktA gene nucleotide 2192. In some embodiments, the modified *M. haemolytica* lktCA gene cluster vector comprises a leukotoxin promotor, an lktC/lktA intergenic region, a polynucleotide encoding an added neutralizing epitope inserted downstream of the lktC-lktA intergenic region, and upstream of lktA gene nucleotide 2192, and lktA nucleotides 2192 to 2862.

In an embodiment, the invention relates to a method for vaccinating an animal. The method comprises administering to an animal an effective amount of a composition comprising a modified *M. haemolytica* lktCA gene cluster cassette comprising a polynucleotide encoding an additional leukotoxin neutralizing epitope. In some embodiments of the invention, the vaccine comprises a cassette of the invention and pharmaceutically acceptable carrier, excipient, or vehicle. In some embodiments of the invention, the animal is an even toed ungulate ruminant. In some embodiments of the invention, the vaccinated animal may be a cattle, a sheep, a goat, a deer, a giraffe, an elk, or a bison.

In an embodiment, the invention relates to a kit for performing methods of eliciting or inducing an immunogenic or protective response against a bacterial antigen. In some embodiments of the invention, the kit comprises a modified *M. haemolytica* lktCA gene cluster vector comprising a polynucleotide encoding an added neutralizing epitope. In some embodiments of the invention the added neutralizing epitope is inserted downstream of the lktC-lktA intergenic region, and upstream of lktA gene nucleotide 2192. In some embodiments of the invention, the kit comprises a polynucleotide encoding a polypeptide with the amino acid sequence set forth in SEQ ID NO: 13. In some embodiments of the invention, the kit comprises a polynucleotide with the nucleotide sequence set forth in SEQ ID NO: 12.

In an embodiment, the invention relates to a kit comprising a modified *M. haemolytica* lktCA gene cluster cassette comprising a polynucleotide encoding an added neutralizing epitope. In some embodiments, the modified *M. haemolytica* lktCA gene cluster cassette comprises a polynucleotide encoding at least one heterologous antigen. In some embodiments of the invention, the kit comprises a modified *M. haemolytica* lktCA gene cluster cassette comprising a polynucleotide encoding an added neutralizing epitope inserted downstream of the lktC-lktA intergenic region, and upstream of lktA gene nucleotide 2192, and comprises a polynucleotide encoding at least one heterologous antigen. In some embodiments of the invention, the kit comprises a modified *M. haemolytica* lktCA gene cluster cassette comprising a polynucleotide encoding an added neutralizing epitope inserted downstream of the lktC-lktA intergenic region, and upstream of lktA gene nucleotide 2192, and a polynucleotide encoding a heterologous antigen. In some embodiments of the invention, the kit comprises a modified *M. haemolytica* lktCA gene cluster cassette comprising a polynucleotide encoding an added neutralizing epitope inserted downstream of the lktC-lktA intergenic region, and upstream of lktA gene nucleotide 2192, and a polynucleotide encoding a heterologous antigen.

In an embodiment, the invention relates to a kit comprising a modified *M. haemolytica* lktCA gene cluster cassette comprising a polynucleotide encoding an added neutralizing epitope and comprises a polynucleotide encoding at least one *M. bovis* antigen. In some embodiments of the invention, the kit comprises a modified *M. haemolytica* lktCA gene cluster cassette comprising a polynucleotide encoding an added neutralizing epitope inserted downstream of the lktC-lktA intergenic region, and upstream of lktA gene nucleotide 2192, and a polynucleotide encoding an *M. bovis* chimeric antigen. In some embodiments of the invention, the kit comprises a modified *M. haemolytica* lktCA gene cluster cassette comprising a polynucleotide encoding an added neutralizing epitope inserted downstream of the lktC-lktA intergenic region, and upstream of lktA gene nucleotide 2192, and a polynucleotide encoding *M. bovis* DnaK and *M. bovis* EF-Tu. In some embodiments of the invention, the kit comprises a polynucleotide encoding the amino acid sequence set forth in SEQ ID NO: 21. In some embodiments of the invention, the kit comprises a polynucleotide with the sequence set forth in SEQ ID NO: 20.

The terms "antigen," "antigenic region," and "immunogen," may be used interchangeably herein. As used herein, an antigen or immunogen, or epitope is generally a portion of a protein (e.g. a peptide or polypeptide). Antigen is a term used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility.

As used herein, an "antigen" or "immunogen" is a substance that induces a specific immune response in a host animal. The antigen may comprise a whole organism either killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

An "immunological response" to a composition or vaccine is the development in the host of a cellular and/or antibody-mediated immune response to a composition or vaccine of interest. Usually, an "immunological response" includes, but is not limited to, one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of cattle, sheep, goats, pigs, bison, elk, camels, dogs, and deer. The term "animal" also includes an individual animal in all stages of development, including newborn, embryonic and fetal stages.

As used herein, the term "about" is defined as plus or minus ten percent of a recited value. For example, about 1.0 g means 0.9 g to 1.1 g.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

Embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby. All publications, patents, and patent applications mentioned in this specification are herein incorporated by reference to the same extent as if each individual publication, patent, or patent application was specifically and individually indicated to be incorporated by reference.

EXAMPLES

Having now generally described this invention, the same will be better understood by reference to certain specific examples, which are included herein only to further illustrate the invention and are not intended to limit the scope of the invention as defined by the claims.

Example 1

Construction Modified *M. Haemolytica* lktCA Gene Cluster Cassette

A modified *M. haemolytica* lktCA gene cluster cassette with an insertion of a polynucleotide encoding an additional *M. haemolytica* leukotoxin neutralizing epitope was prepared.

The polynucleotide cassette was designed to delete parent chromosomal nucleotides from the beginning of the lktC ribosome binding site to the beginning of the lktA ribosome binding site, thereby removing the entire lktC coding region. A second deletion was designed in-frame with the lktA coding region to remove the nucleotides encoding amino acids 2 to 731. A synthetic codon-optimized polynucleotide encoding the leukotoxin neutralizing epitope, flanked upstream by a synthetic MfeI site and downstream by a synthetic BamH1 site, was inserted in-frame with the second deletion, thereby duplicating the neutralizing epitope in the encoded leukotoxoid product. A schematic of the preparation of the modified *M. haemolytica* lktCA gene cluster cassette is depicted on FIG. 1.

The nucleotide sequence of the wild-type *M. haemolytica* D153 lktCA gene cluster is ttctcttttgctaaatagtgttggtaagtagtcccatttgcacaccaat cgttttcaccttagcaaaatctgtatcttttcgcaatgaaggcagca gagcttggaaagtaaggctcgctaaataatacttgtttcttacgtggttc cgtaatacccatacctgaaattgcagcatcaaattgtttttgttttag gctttggattaagctatcaaaaggttggctatggaatgtacaatttgcat tcatctctttacagatagcatttgcaatatccacatcaaaaccgata atttctcccttctcttcggtcatttcaaatggaggatagcttggctccat cacaaatttgatatcttgtgcctgcgcagtaaccacacacccgaata aaagggtcaaaagtgttttttttcataaaaagtccctgtgttttcattata aggattaccactttaacgcagttactttcttaaaaaaagtcttctttca taaagtttgttttatgtcatacaaacacatcaaattgagatgtagtttct caatcctcttgattcctctatctcaaaaaaacaacccaaaagaaaaaa gaaaagtatatgttacattaatattacaatgtaattattttgtttaatt tccctacattttgtataacttaaaacactccttttctcttctgatta tataaaagacaaaaaatacaatttaagctacaaaaaacaacaaaaaaca acaaaaaacacgacaataagatcgagtaatgattatattatgttataat ttttgacctaatttagaataattatcgagtgcaaattATGaatcaatct tattttaacttactaggaaacattacttggctatggatgaactcctccc tccacaaagaatggagctgtgaactactagcacgcaatgtgattcctg caattgaaaatgaacaatatatgctacttatagataacggtattccga tcgcttattgtagttgggcagatttaaaccttgagactgaggtgaaata tattaaggatattaattcgttaacaccagaagaatggcagtctggtg acagacgctggattattgattgggtagcaccattcggacattctcaatt acttttataaaaaatgtgtcagaaatacccctgatatgatcgtcagat ctatacgcttttatccaaagcagaaagaattaggcaaaattgcctactt taaaggaggtaaattagataaaaaaacagcaaaaaaacgttttga tacatatcaagaagagctggcaacagcacttaaaaatgaatttaatttt attaaaaaatagaaggagacatcccttATGggaactagacttac aaccctatcaaatgggctaaaaaacactttaacggcaaccaaaagtggc ttacataaagccggtcaatcattaacccaagccggcagttcttt aaaaactggggcaaaaaaaattatcctctatattccccaaaattaccaa tatgatactgaacaaggtaatggtttacaggatttagtcaaagcg gccgaagagttggggattgaggtacaaagagaagaacgcaataatattg caacagctcaaaccagtttaggcacgattcaaaccgctattg gcttaactgagcgtggcattgtgttatccgctccacaaattgataaatt gctacagaaaactaaagcaggccaagcattaggttctgccgaaa gcattgtacaaaatgcaaataaagccaaaactgtattatctggcattca atctattttaggctcagtattggctggaatggatttagatgaggcct tacagaataacagcaaccaacatgctcttgctaaagctggcttggagct aacaaattcattaattgaaaatattgctaattcagtaaaaacactt gacgaatttggtgagcaaattagtcaatttggttcaaaactacaaaata tcaaaggcttagggactttaggagacaaactcaaaaaatatcggtg gacttgataaagctggccttggtttagatgttatctcagggctattatc gggcgcaacagctgcacttgtacttgcagataaaaatgcttcaaca -continued gctaaaaaagtgggtgcgggttttgaattggcaaaccaagttgttggta atattaccaaagccgtttcttcttacattttagcccaacgtgttgca gcaggtttatcttcaactgggcctgtggctgctttaattgcttctactg tttctcttgcgattagcccattagcatttgccggtattgccgataaatt taatcatgcaaaaagtttagagagttatgccgaacgctttaaaaaatt aggctatgacggagataatttattagcagaatatcagcggggaaca gggactattgatgcatcggttactgcaattaataccgcattggccgcta ttgctggtggtgtgtctgctgctgcagccggctcggttattgcttc accgattgccttattagtatctgggattaccggtgtaatttctacgatt ctgcaatattctaaacaagcaatgtttgagcacgttgcaaataaaattc ataacaaaattgtagaatgggaaaaaaataatcacggtaagaactactt tgaaaatggttacgatgcccgttatcttgcgaatttacaagataat atgaaattcttactgaacttaaacaaagagttacaggcagaacgtgtca tcgctattactcagcagcaatgggataacaacattggtgatttag ctggtattagccgtttaggtgaaaaagtccttagtggtaaagcctatgt ggatgcgtttgaagaaggcaaacacattaaagccgataaattagt acagttggattcggcaaacggtattattgatgtgagtaattcgggtaaa gcgaaaactcagcatatcttattcagaacgccattattgacgccg ggaacagagcatcgtgaacgcgtacaaacaggtaaatatgaatatatta ccaagctcaatattaaccgtgtagatagctggaaaattacagat ggtgcagcaagttctacctttgatttaactaacgttgttcagcgtattg gtattgaattagacaatgctggaaatgtaactaaaaccaaagaaac aaaaattattgccaaacttggtgaaggtgatgacaacgtatttgttggt tctggtacgacggaaattgatggcggtgaaggttacgaccgagtt cactatagccgtggaaactatggtgctttaactattgatgcaaccaaag agaccgagcaaggtagttataccgtaaatcgtttcgtagaaacc ggtaaagcactacacgaagtgacttcaacccataccgcattagtgggca accgtgaagaaaaatagaatatcgtcatagcaataaccagc accatgccggttattacaccaaagataccttgaaagctgttgaagaaat tatcggtacatcacataacgatatctttaaaggtagtaagttcaat gatgcctttaacggtggtgatggtgtcgatactattgacggtaacgacg gcaatgaccgcttatttggtggtaaaggcgatgatattctcgatg gtggaaatggtgatgattttatcgatggcggtaaaggcaacgacctatt acacggtggcaagggcgatgatattttcgttcaccgtaaaggcg atggtaatgatattattaccgattctgacggcaatgataaattatcatt ctctgattcgaacttaaaagatttaacatttgaaaaagttaaacataat cttgtcatcacgaatagcaaaaagagaaagtgaccattcaaaactggt tccgagaggctgattttgctaaagaagtgcctaattataaagca actaaagatgagaaaatcgaagaaatcatcggtcaaaatggcgagcgga tcacctcaaagcaagttgatgatcttatcgcaaaaggtaacg gcaaaattacccaagatgagctatcaaaagttgttgataactatgaatt -continued gctcaaacatagcaaaaatgtgacaaacagcttagataagttaat ctcatctgtaagtgcatttacctcgtctaatgattcgagaaatgtatta gtggctccaacttcaatgttggatcaaagtttatcttctcttcaatttg ctagagcagcttaattttttaatgattggcaactctatattgtttcaca cattatagagttgccgttttatttttataaaaggagacaatatggaagc taaccatcaaaggaatgatcttggtttagttgccctcactatgttggca caataccataatatttcgcttaatccggaa, and is set forth in SEQ ID NO: 1.

A Down-Replacement arm and an Up-Replacement arm were created to introduce the changes in the M. haemolytica lktCA gene cluster. The Down-Replacement arm was generated by amplifying a portion of the M. haemolytica D153 lktCA gene cluster using polymerase chain reaction (PCR). The nucleotide sequence of the Down-arm Forward primer TM56 is AAAGGATCCTTTAACGGTGGTGAT; and is set forth in SEQ ID NO: 3. This Down-arm Forward primer TM56 added nucleotides corresponding to a BamHI restriction endonuclease recognition site at the 5' end of the Down-replacement arm. The nucleotide sequence of the Down-arm Reverse primer TM57 is AAAGAATTCCGGATTAAGCGAAATATTATGGTA TTGT; and is set forth in SEQ ID NO: 4. This Down-arm Reverse primer TM57 added nucleotides corresponding to an EcoRI restriction endonuclease recognition site at the 3' end of the Down-replacement arm. Thus, in a 5' to 3' orientation, the Down-Replacement arm contained nucleotides corresponding to a BamHI restriction endonuclease recognition site, followed by nucleotides 3530 to 4360 of the M. haemolytica D153 lktCA gene cluster of SEQ ID NO: 1, followed by nucleotides corresponding to an EcoRI restriction endonuclease recognition site. The nucleotide sequence of the amplified Down-replacement arm is GGATCCTTTAACG GTGGTGATGGTGTCGATACTAT-TGACGGTAACGACGGCAATGACCGCTTATTTGGTG GTAAAGGCGATGATATTCTCGATGGTGGAAATGGT-GATGATTTTATCGATGGCGGTA AAGGCAACGACCT-ATTACACGGTGGCAAGGGCGATGATATTTTCGTT-CACCGTAAA GGCGATGGTAATGATATTATTACCGAT-TCTGACGGCAATGATAAATTATCATTCTCT GAT-TCGAACTTAAAAGATTTAACATTTGAAAAAGT-TAAACATAATCTTGTCATCACG AATAGCAAAAAGAGAAAGTGACCATT-CAAAACTGGTTCCGAGAGGCTGATTTTGC TAAAGAAGTGCCTAATTATAAAGCAACTAAAGAT-GAGAAAATCGAAGAAATCATCG GTCAAAATGGCGAGCGGATCACCT-CAAAGCAAGTTGATGATCTTATCGCAAAAGGT AACGGCAAAATTACCCAAGATGAGCTAT-CAAAAGTTGTTGATAACTATGAATTGCTC AAACAT-AGCAAAAATGTGACAAACAGCTTAGATAAGT-TAATCTCATCTGTAAGTGC ATTTACCTCGTCTAATGATTCGAGAAATGTATT-AGTGGCTCCAACTTCAATGTTGGAT CAAAGTT-TATCTTCTCTTCAATTTGCTAGAGCAGCTTAATTTT-TAATGATTGGCAACT CTATATTGTTTCACACATTATAGAGTTGCCGTTTTAT-TTTATAAAGGAGACAATATG GAAGCTAACCAT-CAAAGGAATGATCTTGGTTTAGTTGCCCTCAC- TATGTTGGCACAA TACCATAATATTTCGCTTAATCCGGAATTC, and is set forth in SEQ ID NO: 2.

Plasmid PBCSKlktDown was generated by subjecting the amplified Down-replacement arm PCR product to digestion with restriction endonuclease enzymes EcoRI and BamHI. After purification of the digested product, it was inserted into the corresponding sites of the pBC SK(−) cloning vector (Stratagene California; La Jolla, California, USA).

The Up-Replacement arm was synthesized by Blue Heron Biotech (Bothell, Washington, USA). In a 5' to 3' orientation, the synthesized Up-Replacement arm contained nucleotides corresponding to a BamHI restriction endonuclease recognition site, followed by nucleotides 1 to 807 and 1325 to 1341 of the M. haemolytica D153 lktCA gene cluster nucleotide sequence set forth in SEQ ID NO: 1, followed by nucleotides corresponding to an MfeI restriction endonuclease recognition site, followed by a codon-optimized sequence encoding the added leukotoxin neutralizing epitope, followed by nucleotides corresponding to a BamHI restriction endonuclease recognition site. The nucleotide sequence of the synthesized Up-Replacement arm is GGATCCGAAT-TCTCTTTTGCTAAATAGTGTTGGTAAGTAGTCCCAT-TTTGCACACC AATCGTTTTCACCT-TAGCAAAATCTGTATCTTTTTTCGCAATGAAGGCAG CAGAGCTT GGAAAGTAAGGCTCGCTAAATAATACTTGTTTCT-TACGTGGTTCCGTAATACCCATA CCTGAAAT-TGCAGCATCAAATTGTTTTTGTTTTAGGCTTTGGAT-TAAGCTATCAAAAG GTTGGCTATGGAATGTACAATTTGCATTCATCTCTT-TACAGATAGCATTTGCAATATC CACATCAAAACC-GATAATTTCTCCCTTCTCTTCGGTCATTTCAAATG-GAGGATAGCTT GGCTCCATCACAAATTTGA-TATCTTGTGCCTGCGCAGTAAC-CACACACCCGAATAAA AGGGT-CAAAAGTGTTTTTTTCATAAAAAGTCCCTGTGTTTT CATTATAAGGATTACCA CTTTAACGCAGT-TACTTTCTTAAAAAAAGTCTTCTTTTCAT-AAAGTTTGTTTTATGTC ATACAAACACATCAAATT-GAGATGTAGTTTCTCAATCCTCTTGATTCCTCTATCT-CAA AAAAACAACC-CAAAAGAAAAAGAAAAGTATATGTTACATTAAT-ATTACAATGTAA TTATTTTGTTTAATTTCCCTACAT-TTTGTATAACTTTAAAACACTCCTTTTTCTCTTCT GATTATATAAAAGACAAAAAATACAATTTAAGCTA-CAAAAAACAACAAAAAACAAC AAAAAACACGACAATAAGATCGAGTAATGATTAT-ATTATGTTATAATTTTTGACCTA ATTTAGAATAAT-TATAGGAGACATCCCTTATGCAATTGGTAATTA-CAAATAGCAAAA AAGAAAAAGTAACAATTCAAAATTGGTTTCGT-GAAGCAGATTTCGCTAAAGAAGTT CCAAAT-TATAAAGCAACGAAGGATGAAAAAATT-GAAGAAATTATTGGACAAAATGG AGAACGTATTACAAGTAAACAAGTAGATGACT-TAATCGCAAAAGGTAACGGAAAAA TTACTCAG-GATGAATTATCGAAGGTGGTAGATAACTAT-GAAGGATCC, and is set forth in SEQ ID NO: 5. Plasmid pBCSKlktUp-Down was generated by inserting the synthetic Up-Replacement arm into BamH1-digested pBCSK-lktDown. The correct orientation of the Up-Replacement arm was determined using standard Sanger DNA sequencing (performed at the Iowa State University DNA facilities in Ames, Iowa, USA). The resulting pBCSKlktUp-Down plasmid contains the ΔlktCAV4 cassette.

A depiction of the modified lktCA gene cluster cassette is shown in FIG. 1. The top portion of the figure depicts the M. haemolytica leukotoxin lktCA gene cluster, which contains the lkt promotor region (grey arrow); the lktC gene open reading frame (black arrow); the lktC-lktA intergenic region (white arrow); the lktA gene open reading frame (dotted arrow); the added lkt neutralizing epitope (NE, striped slashes), and brackets showing the sections of the lktCA gene cluster to be deleted. The lktA open reading frame includes nucleotides encoding the LktA glycine rich region (GRR, diagonal bricks) and the NE (alternating horizontal dashes). The bottom portion of the figure depicts the M. haemolytica ΔlktCAV4 cassette, which contains the lkt promotor region (grey arrow), having the nucleotide sequence TTCTCTTTTGCTAAA TAGTGTTGGTAAGTAGTCCCATTTTGCACAC-CAATCGTTTTCACCTTAGCAAAATCTG TATCTTTTTTCGCAATGAAGGCAGCAGAGCTTG-GAAAGTAAGGCTCGCTAAATAATA CTTGTTTCT-TACGTGGTTCCGTAATACCCATACCTGAAAT-TGCAGCATCAAATTGTTT TTGTTTTAGGCTTTGGATTAAGCTAT-CAAAAGGTTGGCTATGGAATGTACAATTTGC ATT-CATCTCTTTACAGATAGCATTTGCAATATCCACAT-CAAAACCGATAATTTCTCCC TTCTCTTCGGTCATTTCAAATGGAGGA-TAGCTTGGCTCCATCACAAATTTGATATCTT GTGCCTGCGCAGTAAC-CACACACCCGAATAAAAGGGT-CAAAAGTGTTTTTTTCATAA AAAGTCCCTGTGTTTTCATTATAAGGATTACCACTT-TAACGCAGTTACTTTCTTAAAA AAAGTCTTCTTTT-CATAAAGTTTGTTTTATGTCATACAAACACAT-CAAATTGAGATGT AGTTTCTCAATCCTCTTGATTCCTCTATCT-CAAAAAAAACAACCCAAAAGAAAAAAGA AAAGTATATGTTACATTAATATTACAATGTAATTAT-TTTGTTTAATTTCCCTACATTT TGTATAACTT-TAAAACACTCCTTTTTCTCTTCTGATTATATAAAA-GACAAAAAATACA ATTTAAGCTA-CAAAAAACAACAAAAAACAACAAAAAACACGAC AATAAGATCGAG TAATGATTATATTATGTTATAAT-TTTTGACCTAATTTAGAATAATTAT, which is set forth in SEQ ID NO: 6; the lktC-lktA intergenic region (white arrow), having the nucleotide sequence AAGGAGA-CATCCCTT, set forth in SEQ ID NO: 7; the added codon-optimized lkt NE (striped slashes) having the nucleotide sequence CAATTGGTAATTACAAATAGCAAAA AAGAAAAAGTAACAATTCAAAATTGGTTTCGT-GAAGCAGATTTCGCTAAAGAAGTT CCAAAT-TATAAAGCAACGAAGGATGAAAAAATT-GAAGAAATTATTGGACAAAATGG AGAACGTATTACAAGTAAACAAGTAGATGACT-TAATCGCAAAAGGTAACGGAAAAA TTACTCAG-GATGAATTATCGAAGGTGGTAGATAACTAT-GAAGGATCC, set forth in SEQ ID NO: 8; and leukotoxin A nucleotides 2192 to 3022 CCTTTAACGGTGGT-GATGGTGT CGATACTAT-TGACGGTAACGACGGCAATGACCGCTTAT-TTGGTGGTAAAGGCGATG ATATTCTCGATGGTGGAAATGGTGATGATTTTATC-GATGGCGGTAAAGGCAACGACC TATTA-CACGGTGGCAAGGGCGATGATATTTTCGTT-CACCGTAAAGGCGATGGTAATG ATATTATTACCGATTCTGACGGCAATGATAAATTATCATTCTCTGATTCGAACTTAAA AGATTTAACATTTGAAAAAGTTAAACATAATCTTGTCATCACGAATAGCAAAAAAG AGAAAGTGACCATTCAAAACTGGTTCCGAGAGGCTGATTTTGCTAAAGAAGTGCCT AATTATAAAGCAACTAAAGATGAGAAAATCGAAGAAAT CATCGGTCAAAATGGCGA GCGGATCACCTCAAAGCAAGTTGATGATCTTATCGCAAAAGGTAACGGCAAAATTA CCCAAGATGAGCTATCAAAAGTTGTTGATAACTATGAATTGCTC AAACATAGCAAA AATGTGACAAACAGCTTAGATAAGTTAATCTCATCTGTAAGTGCATTTACCTCGTCT AATGATTCGAGAAATGTATTAGTGGCTCCAACTTCAATGTTGGATCAAAGTTTATCT TCTCTTCAATTTGCTAGAGCAGCTTAATTTTTAATGATTGGCAACTCTATATTGTTTC ACACATTATAGAGTTGCCGTTTTATTTTATAAAAGGAGACAATATGGAAGCTAACCA TCAAAGGAATGATCTTGGTTTAGTTGCCCTCACTATGTTGGCACAATACCATAATAT TTCGCTTAATCCGGAA, set forth in SEQ ID NO: 10, encoding LktA amino acids 731 to 953 (ΔlktA, dotted arrow) ELVITNSKKEKVTIQNWFREADFAKEVPNYKATKDEKIEEIIGQNG ERITSKQVDDLIAKGNGKITQDELSKVVDNYEGSFNGGDGVDTIDGNDGNDRLFGGKG DDILDGGNGDDFIDGGKGNDLLHGGKGDDIFVHRKGDVKDLTFEKVKHNLVITNSKKE KVTIQNWFREADFAKEVPNYKATKDEKIEEIIGQNGERITSKQVDDLIAKGNGKITQDEL SKVVDNYELLKHSKNVTNSLDKLISSVSAFTSSNDSRNVLVAPTSMLDQSLSSLQFARA A*, set forth in SEQ ID NO: 11. ΔLktA comprises nucleotides encoding the LktA GRR (diagonal bricks) and NE (alternating horizontal dashes).

The *M. haemolytica* ΔlktCAV4 cassette has the nucleotide sequence GAATTCTCTTTTGCTAAATAGTGTTGGTAAGTAGTCCCATTTTGCACACCAATCGTTTTCACCTTAGCA AAATCTGTATCTTTTTTCGCAATGAAGGCAGCAGAGCTTGGAAAGTAAGGCTCGCTA AATAATACTTGTTTCTTACGTGGTTCCGTAATACCCATACCTGAAATTGCAGCATCA AATTGTTTTTGTTTTAGGCTTTGGATTAAGCTATCAAAAGGTTGGCTATGGAATGTAC AATTTGCATTCATCTCTTTACAGATAGCATTTGCAATATCCACATCAAAACCGATAA TTTCTCCCTTCTCTTCGGTCATTTCAAATGGAGGATAGCTTGGCTCCATCACAAATTT GATATCTTGTGCCTGCGCAGTAACCACACACCCGAATAAAAGGGTCAAAAGTGTTTT TTTCATAAAAAGTCCCTGTGTTTTCATTATAAGGATTACCACTTTAACGCAGTTACTT TCTTAAAAAAAGTCTTCTTTTCATAAAGTTTGTTTTATGTCATACAAACACATCAAAT TGAGATGTAGTTTCTCAATCCTCTTGATTCCTCTATCTCAAAAAAACAACCCAAAAG AAAAAAGAAAAGTATATGTTACATTAATATTACAATGTAATTATTTTGTTTAATTTCC CTACATTTTGTATAACTTTAAAACACTCCTTTTTCTCTTCTGATTATATAAAAGACAA AAAATACAATTTAAGCTACAAAAAACAACAAAAAACAACAAAAAACACGACA ATA AGATCGAGTAATGATTATATTATGTTATAATTTTTGACCTAATTTAGAATAATTATAG GAGACATCCCTTATGcaattgGTAATTACAAATAGCAAAAAAGAAAAAGTAACAATTCA AAATTGGTTTCGTGAAGCAGATTTCGCTAAAGAAGTTCCAAATTATAAAGCAACGA AGGATGAAAAAATTGAAGAAATTATTGGACAAAATGGAGAACGTATTACAAGTAAA CAAGTAGATGACTTAATCGCAAAAGGTAACGGAAAAATTACTCAGGATGAATTATC GAAGGTGGTAGATAACTATGAAggatccTTTAACGGTGGTGATGGTGTCGATACTATTG ACGGTAACGACGGCAATGACCGCTTATTTGGTGGTAAAGGCGATGATATTCTCGATG GTGGAAATGGTGATGATTTTATCGATGGCGGTAAAGGCAACGACCTATTACACGGT GGCAAGGGCGATGATATTTTCGTTCACCGTAAAGGCGATGGTAATGATATTATTACC GATTCTGACGGCAATGATAAATTATCATTCTCTGATTCGAACTTAAAAGATTTAACA TTTGAAAAAGTTAAACATAATCTTGTCATCACGAATAGCAAAAAAGAGAAAGTGAC CATTCAAAACTGGTTCCGAGAGGCTGATTTTGCTAAAGAAGTGCCTAATTATAAAGC AACTAAAGATGAGAAAATCGAAGAAATCATCGGTCAAAATGGCGAGCGGATCACCT CAAAGCAAGTTGATGATCTTATCGCAAAAGGTAACGGCAAAATTACCCAAGATGAG CTATCAAAAGTTGTTGATAACTATGAATTGCTCAAACATAGCAAAAATGTGACAAAC AGCTTAGATAAGTTAATCTCATCTGTAAGTGCATTTACCTCGTCTAATGATTCGAGA AATGTATTAGTGGCTCCAACTTCAATGTTGGATCAAAGTTTATCTTCTCTTCAATTTG CTAGAGCAGCTTAATTTTTAATGATTGGCAACTCTATATTGTTTCACACATTATAGAG TTGCCGTTTTATTTTATAAAAGGAGACAATATGGAAGCTAACCATCAAAGGAATGAT CTTGGTTTAGTTGCCCTCACTATGTTGGCACAATACCATAATATTTCGCTTAATCCGG AATTC, set forth in SEQ ID NO: 12.

The *M. haemolytica* ΔlktCAV4 cassette encodes the amino acid sequence

MQLVITNSKKEKVTIQNWFREADFAKEVPNYKATKDEKIEEIIGQNGER

ITSKQVDDLIAKGNGKITQDELSKVVDNYEGSFNGGDGVDTIDGNDGND

RLFGGKGDDILDGGNGDDFIDGGKGNDLLHGGKGDDIFVHRKGDGNDII

TDSDGNDKLSFSDSNLKDLTFEKVKHNLVITNSKKEKVTIQNWFREADF

AKEVPNYKATKDEKIEEIIGQNGERITSKQVDDLIAKGNGKITQDELSK

VVDNYELLKHSKNVTNSLDKLISSVSAFTSSNDSRNVLVAPTSMLDQSL

SSLQFARAA*, which is set forth in SEQ ID NO: 13.

To add a selectable marker and a temperature-sensitive origin of replication, the *M. haemolytica* ΔlktCAV4 cassette was inserted in the plasmid pCT109GA189-Kan. Plasmid pCT109GA189-Kan (described in Briggs, R. E. and Tatum, F. M., 2005, *"Generation and Molecular Characterization of New Temperature-Sensitive Plasmids Intended for Genetic Engineering of Pasteurellaceae,"* Appl. Environ. Microbiol. 71(11): 7187-7195) and plasmid pBCSKlktUp-Down were digested with restriction endonuclease enzyme XbaI, treated with Shrimp alkaline phosphatase, and ligated to each other to generate the replacement plasmid pBCΔlktCAV4-pCT109GA189-Kan.

To generate modified *M. haemolytica* D153 (serotype 1) and *M. haemolytica* D174 (serotype 6) bacteria containing the ΔlktCAV4 cassette, the replacement plasmid pBCΔlktCAV4-pCT109GA189-Kan was introduced into *M. haemolytica* D153 (serotype 1) and *M. haemolytica* D174 (serotype 6) using electroporation as described by Briggs, R. E., et al. ("*Characterization of a Restriction Endonuclease, PhaI, from Pasteurella haemolytica Serotype A1 and Protection of Heterologous DNA by a cloned Pha I methyltransferase gene,*" 1994, Appl. Environ. Microbiol. 60(6): 2006-2010) except that the replacement plasmid was not subjected to passage through *E. coli* strain PhaI Mtase. The two *M. haemolytica* strains transformed with the replacement plasmid were treated by the steps described in Tatum, F. M. and Briggs R. E. ("*Construction of In-Frame aroA Deletion Modifieds of Mannheimia haemolytica, Pasteurella multocida, and Haemophilus somnus by Using a New Temperature-Sensitive Plasmid,*" 2005, Appl. Environ. Microbiol. 71(11): 7196-7202) to generate the modified *M. haemolytica* modified products D153ΔlktCAV4 and D174ΔlktCAV4 containing the modified *M. haemolytica* lktCA cassette. These modified *M. haemolytica* strains D153ΔlktCAV4 and D174ΔlktCAV4 are useful as vaccine products.

Example 2

Generation of *M. Bovis* Vaccine Product

A polynucleotide fragment encoding an *M. bovis* Elongation Factor Tu (EF-Tu) and DnaK chimera was inserted into the unique MfeI restriction endonuclease recognition site of the *M. haemolytica* ΔlktCAV4 cassette to generate ΔlktCAV4Mbovis cassette.

A synthetic polynucleotide fragment encoding an *M. bovis* EF-Tu/DnaK chimera, having the nucleotide sequence CAATTGATGAACGCGGTCGATACATGGATTGAGACACCTGTT AAAGATTTCGAGAAACCGTTCTTAATGGCGGTAGAAGACGTGTTTACAATTTCAGGT CGTGGCACCGTTGCAACAGGTCGTGTAGAACGTG GACGCTTAAGTTTAAATGAGGA AGTGGAGATTGTAGGTTTAAAGCCCACTAAAAAAACAGTCGTTACAGGTATCGAAA TGTTTCGCAAAAACTTAAAAGAAGCCCAAGCAGGAGATAACGCAGGTTT ATTATTA CGTGGAGTTGAACGCAGTGCCATTGAACGTGGTCAAGTATTAGCAAAACCAGGGAG TATCGTTCCTCATGCCGAATTTGAAGCCGCCATTTATGCATTGACAAAAGAAGAAGG CGGACGTCATACTCCGTTTTTCGTAAACTATAAACCTCAATTTTATTTCCGTACAACA GATGTGACTGGTGGCCTTGAGTTTGAGAAAGGACGTGAATTTGTACAACCGGGAGA AAATGTCAACTTGAAAGTAAAATTAATTGCACCAATCGCCGTAGAGGAAGGAACAA AATTCAGTATTCGTGAAGGTGGGCGCACAGTAGGGTATGGTAGTGTAAC TAAAATTT TAAAGTTAGTCGATGTAACCCCTTTAACTTTAGGTATTGAAACAGCAGGCGGCATTG CAACCCCTTTAATCCCACGTAACACTCGTATTCCCATTACAAAGTCAGAAGTTTTTAC AACGTTTGAAGATAACCAAAGTGAAGTAACAATTCGTATCGTGCAAGGTGAACGTC CATTAGCGTCTGAAAATAAATTATTAGGACAATTTAACTTAGGTGGAATCCGTATCG CACCCCGTG GAGTACCTCAAATCGAAGTCAGTTTCAAAATCGATGCAAACGGCATTA CGACAGTATTAGCAAAAGATAAAGATACCAACAAAGAACAATCTATTACAATTAAA AACAGCTCTAAATTAAGTGACGCAGAAATCGAAGAAATGATCAAAGATGCAGAAAA AAACCGTGAAGCAGATGCCAAACGTGCCGAAGAAATTAGTACAATTATTCAAGCAG AAAACTTAGTAAACTCATTAGAAAAAGAAATGAACGAAGGTAACATTGTAATTCCA GAAGAAGAAAAAACTAAAATCGCCGAATATATTAAAGAAGTAAAAGAGTTAATCA ACAATAAAGATGTAGAACAATTAAAAAAGAAAATTGATGAATTAAACGCAGCATAT AATATGGCCAAATCAGCAGCAGCCTCAGCAAATAAAGATGATAGTAGTAATTCGGA TGAAGAAACTTTCGAATTC, set forth in SEQ ID NO: 18, was synthesized by Blue Heron Biotech (Bothell, Washington, USA). In a 5' to 3' orientation, the synthetic polynucleotide fragment contains nucleotides corresponding to a codon-optimized nucleotide sequence encoding a segment of *M. bovis* EF-Tu having the nucleotide sequence ATGAACGCGGTCGATA CATG GATTGAGACACCTGTTAAAGATTTCGAGAAACCGTTCT TAATGGCGGTAGAAGACGT GTTTACAATTCAGGTCGTGGCACCGTTGCAACAGGTCGTGTA GAACGTGGACGCTT AAGTTTAAATGAGGAAGTGGAGATTGTAGGTTTAAAGCCCACTAAAAAAACAGTCG TTACAGGTATCGAAATGTTTCGCAAAAACTTAAAAGA AGCCCAAGCAGGAGATAAC GCAGGTTTATTATTACGTGGAGTTGAACGCAGTGCCATTGAACGTGGTCAAGTATTA GCAAAACCAGGGAGTATCGTTCCTCATGCCGAATTTGAAGCCGCCATTTATGCATTG ACAAAAGAAGAAGGCGGACGTCATACTCCGTTTTTCGTAAACTATAAACCTCAATTT TATTTCCGTACAACAGATGTGACTGGTGGCCTTGAGTTTGAGAAAGGACGTGAATTT GTACAACCGGGAGAAAATGTCAACTTGAAAGTAAAATTAATTGCACCAATCGCCGT AGAGGAAGGAACAAAATTCAGTATTCGTGAAGGTGGGCGCACAGTAGGGTATGGTA GTGTAACTAAAATTTTAAAG, set forth in SEQ ID NO: 14, followed by a codon-optimized nucleotide sequence encoding a segment of *M. bovis* DnaK having the nucleotide sequence TTAGTCGATGTAACCCCTTTAACTTTAGGTATTGAAACAGCAGGCGGCATTGCAACC CCTTTAATCCCACGTAACACTCGTATTCCCATTACAAAGTCAGAAGTTTTTACAACGT TTGAAGATAACCAAAGTGAAGTAACAATTCGTATCGTGCAAGGTGAACGTCCATTA GCGTCTGAAAATAAATTATTAGGACAATTTAACTTAGGTGGAATCCGTATCGCACCC CGTGGAGTACCTCAAATCGAAGTCAGTTTCAAAATCGATGCAAACGGCATTACGAC AGTATTAGCAAAAGATAAAGATACCAACAAAGAACAATCTATTACAATTAAAAACA GCTCTAAATTAAGTGACGCAGAAATCGAAGAAATGATCAAAGATGCAGAAAAAAAC CGTGAAGCAGATGCCAAACGTGCCGAAGAAATTAGTACAATTATTCAAGCAGAAAA CTTAGTAAACTCATTAGAAAAAGAAATGAACGAAGGTAACATTGTAATTCCAGAAG AAGAAAAAACTAAAATCGCCGAATATATTAAAGAAGTAAAAGAGTTAATCAACAAT AAAGATGTAGAACAATTAAAAAAGAAAATTGATGAATTAAACGCAGCATATAATAT GGCCAAATCAGCAGCAGCCTCAGCAAATAAAGATGATAGTAGTAATTCGGATGAAG AAACTTC, set forth in SEQ ID NO: 16. The synthetic polynucleotide fragment contains nucleotides corresponding to an MfeI restriction endonuclease recognition site at the 5' end, and nucleotides corresponding to an EcoRI restriction endonuclease recognition site at the 3' end.

The synthetic *M. bovis* EF-Tu/DnaK fragment was digested with MfeI and EcoRI, and inserted into MfeI-digested *M. haemolytica* replacement plasmid pBCΔlktCAV4 to generate plasmid pBCΔlktCAV4Mbovis. The correct orientation of the inserted *M. bovis* EF-Tu/DnaK fragment in the plasmid pBCΔlktCAV4Mbovis was determined using standard Sanger DNA sequencing. The nucleotide sequence of ΔlktCAV4Mbovis, a modified lktCA cassette with the *M. bovis* antigen is GGATCCGAAT-TCTCTTTTGCTAAATAGTGTTGGTAAGTAGTCCC ATTTTGCACACCAATCGTTTTCACCT-TAGCAAAATCTGTATCTTTTTTCGCAATGAAG GCAGCAGAGCTTG-GAAAGTAAGGCTCGCTAAATAATACTTGTTTCT-TACGTGGTTCC GTAATACCCATACCTGAAAT-TGCAGCATCAAATTGTTTTTGTTTAGGCTTTGGAT TA AGCTATCAAAAGGTTGGCTATGGAATGTACAAT-TTGCATTCATCTCTTTACAGATAG CAT-TTGCAATATCCACATCAAAACCGATAAT-TTCTCCCTTCTCTTCGGTCATTTCAAA TGGAGGATAGCTTGGCTCCATCACAAATTTGA-TATCTTGTGCCTGCGCAGTAACCAC ACACCCGAATAAAAGGGTCAAAAGTGTTTTTTT-CATAAAAAGTCCCTGTGTTTTCAT TATAAGGATTAC-CACTTTAACGCAGTTACTTTCT-TAAAAAAAGTCTTCTTTTCATAAA GTTTGTTTTATGTCATACAAACACATCAAATT-GAGATGTAGTTTCTCAATCCTCTTGA TTCCTC-TATCTCAAAAAAACAACC-CAAAAGAAAAAAGAAAAGTATATGTTACATTA ATATTACAATGTAATTATTTTGTTTAATTTCCCTA-CATTTGTATAACTTTAAAACAC TCCTTTTTCTCTTCTGATTATATAAAA-GACAAAAAATACAATTTAAGCTACAAAAAA CAACAAAAAACAACAAAAAACACGACAATAA-GATCGAGTAATGATTATATTATGTT ATAAT-TTTTGACCTAATTTAGAATAATTATAGGAGA-CATCCCTTATGcaattgATGAACG CGGTCGATACATGGATTGAGACACCTGTTAAAGAT-TTCGAGAAACCGTTCTTAATGG CGGTAGAA-GACGTGTTTACAAT-TTCAGGTCGTGGCACCGTTGCAACAGGTCGTGTAG AACGTGGACGCTTAAGTTTAAATGAGGAAGTG-GAGATTGTAGGTTTAAAGCCCACT AAAAAAACAGTCGTTA-CAGGTATCGAAATGTTTCGCAAAAACT-TAAAAGAAGCCCA AGCAGGAGATAACGCAGGTTT-ATTATTACGTGGAGTTGAACGCAGTGCCATTGAAC GTGGTCAAGTATTAGCAAAACCAGG-GAGTATCGTTCCTCATGCCGAATTTGAAGCCG CCATTTATGCATTGACAAAAGAAGAAGGCGGACGT-CATACTCCGTTTTTCGTAAACT ATAAACCTCAATTT-TATTTCCGTACAACAGATGTGACTGGTGGCCTT-GAGTTTGAGA AAGGACGTGAATTTGTACAACCGGGAGAAAATGT-CAACTTGAAAGTAAAATTAATT GCAC-CAATCGCCGTAGAGGAGGAACAAAATTCAGTAT-TCGTGAAGGTGGGCGCAC AGTAGGGTATGGTAGTGTAACTAAAATTTTAAAGT-TAGTCGATGTAACCCCTTTAAC TTTAGGTATT-GAAACAGCAGGCGGCATTGCAACCCCTTTAATCC-CACGTAACACTCG TATTCCCATTACAAAGTCAGAAGTTTTTA-CAACGTTTGAAGATAACCAAAGTGAAGT AACAAT-TCGTATCGTGCAAGGTGAACGTCCATTAGCGTCT-GAAAATAAATTATTAGG ACAATTTAACTTAGGTG-GAATCCGTATCGCACCCCGTGGAGTACCT-CAAATCGAAGT CAGTTTCAAAATC-GATGCAAACGGCATTACGACAGTATTAGCAAAAGA-TAAAGATA CCAACAAAGAACAATCTATTACAAT-TAAAAACAGCTCTAAATTAAGTGACGCAGAA ATCGAAGAAATGATCAAA-GATGCAGAAAAAAACCGTGAAGCAGATGC-CAAACGTG CCGAAGAAATTAGTACAATTATT-CAAGCAGAAAACTTAGTAAACTCATTAGAAAAA GAAATGAACGAAGGTAACATTGTAAT-TCCAGAAGAAGAAAAAACTAAAATCGCCGA ATAT-ATTAAAGAAGTAAAAGAGTTAATCAACAATAAA-GATGTAGAACAATTAAAAA AGAAAATTGATGAATTAAACGCAG-CATATAATATGGCCAAATCAGCAGCAGCCTCA GCAAATAAAGATGATAGTAGTAATTCGGAT-GAAGAAACTTTCgaattgGTAATTACAAA TAGCAAAAAAGAAAAAAGTAACAATTCAAAAT-TGGTTTCGTGAAGCAGATTTCGCTA AAGAAGTTC-CAAATTATAAAGCAACGAAGGATGAAAAAATT-GAAGAAATTATTGGA CAAAATGGAGAACGTATTACAAGTAAACAAGTA-GATGACTTAATCGCAAAAGGTAA CGGAAAAAT-TACTCAGGATGAATTATCGAAGGTGGTAGATAAC-TATGAAGGATCCT TTAACGGTGGTGATGGTGTCGATACTAT-TGACGGTAACGACGGCAATGACCGCTTAT TTGGTGGTAAAGGCGATGATATTCTCGATGGTG-GAAATGGTGATGATTTTATCGATG GCGGTAAAGGCAACGACCTATTA-CACGGTGGCAAGGGCGATGATATTTTCGTTCACC GTAAAGGCGATGGTAATGATATTATTACCGAT-TCTGACGGCAATGATAAATTATCAT TCTCTGAT-TCGAACTTAAAAGATTTAACATTTGAAAAAGT-TAAACATAATCTTGTCA TCACGAATAGCAAAAAAGAGAAAGTGACCATT-CAAAACTGGTTCCGAGAGGCTGAT TTTGCTAAAGAAGTGCCTAAT-TATAAAGCAACTAAAGATGAGAAAATCGAAGAAAT CATCGGTCAAAATGGCGAGCGGATCACCT-CAAAGCAAGTTGATGATCTTATCGCAA AAGGTAACGGCAAAATTACCCAAGATGAGCTAT-CAAAAGTTGTTGATAACTATGAA TTGCTCAAACAT-AGCAAAAATGTGACAAACAGCTTAGATAAGT-TAATCTCATCTGTA AGTGCATTTACCTCGTCTAATGATTCGAGAAATGT-ATTAGTGGCTCCAACTTCAATG TTGGATCAAAGTT-TATCTTCTCTTCAATTTGCTAGAGCAGCTTAATTTT-TAATGATTG GCAACTCTATATTGTTTCACACAT-TATAGAGTTGCCGTTTTATTTTATAAAAGGAGAC AATATGGAAGCTAACCATCAAAGGAAT-GATCTTGGTTTAGTTGCCCTCACTATGTTG GCACAATACCATAATATTTCGCTTAATCCGGAATTC, and is set forth in SEQ ID NO: 20.

The amino acid sequence of the polypeptide encoded by ΔlktCAV4Mbovis cassette is MQLMNAVDTWIETPVKD-FEKPFLMAVEDVFTIS GRGTVATGRVERGRLSL-NEEVEIVGL KPTKKTVVTGIEMFRKNLKEAQAGD-NAGLLLRGVERSAIERGQVLAKPGSIVPHAEFEA AIYALTKEEGGRHTPFFVNYKPQFYFRTTDVTG- GLEFEKGREFVQPGENVNLKVKLIAPI AVEEGTKF-
SIREGGRTVGYGSVTKILKLVDVTPLTLGIETAG-
GIATPLIPRNTRIPITKSEVF
TTFEDNQSEVTIRIVQGERPLASENKLLGQFNLGGIR-
IAPRGVPQIEVSFKIDANGITTVLA KDKDTNKEQSI-
TIKNSSKLSDAEIEEMIKDAEKNREADAKRAEEIS-
TIIQAENLVNSLEKE
MNEGNIVIPEEEKTKIAEYIKEVKELINNKDVEQLKK-
KIDELNAAYNMAKSAAASANKD DSSNSDEET-
FELVITNSKKEKVTIQNWFREADFAKEV-
PNYKATKDEKIEEIIGQNGERITS
KQVDDLIAKGNGKITQDEL-
SKVVDNYEGSFNGGDGVDTIDGNDGN-
DRLFGGKGDDILD GGNGDDFIDG-
GKGNDLLHGGKGDDIFVHRKGDGNDIITDSDGNDK
LSFSDSNLKDLTFE KVKHNLVITNSKKEKV-
TIQNWFREADFAKEVPNYKATKDEKIEEIIGQNGER-
ITSKQVDD LIAKGNGKITQDELSKVVDNYELLKHS-
KNVTNSLDKLISSVSAFTSSNDSRNVLVAPTSM
LDQSLSSLQFARAA*, and set forth in SEQ ID NO: 21.
The codon-optimized nucleotide sequence encoding M.
bovis EF-Tu/DnaK chimera encodes the amino acid
sequence QLMNAVDTWIETPVKDFEKPFL-
MAVEDVFTISGRGTVATGRVERGRLSLNEEVEIVGLK
PTKKTVVTGIEMFRKNLKEAQAGDNAGLLLRGVER-
SAIERGQVLAKPGSIVPHAEFEAAI YALTKEEG-
GRHTPFFVNYKPQFYFRTTDVTGGLEFEKGREFVQP-
GENVNLKVKLIAPIA
VEEGTKFSIREGGRTVGYGSVTKILKLVDVTPLTLGI-
ETAGGIATPLIPRNTRIPITKSEVFT TFEDNQ-
SEVTIRIVQGERPLASENKLLGQFNLGGIR-
IAPRGVPQIEVSFKIDANGITTVLAK
DKDTNKEQSITIKNSSKLSDAEIEEMIKDAEKN-
READAKRAEEISTIIQAENLVNSLEKEM NEGNIVI-
PEEEKTKIAEYIKEVKELINNKDVEQLKKKIDEL-
NAAYNMAKSAAASANKDD SSNSDEETFEF, which is
set forth in SEQ ID NO: 19.

FIG. 2 depicts a schematic of the construction of the ΔlktCAV4Mbovis cassette from the ΔlktCAV4 cassette. The top portion of the figure shows the *M. haemolytica* ΔlktCAV4 cassette, which contains the lkt promotor (grey arrow); the lktC-lktA intergenic region (white arrow); and lktA nucleotides 2192 to 3022 (ΔlktA, dotted arrow) comprising the inserted synthetic polynucleotide encoding leukotoxin NE (striped slashes); the polynucleotide encoding leukotoxin GRR (diagonal bricks); and the polynucleotide encoding the native NE (alternating horizontal dashes). The polynucleotides encoding EF-Tu and DnaK are depicted above the *M. haemolytica* ΔlktCAV4 cassette. The bottom portion of the figure shows the ΔlktCAV4Mbovis cassette.

To add a selectable marker and a temperature-sensitive origin of replication, plasmids pBCΔlktCAV4Mbovis and pCT109GA189-Kan were digested with restriction endonuclease enzyme XbaI, treated with Shrimp alkaline phosphatase, and ligated to each other to generate the plasmid pBCΔlktCAV4Mbovis-pCT109GA189-Kan. To generate modified *M. haemolytica* D153 (serotype 1) and *M. haemolytica* D174 (serotype 6) containing the ΔlktCAV4Mbovis cassette, the replacement plasmid pBCΔlktCAV4Mbovis-pCT109GA189-Kan was introduced into *M. haemolytica* D153 (serotype 1) and *M. haemolytica* D174 (serotype 6) using electroporation as described in Example 1, above. The two *M. haemolytica* strains transformed with the plasmid containing nucleotides encoding EF-Tu and DnaK were treated by the steps described above in Example 1, to generate D153ΔlktCAV4Mbovis vaccine product and D174ΔlktCAV4Mbovis vaccine product.

Example 3

Cattle Vaccination for *Mycoplasma* Challenge

Calves were vaccinated with a mixture of D153ΔlktCAV4 and D174ΔlktCAV4; or a mixture of ΔlktCAV4Mbovis and D174ΔlktCAV4Mbovis, followed by challenge with *M. bovis* isolate KRB5. After challenge, cattle vaccinated with a mixture of ΔlktCAV4Mbovis and D174ΔlktCAV4Mbovis showed little to no *M. bovis* lung load, while cattle vaccinated with a mixture of D153ΔlktCAV4 and D174ΔlktCAV4 showed a high *M. bovis* lung load.

Twelve Holstein calves, approximately 40 days of age and started on solid feed, were enrolled in the study. The calves had been caught, colostrum deprived, and were isolated in individual hutches until shipment to the USDA's National Animal Disease Center (NADC). Upon arrival the calves were randomly allocated to 2 groups (n=6 per group) housed indoors in a climate-controlled biocontainment facility. Each group was divided among 3 rooms, for a total of 6 rooms, with 2 calves in each room. The calves were fed twice per day calf starter (Calf STARTENA; Purina Mills, Gray Summit, Missouri, USA) and hay cubes as much as they would clean up before the next feeding. Fresh water was provided ad libitum.

Six days post arrival (designated day 0) the calves were vaccinated by intranasal instillation of the above experimental vaccine preparations. Group 1 calves received *M. haemolytica* ΔlktCAV4 vaccine product (vaccine without *M. bovis* antigen payload), while Group 2 calves received ΔlktCAV4Mbovis vaccine product (vaccine with *M. bovis* antigen payload).

Serotype 1 and serotype 6 modified-live *M. haemolytica* strains D153ΔlktCAV4 and D174ΔlktCAV4 prepared as in Example 1, and the D153ΔlktCAV4Mbovis and D174ΔlktCAV4Mbovis vaccine products prepared as in Example 2, were grown overnight on Columbia agar plates with 5% defibrinated bovine blood (4 total cultures). Pure culture growth was harvested with DACRON polyester fiber (Du Pont de Nemours and Company, Wilmington, Delaware, USA) swabs, and each inoculated into 50 mL Columbia broth (in 200 mL Erlenmeyer flasks) until an OD 600 of 0.1 was achieved. The flasks were incubated at 37° C. with shaking at 200 rpm until an OD 600 of approximately 0.4 was achieved, at which point 25 mL of each culture was transferred to a 50 mL conical tube and placed on ice for transport to the animal barn. At the barn, two inocula were formed by combining serotype 1 and serotype 6 of modified-live *M. haemolytica* ΔlktCAV4 and of ΔlktCAV4Mbovis vaccine product. An aliquot of each inoculum was returned to the laboratory for quantitative culture and PCR analysis.

The inoculum with *M. haemolytica* ΔlktCAV4 was determined to contain $3.5 \times 10^8$ CFU/mL for a total dose of $1.4 \times 10^9$ CFU per calf. Twenty representative colonies were tested by PCR and were determined to be evenly divided between *M. haemolytica* serotype 1 and *M. haemolytica* serotype 6. All were confirmed to contain the expected changes in the *M. haemolytica* lktCA gene cluster, and not to contain *M. bovis* insert. The inoculum with ΔlktCAV4Mbovis was determined to contain $3.9 \times 10^8$ CFU/mL for a total dose of $1.6 \times 10^9$ CFU per calf. Nearly two thirds of the inoculum was determined to be serotype 6 and all representative colonies were confirmed to contain the expected changes in the *M. haemolytica* lktCA gene cluster, and to contain the *M. bovis* insert.

Four mL of the vaccine was deposited, 2 mL per nostril, utilizing a MAD NASAL, intranasal mucosal atomization device (Teleflex; Limerick, Pennsylvania, USA) attached to a 5 mL disposable syringe. The devices were reused for calves within each room, but new devices were used in each successive room. An aliquot of each challenge inoculum was placed on ice prior to mixing and afterwards for quantitative culture.

Example 4

Challenge with *M. Bovis*

This example shows that vaccination with D153ΔlktCAV4Mbovis and D174ΔlktCAV4Mbovis vaccine products protect cattle from *M. bovis* challenge.

All calves were observed twice daily for general health, appetite, and demeanor, for the duration of the experiment. Following *Mycoplasma* challenge an additional daily observation time point was included, for a total of 3 observations per day, which were continued for the remainder of the experiment. Jugular blood (for serum), nasal swabs (for culture, aspirated nasal mucus (for ELISA), tonsil wash specimens (for culture), and tears (for ELISA) were collected weekly. Rectal temperatures were collected 3 times daily following BHV-1 challenge until necropsy.

A two phase challenge system was utilized which employed bovine herpesvirus 1 (BHV-1) pre-challenge in an effort to predispose to virulent *M. bovis* challenge. On day 34 post vaccination all calves were exposed to $10^{8.2}$ total TCID50 BHV-1 Cooper (kindly supplied by National Veterinary Services Laboratories, Ames, Iowa, USA) in a volume of 4 mL (2 mL per nostril) using MAD NASAL devices as above. Four days later all calves were exposed to *M. bovis* isolate KRB5 (kindly supplied by Dr. Karen Register, National Animal Disease Center (NADC); Ames, Iowa, USA). Five mL of the challenge *Mycoplasma* were delivered, 2.5 mL per nostril, using MAD NASAL devices as above.

The KRB5 isolate was recovered in 2014 from pneumonic lung of a Kansas (USA) feedlot calf and identified as *M. bovis* based on colony morphology and species-specific PCR. The isolate was grown for 24 hours at 37° C. in PPLO, selective *Mycoplasma* media (BD Diagnostic Systems; Hunt Valley, Maryland, USA) supplemented with 10 g/L yeast extract (BD Diagnostic Systems) and 20% horse serum (Life Technologies; Carlsbad, California, USA) in a 5% $CO_2$ atmosphere. The resultant bacteria were pelleted by centrifugation at 15,000×g for 20 minutes, followed by resuspension in 1/100th of the original volume in PPLO broth. The suspension was gently passed through a 25-gauge needle, aliquoted, snap-frozen in dry ice/ethanol bath, and stored at −80° C. An aliquot was thawed, serially diluted, and plated on PPLO agar in triplicate to determine bacterial titer. On the day of *M. bovis* challenge an aliquot was thawed and diluted in PPLO broth to achieve a concentration of $2 \times 10^9$ CFU/mL.

A semi-quantitative technique was used for bacterial specimen culture whereby nasal swabs were struck in a consistent manner on the primary zone of blood agar plates, then a sterile loop was used to generate secondary and tertiary zones. Tonsil wash specimens were cultured in a similar manner. The specimens were briefly sonicated, then a sterile swab was dipped and struck as with the nasal swabs. Following overnight incubation, suspect colonies were enumerated, and representative colonies were passed for PCR confirmation of identity and serotype.

With respect to colonization and shedding of vaccine strains, nasal swabs yielded generally little or no *M. haemolytica*. Two out of 6 calves in Group 1 (vaccine with no *M. bovis* payload) yielded *M. haemolytica* serotype 1, serotype 6, or both on day 3, 7 and 21, skipping day 14. Two out of 6 calves in Group 2 (vaccine with *M. bovis* payload) yielded *M. haemolytica* serotype 6 on day 3, and were nasal culture-negative thereafter. All recovered colonies were confirmed by PCR to contain the expected changes in the lktCA gene cluster. Tonsil wash specimens yielded much higher bacterial numbers for a longer period of time. Group 1 calves yielded moderate to high bacterial numbers (numerous colonies in secondary or tertiary zones of the plates) on day 3. Bacterial numbers slowly diminished over successive weeks to become low (isolated colonies in primary zone) to moderate recovery of mixed serotype on Day35. Only one Group 1 calf ceased shedding at day 35. Group 2 calves yielded similar moderate to high numbers of *M. haemolytica* at day 3, which slowly diminished to low numbers on day 35. Initial recovery was mixed with respect to serotype, but serotype 6 become more prominent over time until only serotype 6 was recovered on day 35. Two Group 2 calves ceased shedding on day 35. All representative isolates were confirmed to contain the expected genetic deletion in the lktCA gene cluster.

Group 1 and Group 2 calves became febrile 3 days following BHV-1 challenge, the highest individual temperature reaching 41.3 C in Group 2 (vaccinated with ΔlktCAV4Mbovis). As seen in FIG. 3, at the time of *Mycoplasma* challenge both groups were febrile. Rectal temperatures generally declined on successive days with an inflection point for Group 1 (vaccinated with ΔlktCAV4) at 10 days post-BHV-1 challenge and Group 2 (vaccinated with ΔlktCAV4Mbovis) at 8 days post-BHV-1 challenge. Starting 8 days post-BHV-1 challenge, and for several days thereafter, Group 2 calves exhibited lower rectal temperatures than did those of Group 1, significantly ($P<0.05$). A graph of the mean rectal temperature of calves challenged with BHV-1, and four days later challenged with *M. bovis* is depicted on FIG. 3. Results for calves vaccinated with *M. haemolytica* ΔlktCAV4 are labeled Group 1; and results for calves vaccinated with ΔlktCAV4Mbovis vaccine product are labeled Group 2.

Three calves in Group 1 exhibited tachypnea, depression, drooped ears and head-tilt beginning 2 days post-*Mycoplasma* challenge for 2 calves, and beginning 7 days post-*Mycoplasma* challenge for the third. One Group 1 calf exhibited a crusty right eye beginning 12 days after *Mycoplasma* challenge. Some increase in nasal discharge was noted in both groups of calves starting 3 days post-*Mycoplasma* challenge and extending up to 8 days post-challenge.

Three Group 1 calves were euthanized before schedule due to reaching clinical endpoints (July 5, 13 days post-*M. bovis* challenge). Of these calves, one did not exhibit gross lung lesions, while the other two exhibited multifocal lesions involving multiple lobes. While the left middle lobe of one calf showed 50% involvement, the percentage involvement was generally modest. These early-euthanized calves yielded 0.0, 3.7%, and 1.5% lung involvement respectively when lesion volume was multiplied by individual lobe contribution to air exchange. Tympanic bullae from all these calves were filled with purulent to gaseous material.

The calves euthanized on-schedule generally showed minor or no lung lesions. Two additional Group 1 calves were found to contain small lesions in one or two lobes totaling 0.05% and 0.03% of total air exchange, while one calf did not show any visible lesions. Tympanic bullae of these 3 Group 1 calves were grossly normal. Group 2 calves fared a bit better with respect to gross lung lesions. Five of 6 showed no visible lesions, while 1 calf evidenced one minor lesion in the right caudal lobe totaling 0.035% of air exchange. One Group 2 calf exhibited unilateral involvement of the tympanic bullae.

Quantitative culture of affected and unaffected lung tissue demonstrated dramatic differences between the calves in Group 1 and Group 2 with respect to infectious *Mycoplasma bovis* lung loading. As seen in FIG. 4, geometric mean *Mycoplasma bovis* recovery from Group 1 lung was $10^{4.2}$ CFU/gram (17000 CFU/gram) in Group 1 whereas geometric mean recovery from Group 2 was $10^{0.32}$ CFU/gram (2 CFU/gram). Six of 6 Group 1 calves yielded culture-positive lung specimens whereas only 2 of 6 Group 2 calves yielded culture-positive lung specimens. Recovery of *M. bovis* from Group 1 calves was compared between individual specimens from lesion vs non-lesion regions. Lesion lung geometric mean titer was $10^{4.4}$ CFU/gram while non-lesion lung was $10^{4.1}$ CFU/gram (P=0.73). A graph of the quantitative *M. bovis* recovery from lung is depicted on FIG. 4. Results for calves vaccinated with M *haemolytica* ΔlktCAV4 are labeled Group 1 and results for calves vaccinated with ΔlktCAV4Mbovis vaccine product are labeled Group 2. Two Group 1 calves yielded *M. bovis* from hock joints; these two calves were not among the calves euthanized early related to symptomatic middle ear disease. No *M. bovis* was recovered from the hocks of Group 2 calves.

Histopathologic findings were generally consistent with gross findings. Examination of lung specimens revealed bronchopneumonia in multiple lobes of 3 Group 1 calves, two of which had been euthanized early due to clinical presentation, and one which was euthanized on-schedule. The remaining three Group 1 calves consistently showed interstitial thickening in all lobes examined without evidence of pneumonia. In Group 2 calves, the minor gross lesion detected in the caudal lobe of a single calf was confirmed to be bronchopneumonia. Three Group 2 calves variably evidenced interstitial thickening without evidence of pneumonia or no significant lesion found. Two Group 2 calves evidenced no significant lesion in any lobe examined.

Examination of tympanic bullae revealed bilateral necrotizing otitis media in three of the six Group 1 calves. The remaining three Group 1 calves showed no significant lesion in tympanic bullae. One Group 2 calf evidenced unilateral necrotizing otitis media with the opposing middle ear (which had appeared grossly normal) exhibiting lymphocytic otitis media. The remaining five Group 2 calves showed no significant lesion in middle ears.

Indirect ELISA was conducted using recombinant *Mycoplasma bovis* EF-Tu produced in *E. coli* and anti-bovine IgG whole molecule secondary antibody. The results are shown in FIG. 5. Group 1 calves exhibited steady low antibody titers until the time of BHV-1 challenge, then trended slightly upwards largely associated with the response of a single calf. Group 2 antibody titers trended upwards throughout the trial, becoming significantly higher (P<0.05) 7 days post vaccination and remaining significantly higher than Group 1 thereafter.

T-test for lung lesion P=0.094; Fisher exact number of involved middle ears P=0.034; Fisher exact number of calves with systemic *Mycoplasma* infection (middle ear or joint) P=0.040; T-test log lung load P=3.3E-07; T-test for rectal temperatures between June 26 and euthanasia P=0.0030.

Mucosal (intranasal) exposure to modified-live *Mannheimia haemolytica* resulted in nasopharyngeal colonization by the organism and a significant systemic immunological response. In this particular trial serotype 6 *Mannheimia haemolytica* colonized to a higher degree than did serotype 1, underscoring the potential importance of combining these serotypes for usage as vaccine vectors to improve the odds of successful colonization and therefore immune response. The antibody response to the *Mycoplasma bovis* antigen payload increased steadily throughout the trial, becoming significantly higher in Group 2 animals when compared to Group 1 (control) animals as early as 7 days post-vaccination. The antibody response to the *Mycoplasma bovis* antigen payload remained higher in Group 2 calves through the remainder of the trial.

BHV-1 viral challenge was utilized to predispose to *Mycoplasma bovis* disease; failure of *Mycoplasma bovis* challenge alone to elicit clinical disease in calves is a frequent problem faced by researchers. BHV-1 is known to elicit a significant febrile response during clinical infection starting on days 3 or 4 following challenge. The current results are consistent with that observation where febrile calves were observed 3 days following BHV-1 challenge. *Mycoplasma* was delivered on day 4 following BHV-1 challenge at the peak of fever. Interestingly, the vaccinated calves recovered more quickly with respect to rectal temperatures. Non-vaccinated calves' rectal temperatures remained elevated longer than did those of vaccinates, significantly higher for the period of 2 weeks prior to euthanasia (P=0.0030). Pneumonic *Mycoplasma* disease in calves is generally associated with mild symptoms with only modest elevation in body temperature, often below 40° C. above which many producers would consider antimicrobial treatment. The more rapid decline in body temperatures of vaccinates are likely a reflection of improved control of *Mycoplasma* infection among vaccinated animals.

Recovery of live *Mycoplasma* from individual lung specimens at post-mortem was strikingly reduced among vaccinates. All non-vaccinated animals yielded multiple lung specimens which contained in excess of 1000 CFU/gram *Mycoplasma bovis* (ranging up to over a million CFU/gram), whereas no vaccinate yielded any lung specimen exceeding 1000 CFU/gram. Four of 6 vaccinates yielded only sterile lung specimens, the other two calves yielded low numbers from one or more lung specimens. Geometric mean lung loading was reduced approximately 1000-fold among vaccinates (P<3.4E-07). It is likely that reduced infectious lung load is associated with reduced risk of lung disease.

Middle ear infection, otitis media, and joint disease are known sequalae of *Mycoplasma bovis* infection. Nevertheless, the relatively high incidence observed in this particular trial is notable. Five of 6 non-vaccinates exhibited either middle ear infection or joint infection while one vaccinate exhibited middle ear infection (P<0.05). Three of the non-vaccinates were euthanized prior to schedule due to symptoms associated with otitis media. It may be that the BHV-1 challenge did predispose to disease as intended with effects which extended to peripheral sites.

Vaccination was associated with reductions in numbers of calves exhibiting lung disease and the percentage involvement of lung. Vaccination was also associated with reductions in numbers of calves exhibiting lung disease and the percentage involvement of lung. With the relatively small group size, however, neither of these reductions were significant at the P<0.05 level. T-test for reduction in lung lesion was P=0.094; Fisher Exact test for numbers of calves with detectable *Mycoplasma* lesions was P=0.12. Given the very large observed difference in infectious lung loading by *Mycoplasma* between vaccinates and non-vaccinates, it is likely that larger experimental groups will yield improved statistical evidence of vaccine efficacy.

Example 5

Identification of Recovered M. Haemolytica

Representative isolates of M. haemolytica recovered from nasal swabs and from palatine tonsils of calves challenged in Example 4 were positively identified using PCR analyses.

A primer pair spanning the lktCA deletion and inserted synthetic leukotoxin neutralizing epitope, ΔlktCAV4diag, was utilized. The forward diagnostic primer anneals approximately 270 bp upstream of the MfeI site; the reverse diagnostic primer anneals approximately 60 bp downstream of the BamH1 site. The sequence of the forward primer ΔlktCAV4diagF is 5'-gttctcaatcctcttgattcctc-3' and is set forth in SEQ ID NO: 22; the sequence of the reverse primer ΔlktCAV4diagR is 5'-gttaccgtcaatagtatcgcacacc-3' and is set forth in SEQ ID NO: 23. Amplification products of 571 base pairs were expected for either M. haemolytica serotype 1 or serotype 6 bacteria strain containing the ΔlktCAV4 cassette. Amplification products of 1867 base pairs were expected for either M. haemolytica serotype 1 or serotype 6 bacteria strain containing the M. bovis insert (ΔlktCAV4Mbovis). Because the expected amplification product from the ΔlktCAV4Mbovis cassette is relatively large, a second primer pair was utilized to assure positive identification. This primer pair was designed to amplify an internal fragment of the synthetic M. bovis DNA insert. The sequence of the forward primer MbovispolyF is 5'-ggagaaaatgtcaactt-gaaagta-3' and is set forth in SEQ ID NO: 24; the sequence of the reverse primer MbovispolyR is 5'-ggattccacctaagt-taaattgt-3' and is set forth in SEQ ID NO: 25. The expected size of this amplification product is 340 bp and is only produced from M. haemolytica carrying the synthetic M. bovis insert.

The representative colonies were also subjected to multiplex PCR analysis to determine their capsular type (serotype). Two separate primer pairs were utilized which target biosynthetic genes in the M. haemolytica capsular biosynthetic operons of serotype 1 and serotype 6. The sequence of the forward primer MhSt1F is 5'-acaccaaagcaacagactgc-3' and is set forth in SEQ ID NO: 26; the sequence of the reverse primer MhSt1R is 5'-cctgtaaaggcatctgccca-3' and is set forth in SEQ ID NO: 27. This primer pair produces an amplification product of 125 base pairs from only serotype 1 M. haemolytica. The sequence of the forward primer MhSt6F is 5'-ttggtgcttgggagtatgcc-3' and is set forth in SEQ ID NO: 27, and the sequence of the reverse primer MhSt6R is 5'-atcggaaacggtttgctgga-3' and is set forth in SEQ ID NO: 28. This primer pair produces an amplification product of 294 base pairs from only serotype 6 M. haemolytica.

Example 6

Cattle Vaccination for Mannheimia Challenge

Calves were vaccinated with a mixture of D153ΔlktCAV4 and D174ΔlktCAV4; or a mixture of ΔlktCAV4Mbovis and D174ΔlktCAV4Mbovis, followed by challenge with M. haemolytica isolate D153. An unvaccinated control group of calves were used for comparison. After challenge, cattle vaccinated with either mixture, with or without an Mbovis payload, showed reduced M. haemolytica lung load, reduced gross lung lesions, and reduced mortality, compared to unvaccinated cattle vaccinated which showed high M. haemolytica lung load, severe lung lesions, and severe symptoms which warranted euthanasia.

Twenty Holstein calves, approximately 8 weeks of age and started on solid feed, were enrolled in the study. The calves had been caught, colostrum deprived, and were isolated in individual hutches until shipment to the USDA's National Animal Disease Center (NADC). Upon arrival the calves were randomly allocated to 3 groups (one group unvaccinated n=8, and two groups vaccinated n=6 per group) housed indoors in a climate-controlled biocontainment facility. Each group was divided among 3-4 rooms, for a total of 10 rooms, with 2 calves in each room. The calves were fed twice per day calf starter (Calf STARTENA; Purina Mills, Gray Summit, Missouri, USA) and hay cubes as much as they would clean up before the next feeding. Fresh water was provided ad libitum.

One week post arrival (designated day 0) the calves were vaccinated by intranasal instillation of the above experimental vaccine preparations. Group 1 calves remained unvaccinated, Group 2 calves received M. haemolytica ΔlktCAV4 vaccine product (vaccine without M. bovis antigen payload), while Group 3 calves received ΔlktCAV4Mbovis vaccine product (vaccine with M. bovis antigen payload).

Serotype 1 and serotype 6 modified-live M. haemolytica strains D153ΔlktCAV4 and D174ΔlktCAV4 prepared as in Example 1, and the D153ΔlktCAV4Mbovis and D174ΔlktCAV4Mbovis vaccine products prepared as in Example 2, were grown overnight on Columbia agar plates with 5% defibrinated bovine blood (4 total cultures). Pure culture growth was harvested with DACRON polyester fiber (Du Pont de Nemours and Company; Wilmington, Delaware, USA) swabs, and each inoculated into 400 mL Columbia broth (in 1 liter Erlenmeyer flasks) until an OD 600 of 0.1 was achieved. The flasks were incubated at 37° C. with shaking at 200 rpm until an OD 600 of approximately 0.65 was achieved, at which point 40 g skim milk powder (Merck 115363) was thoroughly mixed and the cultures were flash-frozen in trays for lyophilization. The lyophilized powders so generated were evaluated by culture to quantitate viable Mannheimia. The day of vaccination the lyophilized powders were resuspended in EBSS to produce approximately $2.5 \times 10^8$ CFU/mL for each vaccine strain and the suspensions placed on ice. At the barn, two inocula were formed by combining serotype 1 and serotype 6 of modified-live M. haemolytica ΔlktCAV4 and of ΔlktCAV4Mbovis vaccine product. An aliquot of each inoculum was returned to the laboratory for quantitative culture and PCR analysis.

The inoculum with M. haemolytica ΔlktCAV4 was determined to contain $2.2 \times 10^8$ CFU/mL for a total dose of $8.8 \times 10^8$ CFU per calf. Twenty representative colonies were tested by PCR and were determined to be evenly divided between M. haemolytica serotype 1 and M. haemolytica serotype 6. All were confirmed to contain the expected changes in the M. haemolytica lktCA gene cluster, and not to contain M. bovis insert. The inoculum with ΔlktCAV4Mbovis was determined to contain $3.0 \times 10^8$ CFU/mL for a total dose of $1.2 \times 10^9$ CFU per calf. The inoculum was determined to be evenly divided between M. haemolytica serotype 1 and M. haemolytica serotype 6 and all representative colonies were confirmed to contain the expected changes in the M. haemolytica lktCA gene cluster, and to contain the M. bovis insert.

Four mL of the vaccine was deposited, 2 mL per nostril, utilizing a MAD NASAL, intranasal mucosal atomization device (Teleflex; Limerick, Pennsylvania, USA) attached to a 5 mL disposable syringe. The devices were reused for calves within each room, but new devices were used in each successive room. An aliquot of each challenge inoculum was placed on ice prior to mixing and afterwards for quantitative culture.

Example 7

Challenge with *M. Haemolytica*

This example shows that vaccination with D153ΔlktCAV4, D174ΔlktCAV4, D153ΔlktCAV4Mbovis, and D174ΔlktCAV4Mbovis vaccine products protect cattle from *M. haemolytica* challenge.

All calves were observed twice daily for general health, appetite, and demeanor, for the duration of the experiment. Following *Mannheimia* challenge an additional daily observation time point was included, for a total of 3 observations per day, which were continued for the remainder of the experiment. Jugular blood (for serum), nasal swabs (for culture), and tears (for ELISA) were collected weekly. Rectal temperatures were collected twice daily following virulent *Mannheimia* challenge until necropsy.

An intratracheal challenge system was utilized over a span of 3 days where a subset of each group was challenged on any given day. A stock of lung homogenate was grown overnight on Columbia Blood Agar +5% bovine blood. *Mannheimia* growth was harvested then diluted in EBSS to create a stock at an OD600=0.6. For each calf, 1.25 mL stock diluted in 100 mL EBSS was administered for challenge followed by 100 mL sterile EBSS. *Mannheimia* was used unwashed, all preparations were kept on ice prior to animal inoculation. Administration utilized an 18-gauge hypodermic needle inserted into the tracheal lumen. This procedure was repeated for all three challenge days whereby 2 calves of each group were challenged on days 29 and 30, and the remaining calves (a total of 8 calves including 4 controls) were challenged on day 30. Challenge dose was quantitated each day of preparation.

A semi-quantitative technique was used for bacterial specimen culture whereby nasal swabs were struck in a consistent manner on the primary zone of blood agar plates, then a sterile swab was used to generate secondary and tertiary zones. Following overnight incubation, suspect colonies were enumerated, and representative colonies were passed for PCR confirmation of identity and serotype.

With respect to colonization and shedding of vaccine strains, both serotypes of the vaccine strains were detected in nasal swab specimens in the two vaccinated groups (Group 2 and Group 3). Recovery of the vaccine strains was high initially and progressively waned throughout the 4 weeks vaccination phase. Vaccine strains were still detected in 2 of 3 rooms for each of the vaccinated groups at the time of challenge. No adverse reactions were observed in the vaccinated calves. No *Mannheimia* were detected in the unvaccinated group prior to challenge (Group 1). All representative isolates were confirmed to contain the expected genetic deletion in the lktCA gene cluster.

*Mannheimia* recovery from nasal swabs following vaccination. Numbers of culture-positive animals and semi-quantitative shedding score are shown on Table 2, below.

|  | Days after vaccination | | | | | | | |
| --- | --- | --- | --- | --- | --- | --- | --- | --- |
|  | D-5 | D0 | D1 | D3 | D7 | D14 | D21 | D28 |
| Control | 0/8 | 0/8 | NS | 0/8 | 0/8 | 0/8 | 0/8 | 0/8 |
| LktV4 | 0/6 | 0/6 | 6/6 | 6/6 | 3/6 | 2/6 | 2/6 | 2/6 |
|  |  |  | 14+ | 7.5+ | 6.0+ | 3.5+ | 4.0+ | 1.0+ |
| LktV4 Mb | 0/6 | 0/6 | 6/6 | 6/6 | 4/6 | 2/6 | 2/6 | 2/6 |
|  |  |  | 15+ | 6.0+ | 5.0+ | 4.5+ | 4.5+ | 5.0+ |

Following challenge, unvaccinated Group 1 calves exhibited a steady rise in rectal temperatures until mortality or euthanasia. In contrast to unvaccinated calves, the vaccinated Group 2 and Group 3 calves exhibited an early rise in rectal temperature within hours of challenge which then declined on successive days.

All 12 vaccinated calves survived to scheduled euthanasia 3 days after challenge. In the unvaccinated control group (Group 1) 2 of 8 calves reached clinical endpoints which warranted euthanasia prior to schedule, 4 succumbed to pneumonia prior to schedule, and only 2 survived to scheduled euthanasia. Seven of 8 Group 1 calves exhibited depression, tachypnea, and anorexia. In general, the vaccinated calves remained alert and feeding, though feed intake was reduced the day following challenge. One vaccinated calf exhibited tachypnea 2 days following challenge.

Heavy growth of the challenge strain of *Mannheimia* was recovered from liver tissue and tracheal swab specimens of all unvaccinated Group 1 calves. Seven of 8 Group 1 calves also yielded heavy growth from spleen specimens. No growth was observed from liver or spleen specimens of Group 2 vaccinates (ΔlktCAV4 vaccine), and light growth was observed from 1 of 6 tracheal swab specimens in this group. Group 3 (ΔlktCAV4Mbovis vaccine) calves yielded light growth from 2 of 6 spleen swabs and 1 of 6 liver swabs. Light growth was also observed from tracheal swab specimens of Group 3.

Total lung lesion volume, corrected for the air exchange contribution of each lung lobe, was significantly higher in the unvaccinated Group 1. An average of 49.7% of unvaccinated Group 1 calf lung was visibly damaged compared to an average of 8.2% damage in Group 2 vaccinates and 17.3% in Group 3 vaccinates. All Group 1 calves exhibited extensive fibrinous consolidation with numerous pleural adhesions, including 6 calves which exhibited pleural effusion. One Group 2 calf exhibited a single pleural adhesion, and 2 Group 3 calves exhibited multiple pleural adhesions. The lung lesions were significantly reduced, $P<0.000001$ comparing Group 2 with Group 1, and $P<0.001$ comparing Group 3 with Group 1, based on two-tailed Student's t-test. Group 2 did not statistically differ from Group 3, $P>0.25$.

Quantitative culture of affected and unaffected lung tissue demonstrated a reduction in infectious bacterial load in both vaccinated Group 2 and Group 3 calves compared to unvaccinated Group 1 control calves. All lobes tested from Group 1 were culture positive for *Mannheimia* with a geometric mean load of $6.2 \times 10^9$ CFU recovered per gram of lung tissue. In vaccinated Group 2 (no *M. bovis* payload), 17 of 30 lung specimens were culture positive for *Mannheimia* with a geometric mean load of $2.8\times10^4$ CFU/gram of lung tissue. In vaccinated Group 3 (plus *M. bovis* payload), 25 of 30 lung specimens were culture positive for *Mannheimia* with a geometric mean load of $2.4\times10^6$ CFU/gram of lung tissue.

Indirect ELISA was conducted using *Mannheimia* whole cell antigen and secondary antibodies anti-bovine IgG1 and anti-bovine IgG2 for serum specimens or anti-bovine IgG whole molecule and anti-bovine IgA for tear secretion specimens. The IgG1 *Mannheimia* titers in serum from calves challenged with *Mannheimia* are shown in FIG. 6. The IgG2 *Mannheimia* titers in serum from calves challenged with *Mannheimia* are shown in FIG. 7. The IgG *Mannheimia* titers in tear secretions from calves challenged with *Mannheimia* are shown in FIG. 8. The IgA *Mannheimia* titers in tear secretions from calves challenged with *Mannheimia* are shown in FIG. 9. These results show that Group 1 calves exhibited low and relatively steady serum and tear secretion titers throughout the trial. Calves from Groups 2 and 3 exhibited increased IgG1 and IgG2 serum titers within 2 weeks of vaccination which continued to rise throughout the trial. These vaccinated groups also exhibited increased mucosal antibody titers in tear secretions, both IgG and IgA, within 1 week of vaccination.

We claim:

1. A cassette comprising a modified *Mannheimia haemolytica* lktCA gene cluster, wherein the modified *M. haemolytica* lktCA gene cluster comprises two polynucleotides encoding leukotoxin neutralizing epitopes, a first polynucleotide encoding the native leukotoxin neutralizing epitope, and a second polynucleotide encoding an additional leukotoxin neutralizing epitope inserted immediately downstream of the native leukotoxin A start codon.

2. A composition comprising the cassette of claim 1, wherein the composition is a polynucleotide, a plasmid, an expression vector, a host cell, a vaccine, or an immunogenic composition.

3. The composition of claim 2, wherein the composition is a replacement plasmid, an attenuated *M. haemolytica* strain A1 bacterium, or an attenuated *M. haemolytica* strain A6 bacterium.

4. The cassette of claim 1, further comprising at least one polynucleotide encoding a heterologous antigen.

5. The cassette of claim 4, wherein the at least one polynucleotide encoding a heterologous antigen is inserted upstream of the polynucleotide encoding the added leukotoxin neutralizing epitope.

6. A composition comprising the cassette of claim 4, wherein the composition is a polynucleotide, a plasmid, an expression vector, a host cell, a vaccine, or an immunogenic composition.

7. The cassette of claim 4, wherein the at least one polynucleotide encoding a heterologous antigen is at least one *M. bovis* antigen.

8. A kit comprising the cassette of claim 1.

9. A kit comprising the cassette of claim 4.

10. A kit comprising the composition of claim 6.

* * * * *